United States Patent
Defossa et al.

(10) Patent No.: US 11,897,876 B2
(45) Date of Patent: Feb. 13, 2024

(54) ISOXAZOLIDINES AS RIPK1 INHIBITORS AND USE THEREOF

(71) Applicant: GENZYME CORPORATION, Cambridge, MA (US)

(72) Inventors: Elisabeth Defossa, Frankfurt am Main (DE); Uwe Heinelt, Frankfurt am Main (DE); Hans Matter, Frankfurt am Main (DE); Maria Mendez-Perez, Frankfurt am Main (DE); Nils Rackelmann, Frankfurt am Main (DE); Kurt Ritter, Frankfurt am Main (DE); Hauke Szillat, Frankfurt am Main (DE); Gernot Zech, Frankfurt am Main (DE)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 17/983,883

(22) Filed: Nov. 9, 2022

(65) Prior Publication Data

US 2023/0203027 A1  Jun. 29, 2023

(51) Int. Cl.
C07D 417/14 (2006.01)
(52) U.S. Cl.
CPC .................................. *C07D 417/14* (2013.01)
(58) Field of Classification Search
CPC .................................................... C07D 417/14
USPC ........................................................ 514/256
See application file for complete search history.

(56) References Cited

FOREIGN PATENT DOCUMENTS

| KR | 10-2020-0087922 A | 7/2020 |
|---|---|---|
| WO | WO 2014/125444 A1 | 8/2014 |
| WO | WO 2016/027253 A1 | 2/2016 |
| WO | WO 2016/101887 A1 | 6/2016 |
| WO | WO 2016/185423 A1 | 11/2016 |
| WO | WO 2017/069279 A1 | 4/2017 |
| WO | WO 2017/096301 A1 | 6/2017 |
| WO | WO 2017/136727 A2 | 8/2017 |
| WO | WO 2018/092089 A1 | 5/2018 |
| WO | WO 2018/213632 A1 | 11/2018 |
| WO | WO 2019/086494 A1 | 5/2019 |
| WO | WO 2019/130230 A1 | 7/2019 |
| WO | WO 2019/204537 A1 | 10/2019 |
| WO | WO 2020/043173 A1 | 3/2020 |

OTHER PUBLICATIONS

Dondelinger et al., "NF-κB-Independent Role of IKKα/IKKβ in Preventing RIPK1 Kinase-Dependent Apoptotic and Necroptotic Cell Death during TNF Signaling", Molecular Cell, Oct. 1, 2015, 60(1): 63-76.
European Search Report for European Patent Application No. 21315242.4, dated Apr. 11, 2022.
Fusco et al., "Incontinentia pigmenti: report on data from 2000 to 2013", Orphanet Journal of Rare Diseases, 2014, 9: 93.
International Search Report and Written Opinion for PCT International Patent Application No. PCT/EP2021/064657, dated Aug. 4, 2021.
Ridder et al., "Brain endothelial TAK1 and NEMO safeguard the neurovascular unit", J Exp Med., Sep. 2015, 212 (10): 1529-1549.
Smahi et al., "Genomic rearrangement in NEMO impairs NF-κB activation and is a cause of incontinentia pigmenti. The International Incontinentia Pigmenti (IP) Consortium", Nature, Jun. 2000, 405(6785): 466-472.
U.S. Appl. No. 17/983,883, filed Nov. 9, 2022, Elisabeth Defossa, Isoxazolidines as RIPK1 Inhibitors and Use Thereof.
U.S. Appl. No. 17/926,913, filed Nov. 21, 2022, Elisabeth Defossa, Isoxazolidines as RIPK1 Inhibitors and Use Thereof.
Cai et al., "Plasma membrane translocation of trimerized MLKL protein is required for TNF-induced necroptosis", Nat Cell Biol., Jan. 2014, 16(1): 55-65, [ePub Dec. 8, 2013].
Ertl et al., "Fast Calculation of Molecular Polar Surface Area as a Sum of Fragment-Based Contributions and Its Application to the Prediction of Drug Transport Properties", J. Med. Chem., 2000, 43(20): 3714-3717.
Hara et al., "Inhibition of interleukin 1β converting enzyme family proteases reduces ischemic and excitotoxic neuronal damage", Proc. Natl. Acad. Sci. USA, Mar. 4, 1997, 94(5): 2007-2012.
Harris et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase", J Med Chem., May 23, 2019, 62(10): 5096-5110.
Lawlor et al., "RIPK3 promotes cell death and NLRP3 inflammasome activation in the absence of MLKL", Nature Communications, Feb. 18, 2015, 6: 6282.
Lee et al., "Interferon-gamma regulates inflammatory cell death by targeting necroptosis in experimental autoimmune arthritis", Scientific Reports, Aug. 31, 2017, 7: 10133.
Orozco et al., "Structural attributes influencing unbound tissue distribution", European Journal of Medicinal Chemistry, Jan. 2020, 185(1): 111813.

*Primary Examiner* — Kahsay Habte
(74) *Attorney, Agent, or Firm* — LATHROP GPM LLP; James H. Velema, Esq.

(57) ABSTRACT

The present disclosure relates to isoxazolidines and their use as receptor-interacting protein kinase 1 inhibitors, for example in the treatment of diseases and disorders mediated by RIP kinase 1.

27 Claims, No Drawings

ISOXAZOLIDINES AS RIPK1 INHIBITORS AND USE THEREOF

RELATED APPLICATIONS

This application claims the benefit of European Patent Application No. 21315242.4, filed Nov. 11, 2021, the entire disclosure of which is hereby incorporated herein by reference.

BACKGROUND

Although inflammation can be a protective mechanism in response to harmful stimuli, such as invasion of pathogens and tissue damages, chronic inflammation is an important underlying factor in many human diseases, such as neurodegeneration, rheumatoid arthritis, autoimmune and inflammatory diseases, and cancer. Similarly, the activation of cell death pathways, such as necrosis and apoptosis, which are useful in eliminating infected or damaged cells, is also an important underlying mechanism for human diseases, including acute and chronic neurodegenerative diseases. Receptor-interacting protein kinase 1 (UniProtKB Q13546) is a key regulator of inflammation, apoptosis, and necroptosis. Receptor-interacting protein kinase 1 has an important role in modulating inflammatory responses mediated by nuclear-factor kappa-light chain enhancer of activated B cells (NF-κB). More recent research has shown that its kinase activity controls necroptosis, a form of necrotic cell death, which was traditionally thought to be passive and unregulated, and is characterized by a unique morphology. Further, receptor-interacting protein kinase 1 is part of a pro-apoptotic complex indicating its activity in regulating apoptosis.

The receptor-interacting protein kinase 1 is subject to complex and intricate regulatory mechanisms, including ubiquitylation, deubiquitylation, and phosphorylation. These regulatory events collectively determine whether a cell will survive and activate an inflammatory response or die through apoptosis or necroptosis. Dysregulation of receptor-interacting protein kinase 1 signaling can lead to excessive inflammation or cell death, and conversely, research has shown that inhibition of receptor interacting protein kinase 1 can be effective therapies for diseases involving inflammation or cell death. RIPK1 inhibition has been identified as promising principle to address different diseases like rheumatoid arthritis (RA), psoriasis, multiple sclerosis, Alzheimer's disease, and inflammatory bowel disease, such as Crohn's disease or ulcerative colitis (UC). To treat some of these diseases like multiple sclerosis (MS) and Alzheimer's disease, access to the central nervous system (CNS) is required, while for other diseases like rheumatoid arthritis, psoriasis, inflammatory bowel disease (IBD), such as Crohn's disease or UC, access to the CNS is not essentially required.

The most advanced RIPK1 inhibitor, GSK2982772 (oxazepinone derivative disclosed in WO2014/125444), was evaluated for RA, psoriasis, and UC in phase II clinical trails Dihydropyrazoles and Isoxazolidines as RIPK1 inhibitors are well known (GSK WO2018092089, WO2019130230). GSK published dihydropyrazoles with phenyl substituent on isoxazolidin and pyrimidine with good efficacy on inhibition of RIPK1 (comparator compound A, WO2018092089, Example 4, pIC50=8-9 (GSK data), IC50 (U937)=8 nM, own data). The analogous isoxazolidine, comparator compound B, has the same efficacy (IC50 (U937)=9 nM, own data). Exchange of the substituent to a heteroaryl ring on pyrimidine ring leads to less effective dihydropyrazole (comparator compound C, WO2018092089, Example 129, pIC50=7-9 (GSK data), pIC50 (U937)=59 nM, own data). For the same substitution pattern in the isoxazolidine series the efficacy dropped further compared to the phenyl substitution of comparator compound B (comparator compound D, IC50 (U937)=92 nM, own data).

The introduction of substituents, like F, Cl, $CH_3$ or CN, on the phenyl residue on isoxazolidine lead to a compound with lower efficacy (comparator compound E, IC50 (U937)=197 nM, own data).

Surprisingly, the exchange of 1,3,4-oxadiazole to optionally substituted imidazole, pyrazole and triazole heteroaromatic 5-membered rings lead to compounds with high efficacy on RIPK1 inhibition, e.g. example 8 with IC50 (U937)=1 nM (own data), see scheme A and table 1).

Scheme A

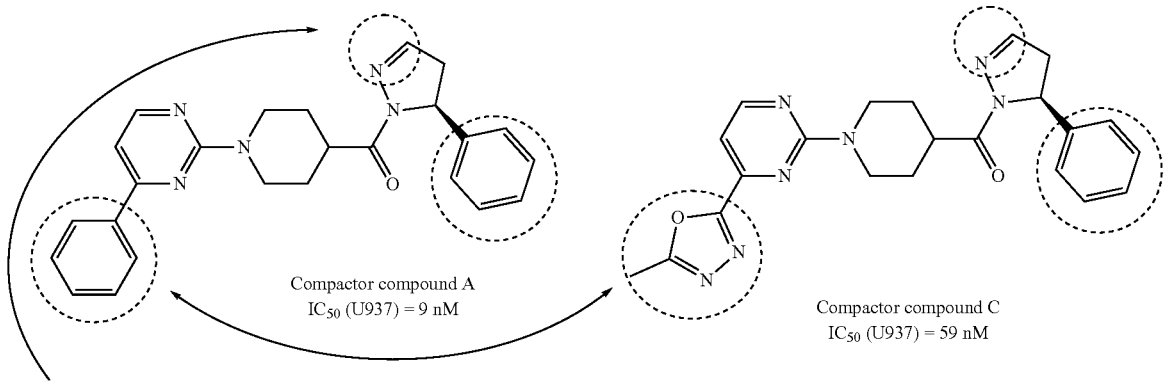

-continued

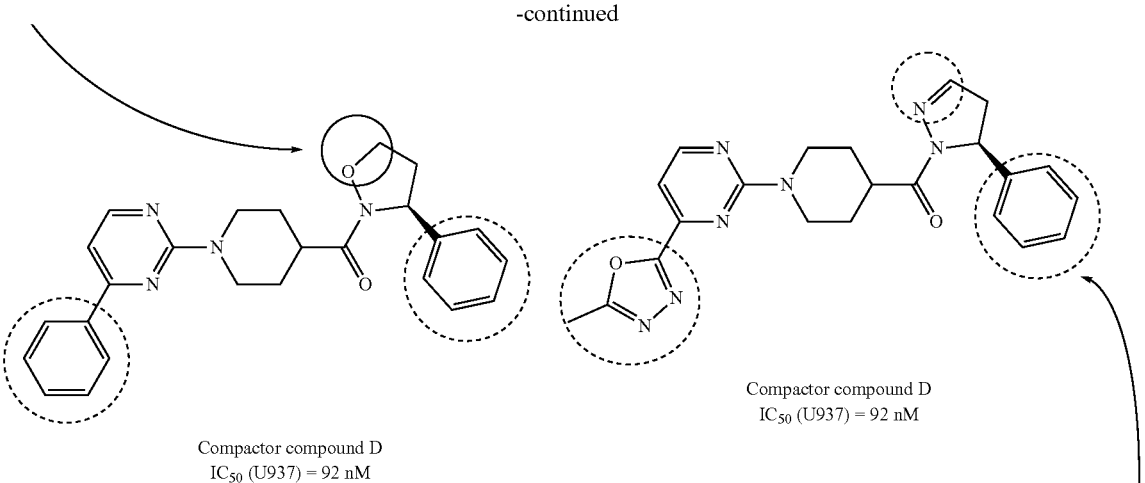

Compactor compound D
IC$_{50}$ (U937) = 92 nM

Compactor compound D
IC$_{50}$ (U937) = 92 nM

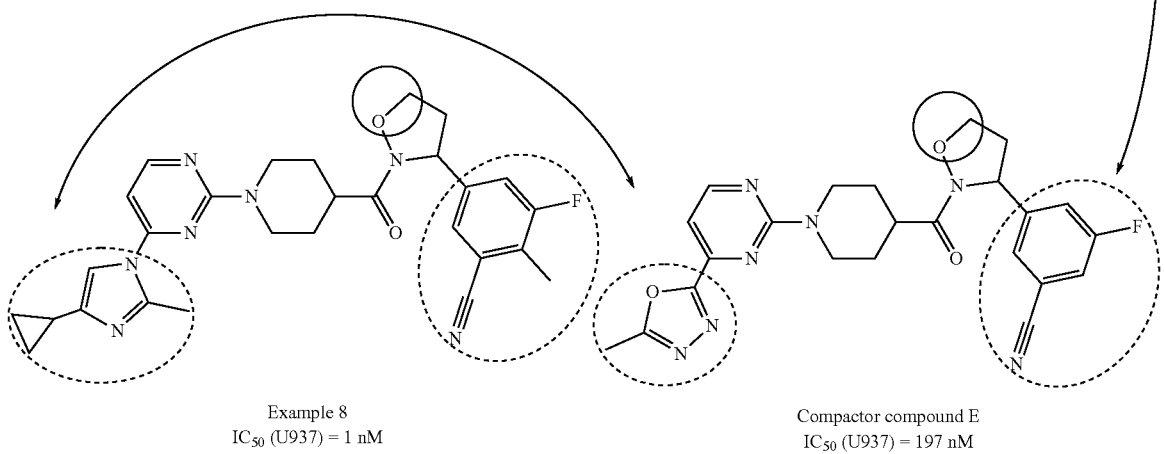

Example 8
IC$_{50}$ (U937) = 1 nM

Compactor compound E
IC$_{50}$ (U937) = 197 nM

SUMMARY

Disclosed herein are compounds of formula I:

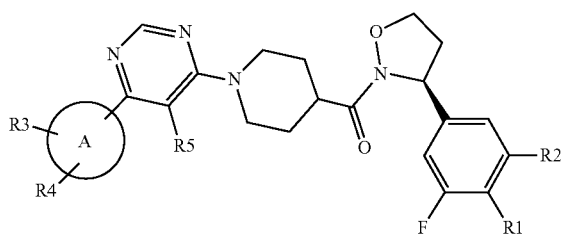

(I)

wherein
A represents a five-membered heteroaryl group which 2 or 3 ring atoms are selected independently from nitrogen, which is optionally substituted by R3 and R4;
R1 represents H or CH$_3$,
R2 represents Cl, F or CN,
R3 represents H or CH$_3$,
R4 represents H, CH$_3$ or cyclopropyl,
R5 represents H or F;

or a pharmaceutically acceptable salt, solvate, or stereoisomer thereof.

In another aspect provided are methods for making the compounds and intermediates thereof.

In a related aspect, provided herein is a pharmaceutical composition comprising a compound of the disclosure and a pharmaceutically acceptable carrier.

In another aspect, provided herein is a method of inhibiting receptor-interacting protein kinase 1. Further provided are methods for treating receptor-interacting protein kinase 1-mediated disease or disorder comprising administering a therapeutically effective amount of a compound or a pharmaceutical composition as described herein to a subject in need thereof. The disclosure also provides uses of the compounds or compositions thereof in the manufacture of a medicament for the treatment of a disease, disorder or condition that is mediated by (or mediated, at least in part, by) receptor-interacting protein kinase 1.

DETAILED DESCRIPTION

Definitions

As used herein chemical nomenclature as not defined otherwise have the meanings as being used in the technical field.

As used herein, the term "five-membered heteroaryl group in which 2 to 3 ring atoms are selected from nitrogen", by itself or as part of another substituent, refers to a monocyclic aromatic ring assembly containing 5 atoms, where from 2 to 3 of the ring atoms are nitrogen heteroatoms.

For example, heteroaryl groups can be $C_5$ heteroaryl, wherein 2 carbon ring atoms are replaced with nitrogen heteroatoms; or $C_5$ heteroaryl, wherein 3 carbon ring atoms are replaced with nitrogen heteroatoms. The heteroaryl group can include groups such as imidazole, pyrazole and triazole.

Heteroaryl groups can be substituted or unsubstituted. The heteroaryl groups can be linked via any position on the ring. For example, imidazole includes 1-, 2-, 4- and 5-imidazole, pyrazole includes 1-, 3-, 4- and 5-pyrazole, triazole includes 1-, 4- and 5-triazole.

As used herein, the term "pharmaceutically acceptable excipient" refers to a substance that aids the administration of an active agent to a subject. By "pharmaceutically acceptable", it is meant that the excipient is compatible with the other ingredients of the pharmaceutical composition and is not deleterious to the recipient thereof.

Pharmaceutical excipients useful in the present disclosure include, but are not limited to, binders, fillers, disintegrants, lubricants, glidants, coatings, sweeteners, flavors and colors.

As used herein, the term "salt" refers to acid or base salts of the compounds of the disclosed herein. Illustrative examples of pharmaceutically acceptable salts are mineral acid salts, organic acid salts, quaternary ammonium salts. It is understood that the pharmaceutically acceptable salts are non-toxic.

Pharmaceutically acceptable salts of the acidic compounds disclosed herein are salts formed with bases, namely cationic salts such as alkali and alkaline earth metal salts. Similarly, acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure. In addition to salt forms, described herein are compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject who is at risk or has a family history of the disease or condition.

"Subject" refers to a human, that has been or will be the object of treatment. The methods described herein may be useful in human therapy.

The term "therapeutically effective amount" or "effective amount" of a compound of the disclosure or a pharmaceutically acceptable salt, tautomer, stereoisomer, mixture of stereoisomers, thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

Disclosed herein are compounds of formula I:

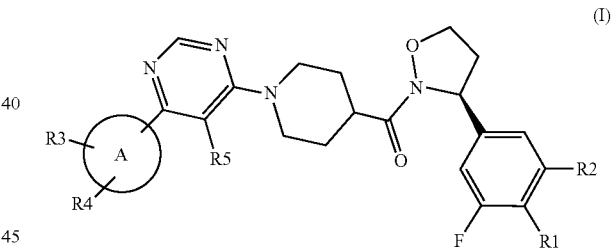

wherein
 A represents a five-membered heteroaryl group in which 2 or 3 ring atoms are independently selected from nitrogen, which is optionally substituted by R3 and R4;
 R1 represents H or CH$_3$,
 R2 represents Cl, F or CN,
 R3 represents H or CH$_3$,
 R4 represents H, CH$_3$ or cyclopropyl,
 R5 represents H or F;
 or a pharmaceutically acceptable salt, solvate, or stereoisomer thereof.

One embodiment are compounds of formula I,
wherein
 A is a heteroaryl selected from the group of imidazole, pyrazole, and triazole, which is optionally substituted by R3 and R4;
 or a pharmaceutically acceptable salt, solvate, or stereoisomer thereof.

One embodiment are compounds of formula I,
wherein
A is imidazole, which is optionally substituted by R3 and R4;
or a pharmaceutically acceptable salt, solvate, or stereoisomer thereof.

One embodiment are compounds of formula I,
wherein
A is pyrazole, which is optionally substituted by R3 and R4;
or a pharmaceutically acceptable salt, solvate, or stereoisomer thereof.

One embodiment are compounds of formula I,
wherein
A is a triazole, which is optionally substituted by R3 and R4;
or a pharmaceutically acceptable salt, solvate, or stereoisomer thereof.

One embodiment are compounds of formula I,
wherein
A represents a heteroaryl selected from
1-imidazolyl, 2-imidazolyl, 4-imidazolyl, 5-imidazolyl, 1-pyrazolyl, 3-pyrazolyl, 4-pyrazolyl, 5-pyrazolyl, 1,2,3-triazole-1-yl, 1,2,3-triazole-4-yl, 1,2,3-triazole-5-yl, 1,2,4-triazole-1-yl, 1,2,4-triazole-3-yl and 1,2,4-triazole-5-yl;
which is optionally substituted by R3 and R4;
or a pharmaceutically acceptable salt, solvate, or stereoisomer thereof.

One embodiment are compounds of formula I,
wherein
A represents a heteroaryl selected from

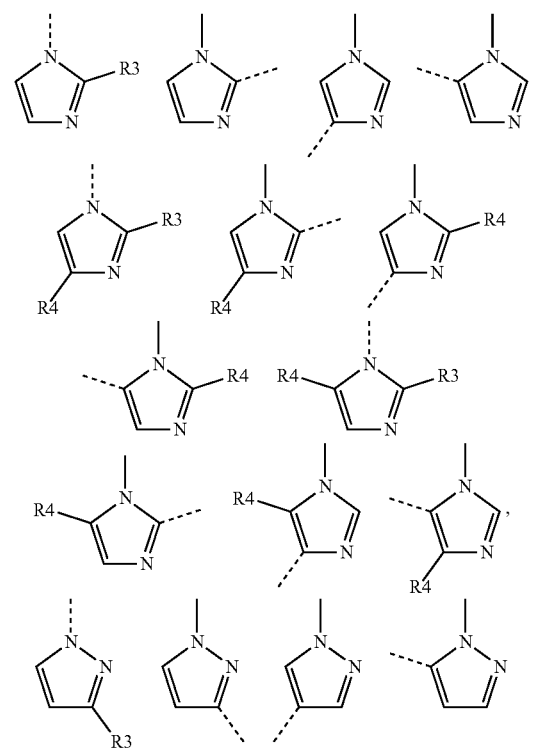

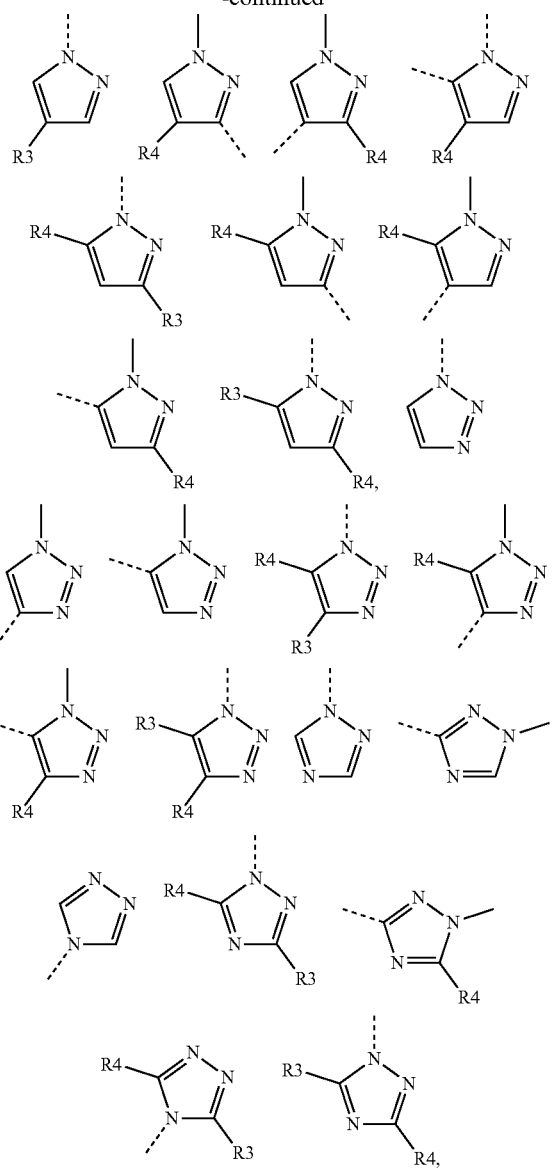

wherein the dashed line indicates the bond to the pyrimidine ring of formula I;
R3 represents H or CH$_3$; and
R4 represents H, CH$_3$ or cyclopropyl;
or a pharmaceutically acceptable salt, solvate, or stereoisomer thereof.

One embodiment are compounds of formula I,
wherein
A represents a heteroaryl selected from
1-imidazolyl,
1-pyrazolyl, 3-pyrazolyl, 4-pyrazolyl,
1,2,3-triazole-4-yl, and
1,2,4-triazole-1-yl;
which is optionally substituted by R3 and R4;
or a pharmaceutically acceptable salt, solvate, or stereoisomer thereof.

One embodiment are compounds of formula I,
wherein
A represents a heteroaryl selected from

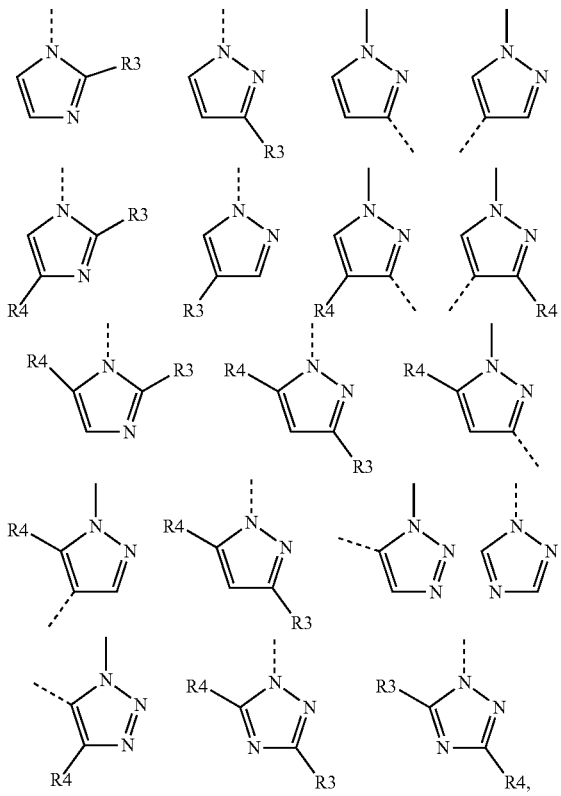

wherein the dashed line indicates the bond to the pyrimidine ring of formula I;
R3 represents H or CH$_3$; and
R4 represents H, CH$_3$ or cyclopropyl;
or a pharmaceutically acceptable salt, solvate, or stereoisomer thereof.

One embodiment are compounds of formula I,
wherein
A represents a heteroaryl selected from
1-imidazolyl and 3-pyrazolyl,
which is optionally substituted by R3 and R4;
or a pharmaceutically acceptable salt, solvate, or stereoisomer thereof.

One embodiment are compounds of formula I,
wherein one of R3 or R4 does not represent H;
or a pharmaceutically acceptable salt, solvate, or stereoisomer thereof.

One embodiment are compounds of formula I, wherein
R3 represents H; and
R4 represents CH$_3$ or cyclopropyl;
or a pharmaceutically acceptable salt, solvate, or stereoisomer thereof.

One embodiment are compounds of formula I,
wherein
R3 represents CH$_3$, and
R4 represents H;
or a pharmaceutically acceptable salt, solvate, or stereoisomer thereof.

One embodiment are compounds of formula I,
wherein
R3 represents CH$_3$, and
R4 represents CH$_3$;
or a pharmaceutically acceptable salt, solvate, or stereoisomer thereof.

One embodiment are compounds of formula I,
wherein
R3 represents CH$_3$, and
R4 represents CH$_3$ or cyclopropyl;
or a pharmaceutically acceptable salt, solvate, or stereoisomer thereof.

One embodiment are compounds of formula I,
wherein
A represents a group selected from
2-methylpyrazol-3-yl,
3-methyl-1H-pyrazol-4-yl,
4-methylpyrazol-1-yl
2,5-dimethylpyrazol-3-yl,
2-methylimidazol-1-yl,
4-cyclopropyl-2-methyl-imidazol-1-yl,
3-methyl-1,2,4-triazol-1-yl,
5-methyl-1,2,4-triazol-1-yl and
3-methyltriazol-4-yl;
or a pharmaceutically acceptable salt, solvate, or stereoisomer thereof.

One embodiment are compounds of formula I,
wherein
R1 represents CH$_3$, and
R2 represents CN;
or a pharmaceutically acceptable salt, solvate, or stereoisomer thereof.

One embodiment are compounds of formula I,
wherein
R1 represents H, and
R2 represents CN;
or a pharmaceutically acceptable salt, solvate, or stereoisomer thereof.

One embodiment are compounds of formula I,
wherein
R1 represents H, and
R2 represents F;
or a pharmaceutically acceptable salt, solvate, or stereoisomer thereof.

One embodiment are compounds of formula I,
wherein
R1 represents H, and
R2 represents Cl;
or a pharmaceutically acceptable salt, solvate, or stereoisomer thereof.

One embodiment are compounds of formula I,
wherein
A represents imidazole or pyrazole,
R1 represents H,
R2 represents CN,
R3 represents CH$_3$,
R4 represents H, and
R5 represents H or F;
or a pharmaceutically acceptable salt, solvate, or stereoisomer thereof.

One embodiment are compounds of formula I,
wherein
A represents a heteroaryl selected from
1-imidazolyl and 3-pyrazolyl,
R1 represents H,
R2 represents CN,
R3 represents CH$_3$,
R4 represents H, and
R5 represents H or F;
or a pharmaceutically acceptable salt, solvate, or stereoisomer thereof.

One embodiment are compounds of formula I,
wherein
R5 represents H,
or a pharmaceutically acceptable salt, solvate, or stereoisomer thereof.

One embodiment are compounds of formula I,
wherein
R5 represents F;
or a pharmaceutically acceptable salt, solvate, or stereoisomer thereof.

Another embodiment are compounds of formula I, selected from
3-fluoro-5-[(3S)-2-[1-[6-(2-methylimidazol-1-yl)pyrimidin-4-yl]piperidine-4-carbonyl]isoxazolidin-3-yl]benzonitrile;
3-fluoro-2-methyl-5-[(3S)-2-[1-[6-(2-methylimidazol-1-yl)pyrimidin-4-yl]piperidine-4-carbonyl]isoxazolidin-3-yl]benzonitrile;
3-fluoro-5-[(3S)-2-[1-[6-(2-methylpyrazol-3-yl)pyrimidin-4-yl]piperidine-4-carbonyl]isoxazolidin-3-yl]benzonitrile;
[(3S)-3-(3,5-difluorophenyl)isoxazolidin-2-yl]-[1-[6-(2-methylpyrazol-3-yl)pyrimidin-4-yl]-4-piperidyl]methanone;
[(3S)-3-(3-chloro-5-fluoro-phenyl)isoxazolidin-2-yl]-[1-[6-(2-methylpyrazol-3-yl)pyrimidin-4-yl]-4-piperidyl]methanone;
3-fluoro-5-[(3S)-2-[1-[6-(3-methyl-1H-pyrazol-4-yl)pyrimidin-4-yl]piperidine-4-carbonyl]isoxazolidin-3-yl]benzonitrile;
3-[(3S)-2-[1-[6-(4-cyclopropyl-2-methyl-imidazol-1-yl)pyrimidin-4-yl]piperidine-4-carbonyl]isoxazolidin-3-yl]-5-fluoro-benzonitrile;
5-[(3S)-2-[1-[6-(4-cyclopropyl-2-methyl-imidazol-1-yl)pyrimidin-4-yl]piperidine-4-carbonyl]isoxazolidin-3-yl]-3-fluoro-2-methyl-benzonitrile;
3-[(3S)-2-[1-[6-(2,5-dimethylpyrazol-3-yl)pyrimidin-4-yl]piperidine-4-carbonyl]isoxazolidin-3-yl]-5-fluoro-benzonitrile;
3-fluoro-5-[(3S)-2-[1-[6-(3-methyl-1,2,4-triazol-1-yl)pyrimidin-4-yl]piperidine-4-carbonyl]isoxazolidin-3-yl]benzonitrile;
3-fluoro-5-[(3S)-2-[1-[6-(5-methyl-1,2,4-triazol-1-yl)pyrimidin-4-yl]piperidine-4-carbonyl]isoxazolidin-3-yl]benzonitrile;
3-fluoro-5-[(3S)-2-[1-[6-(3-methyltriazol-4-yl)pyrimidin-4-yl]piperidine-4-carbonyl]isoxazolidin-3-yl]benzonitrile;
3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
3-fluoro-5-[(3S)-2-[1-[5-fluoro-6-(4-methylpyrazol-1-yl)pyrimidin-4-yl]piperidine-4-carbonyl]isoxazolidin-3-yl]-2-methyl-benzonitrile; and
[(3S)-3-(3,5-difluorophenyl)isoxazolidin-2-yl]-[1-[5-fluoro-6-(2-methylpyrazol-3-yl)pyrimidin-4-yl]-4-piperidyl]methanone;
or a pharmaceutically acceptable salt, solvate, or stereoisomer thereof.

Another embodiment are compounds of formula I, selected from
3-fluoro-5-[(3S)-2-[1-[6-(2-methylimidazol-1-yl)pyrimidin-4-yl]piperidine-4-carbonyl]isoxazolidin-3-yl]benzonitrile;
3-fluoro-5-[(3S)-2-[1-[6-(2-methylpyrazol-3-yl)pyrimidin-4-yl]piperidine-4-carbonyl]isoxazolidin-3-yl]benzonitrile; and
3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
or a pharmaceutically acceptable salt, solvate, or stereoisomer thereof.

Another embodiment is compound
3-fluoro-5-[(3S)-2-[1-[6-(2-methylimidazol-1-yl)pyrimidin-4-yl]piperidine-4-carbonyl]isoxazolidin-3-yl]benzonitrile; or a pharmaceutically acceptable salt, solvate, or stereoisomer thereof.

Another embodiment is compound
3-fluoro-5-[(3S)-2-[1-[6-(2-methylpyrazol-3-yl)pyrimidin-4-yl]piperidine-4-carbonyl]isoxazolidin-3-yl]benzonitrile; or a pharmaceutically acceptable salt, solvate, or stereoisomer thereof.

Another embodiment is compound
3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
or a pharmaceutically acceptable salt, solvate, or stereoisomer thereof.

Synthesis of Compounds

The compounds of formula I may be prepared using the methods disclosed herein and routine modifications thereof, which will be apparent given the disclosure herein and methods well known in the art.

The schemes 1 to 7 show the principal reaction steps for obtaining the example compounds of formula I.

Scheme 1 refers to intermediates which synthesis is described in detail in the example section.

Intermediates I-01, I-02a, I-02b and I-03 are the isoxalidine derivatives with the R1/R2 substituted phenyl.

To the central intermediate I-04 the R3/R4 substituted A heteroaryl building block is attached, resulting in the intermediates I-05, I-06, I-07, I-08, I-09 and I-10.

Schemes 2 to 7 show the principal reaction steps for obtaining the example compounds.

Scheme 1
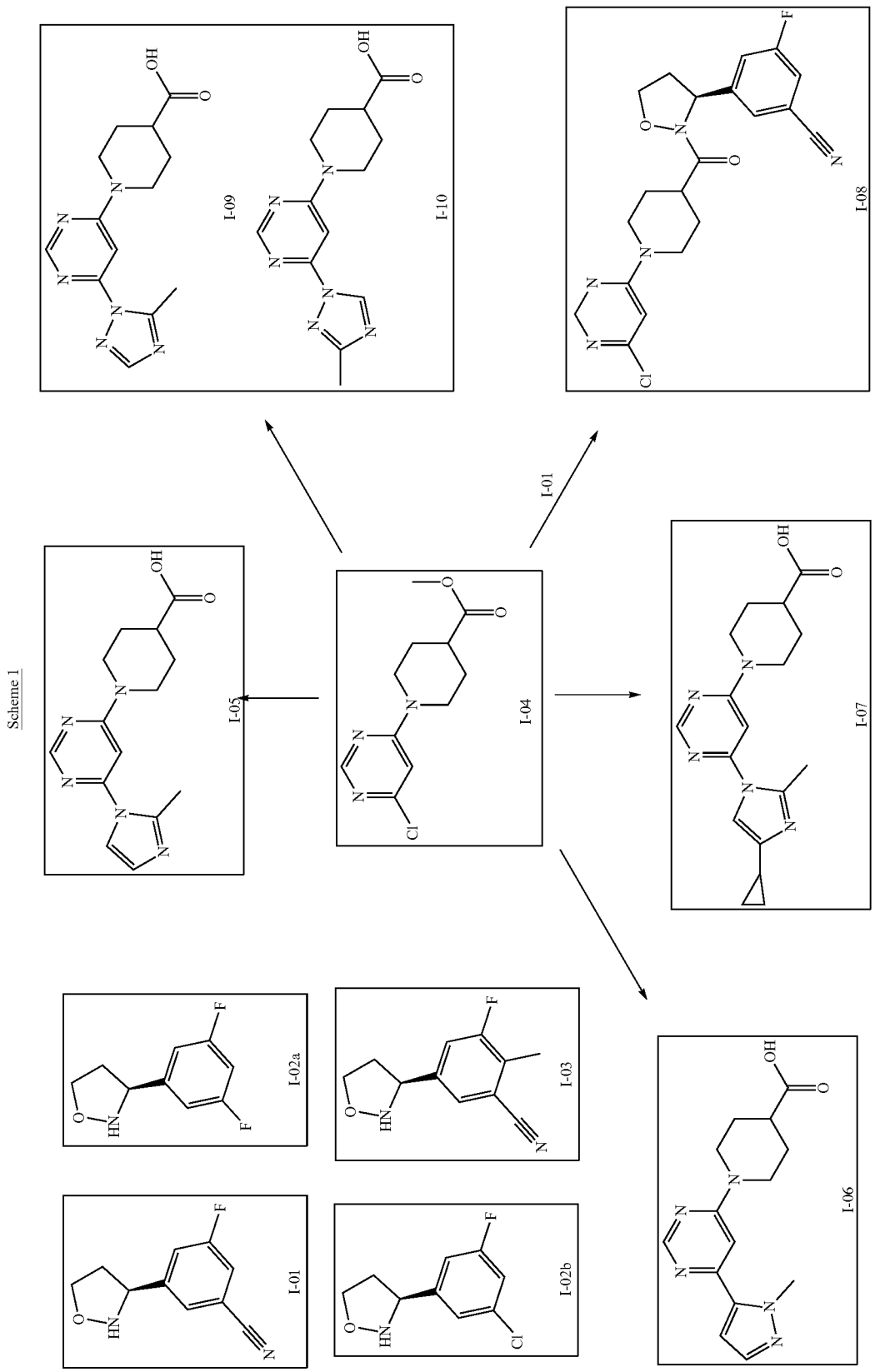

Scheme 2 (examples from Intermediate-05)
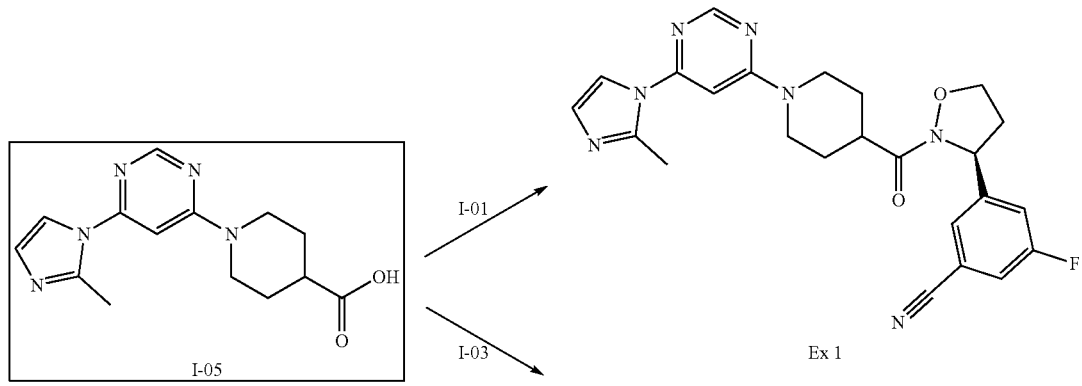
Scheme 3 (examples from Intermediate-06)
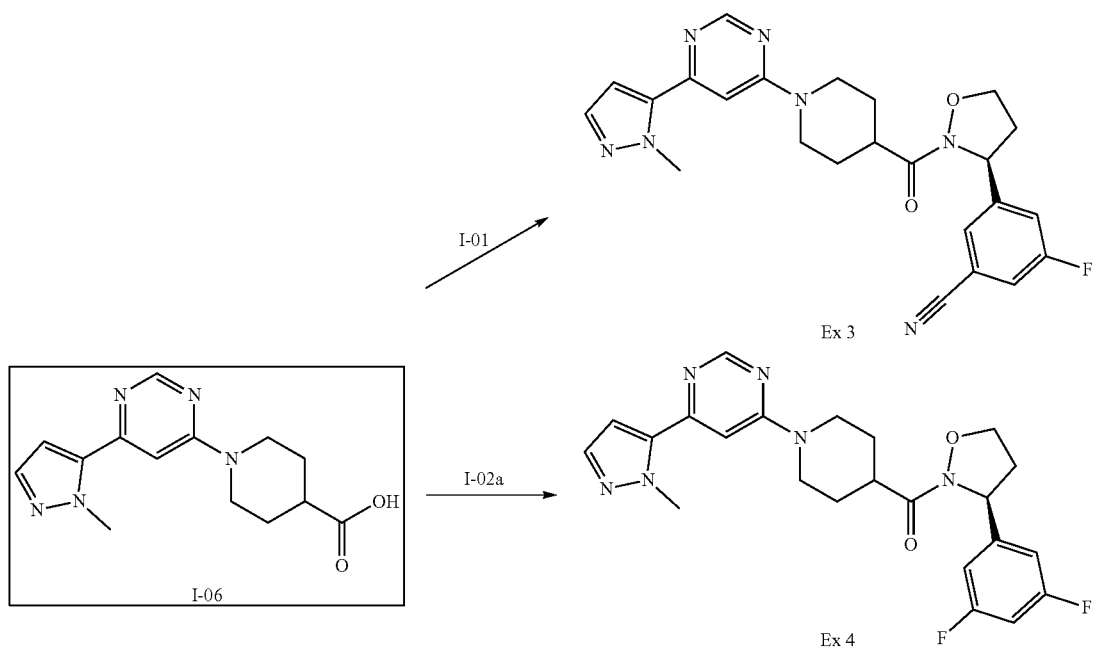

-continued
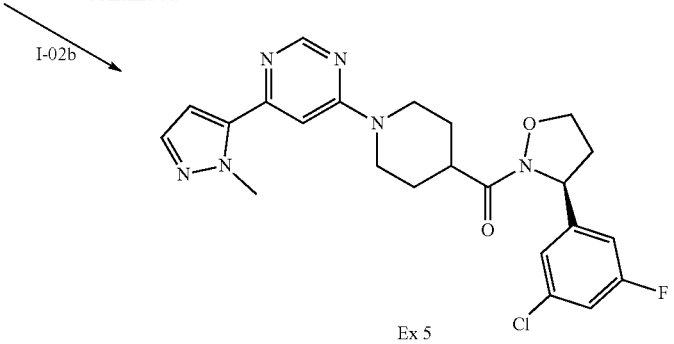
Ex 5
Scheme 4 (examples from Intermediate-07)
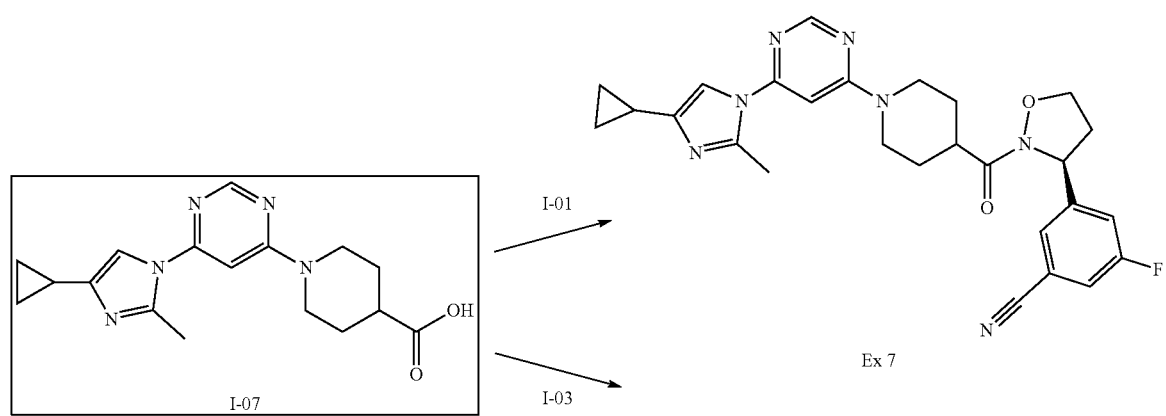
Ex 7
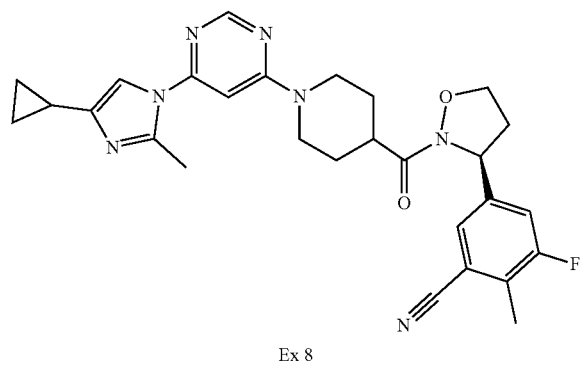
Ex 8

Scheme 5 (exampes from Intermediate-08)
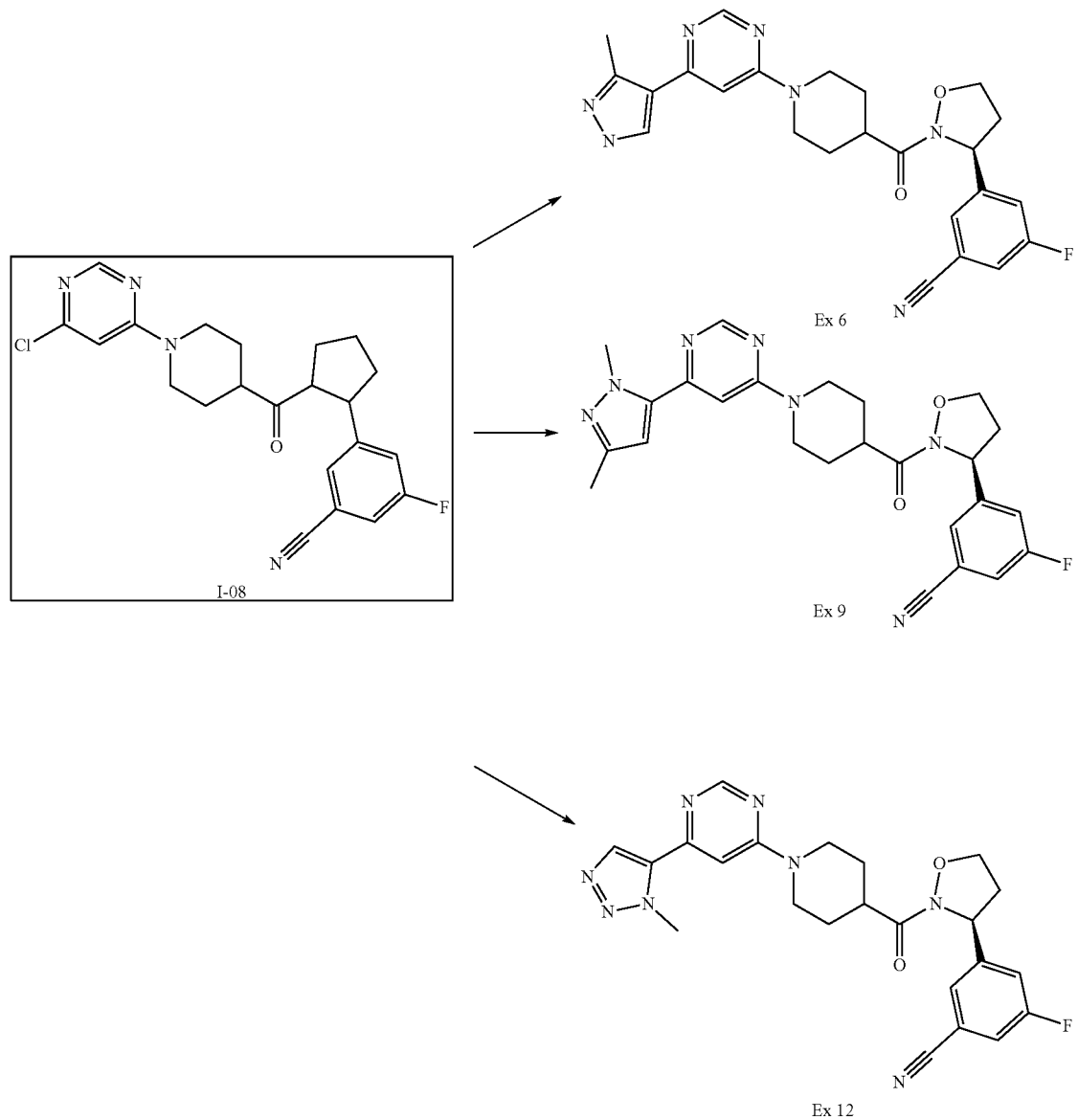
Scheme 6 (examples from Intermediate-09 and Intermediate-10)
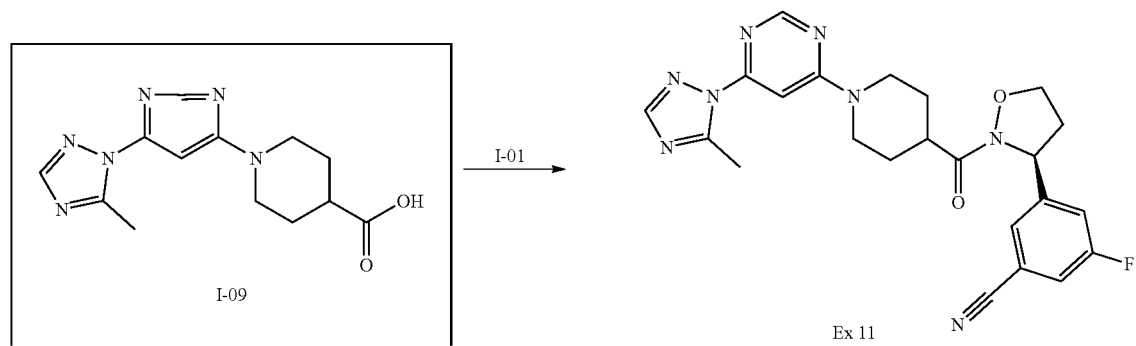

21
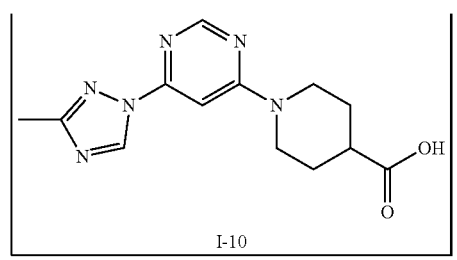
-continued
22
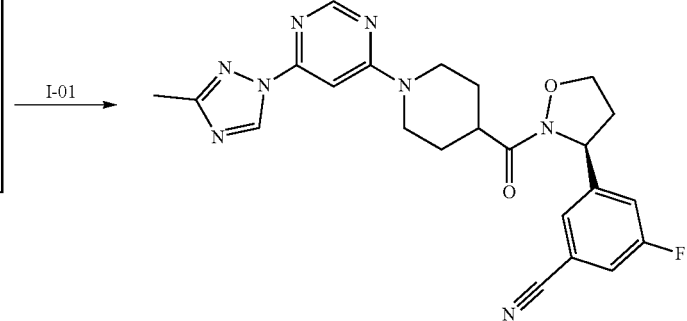
Ex 10

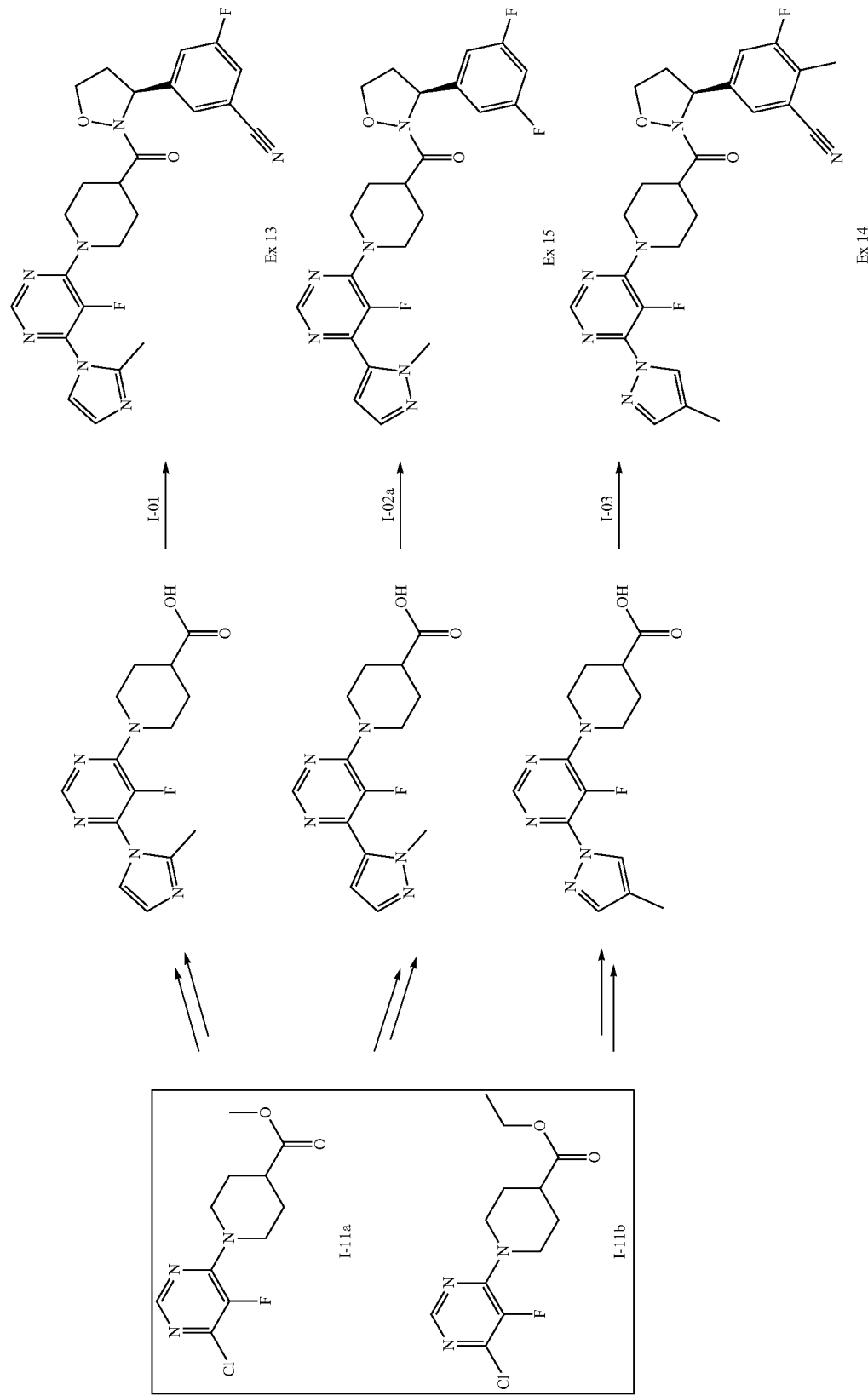
Scheme 7 (examples from Intermediate-11a and Intermediate-11b)

The synthesis of typical compounds described herein may be accomplished as described in the following examples. If available, reagents may be purchased commercially, e.g., from Sigma Aldrich or other chemical suppliers. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedure.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis, Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989). The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane, "DCM"), diethyl ether, methanol, pyridine and the like). Unless specified to the contrary, the solvents used in the reactions of the present disclosure are inert organic solvents, and the reactions are carried out under an inert gas, preferably argon.

Pharmaceutical Compositions

The compounds of the disclosure are usually administered in the form of pharmaceutical compositions. Thus, provided herein are also pharmaceutical compositions that contain one or more of the compounds of the disclosure or a pharmaceutically acceptable salt, tautomer, stereoisomer, mixture of stereoisomers, thereof and one or more pharmaceutically acceptable carriers, adjuvants and excipients.

Suitable pharmaceutically acceptable carriers may include, for example, inert solid diluents and fillers, diluents, including sterile aqueous solution and various organic solvents, permeation enhancers, solubilizers and adjuvants. Such compositions are prepared in a manner well known in the pharmaceutical arts.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous, or epidural injection as, for example, a sterile solution or suspension or sustained-release pharmaceutical composition; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically acceptable material, composition, or carrier, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the pharmaceutical composition and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical compositions. Examples of such pharmaceutical compositions include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino (NCH$_3$) and are, thus, capable of forming pharmaceutically acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration carrier or the dosage form manufacturing process or by separately reacting a purified compound of the disclosure in its free base form with a suitable organic or inorganic acid and isolating the salt thus formed during subsequent purification.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Pharmaceutical compositions of the present disclosure include those suitable for oral, nasal, topical (including buccal and sublingual), rectal, vaginal and/or parenteral administration. The pharmaceutical compositions may conveniently be presented in unit dosage form and may be prepared by any methods well known in the art of pharmacy. The amount of active compound which can be combined with a carrier material to produce a single dosage form will vary depending upon the host being treated, the particular mode of administration. The amount of active compound that can be combined with a carrier material to produce a single dosage form will generally be that amount of the compound which produces a therapeutic effect. Generally, this amount will range from about 1% to about 99% of active compound, preferably from about 5% to about 70%, most preferably from about 10% to about 30%. In certain embodiments, a pharmaceutical composition of the present disclosure comprises one or more of cyclodextrins, liposomes, micelle forming agents, e.g., bile acids and polymeric carriers, e.g., polyesters and polyanhydrides; and a compound of the present disclosure. In certain embodiments, an aforementioned pharmaceutical composition renders orally bioavailable a compound of the present disclosure. Methods of preparing these pharmaceutical compositions include the step of bringing into association a compound of the present disclosure with the carrier and, optionally, one or more accessory ingredients. In general, the pharmaceutical compositions are prepared by uniformly and intimately bringing into association a compound of the present disclosure with liquid carriers or finely divided solid carriers or both and then, if necessary, shaping the product. Pharmaceutical compositions of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active compound. A compound of the present disclosure may also be administered as a bolus, electuary or paste.

In solid dosage forms of the disclosure for oral administration (capsules, tablets, pills, dragees, powders, granules and the like), the active compound is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical formulating arts. They may also be formulated so as to provide slow or controlled release of the active compound therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active compound(s) only or preferentially, in a certain portion of the gastrointestinal tract, optionally, in a delayed manner. Examples of embedding compositions that can be used include polymeric substances and waxes. The active compound can also be in microencapsulated form, if appropriate, with one or more of the above-described excipients. Liquid dosage forms for oral administration of the compounds of the disclosure include pharmaceutically acceptable emulsions, microemulsions, solutions, suspensions, syrups and elixirs. In addition to the active compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Pharmaceutical compositions of the present disclosure which are suitable for vaginal administration also include pessaries, tampons, creams, gels, pastes, foams or sprays containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic pharmaceutical compositions, eye ointments, powders, solutions and the like, are also contemplated as being within the scope of this disclosure. Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the pharmaceutical composition isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil carrier.

Injectable depot forms are made by forming microencapsulated matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable pharmaceutical compositions are also prepared by entrapping the drug in liposomes or microemulsions, which are compatible with body tissue.

Methods of Treatment

In other embodiments, provided herein is a method of treating a receptor-interacting protein kinase 1-mediated disease or disorder. The method includes administering a therapeutically effective amount of a compound or pharmaceutical composition as described herein to a subject in need thereof. In some embodiments, the receptor-interacting protein kinase 1-mediated disease or disorder is trauma, ischemia, stroke, cardiac infarction, infection, Gaucher's disease, Krabbe disease, sepsis, systemic inflammatory response syndrome (SIRS), Parkinson's disease, Alzheimer's disease, amyotrophic lateral sclerosis, Huntington's disease, HIV-associated dementia, retinal degenerative disease, glaucoma, age-related macular degeneration, rheumatoid arthritis, non-communicable inflammatory skin diseases (ncISD) such as psoriasis or atopic dermatitis, psoriatic arthritis, or inflammatory bowel disease.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals.

Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor-interacting protein kinase 1 inhibitor, have demonstrated the effectiveness of receptor-interacting protein kinase 1 inhibition in protecting tissues from inflammatory bowel diseases (e.g., ulcerative colitis and Crohn's disease), non-communicable inflammatory skin diseases (ncISD) such as psoriasis or atopic dermatitis, retinal-detachment-induced photoreceptor necrosis, retinitis pigmentosa, cerulein-induced acute pancreatitis, and sepsis/systemic inflammatory response syndrome (SIRS), and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza or SARS-Coronavirus) and lysosomal storage diseases. The receptor-interacting protein kinase 1 inhibitors of the present disclosure are therefore suggesting that both RIPK1 kinase-driven inflammation and cell death are key contributing factors to systemic inflammatory response syndrome (SIRS). There is also rationale that vascular permeability and endothelial dysfunction contribute to SIRS/shock and lethality. The receptor-interacting protein kinase 1 inhibitors of the present disclosure are therefore useful for treating diseases and conditions mediated by receptor-interacting protein kinase 1, including but not limited to inflammatory diseases or disorders, necrotic cell diseases, neurodegenerative diseases, central nervous system (CNS) diseases, ocular diseases, infections, and malignancies. In certain embodiments, the receptor-interacting protein kinase 1 inhibitors described herein can inhibit inflammation, protect tissue or cell from damage or undesired cell death (e.g., necrosis or apoptosis), ameliorate symptoms, and improve immune response or neuronal function in a subject suffering from any of the prescribed diseases or conditions. Moreover, the compounds may be suitable for treatment of immune-mediated disease, such as but not limited to, allergic diseases, autoimmune diseases, and prevention of transplant rejection.

Provided herein are compounds and compositions for use in medicine. In certain embodiments, the compounds and compositions are for use in the treatment of a receptor-interacting protein kinase 1-mediated disease or disorder. Also provided is a method of treating a receptor-interacting protein kinase 1-mediated disease or disorder comprising administering a therapeutically effective amount of a compound or pharmaceutical composition disclosed herein to a subject in need thereof. In certain embodiments, the disease or disorder is an inflammatory disease associated with A20 SNPs.

Various specific diseases and disorders are described below. In certain embodiments, the disease or disorder is necrotizing enterocolitis, tuberous sclerosis, Tangier's Disease, Wohlman's Syndrome, inflammatory bowel disease, Crohn's disease, ulcerative colitis, non-communicable inflammatory skin diseases (ncISD) such as psoriasis or atopic dermatitis, retinal detachment, retinitis pigmentosa, macular degeneration, pancreatitis (e.g., acute pancreatitis), interface dermatitis (e.g. cutaneous lupus erythematosus, lichen planus, lichen planopillaris, toxic epidermal necrolysis (TEN), Stevens-Johnson-Syndrome, Graft versus Host Disease (GvHD), alopecia arreata, vitiligo), atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome (SIRS), cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, bacterial infection, staphylococcus infection, mycobacterium infection, retinitis pigmentosa, influenza, severe acute respiratory syndrome (SARS), middle east respiratory syndrome (MERS), acute respiratory response syndrome (ARDS), transplant rejection, burns or hypoxia. In certain embodiments, the disease or disorder is trauma, ischemia, stroke, cardiac infarction, infection, lysosomal storage disease, Niemann-Pick disease, Gaucher's disease, Krabbe disease, sepsis, systemic inflammatory response syndrome (SIRS), Parkinson's disease, Alzheimer's disease, amyotrophic lateral sclerosis (ALS/Lou Gehrig's Disease), Huntington's disease, HIV-associated dementia, encephalopathy, retinal degenerative disease, glaucoma, age-related macular degeneration, rheumatoid arthritis, non-communicable inflammatory skin diseases (ncISD) such as psoriasis or atopic dermatitis, psoriatic arthritis or inflammatory bowel disease.

In certain embodiments, the disease is necrotizing enterocolitis, tuberous sclerosis, Tangier's Disease, Wohlman's Syndrome, inflammatory bowel disease, Crohn's disease, ulcerative colitis, psoriasis, retinal detachment, retinitis pigmentosa, macular degeneration, pancreatitis (e.g., acute pancreatitis), atopic dermatitis, rheumatoid arthritis, psoriatic arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia, ischemia reperfusion injury of solid organs, cerebral ischemia, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, infection, bacterial infection, staphylococcus infection, mycobacterium infection, influenza, transplant rejection, burns, hypoxia, trauma, stroke, cardiac infarction, lysosomal storage disease, Niemann-Pick disease, Gaucher's disease, Krabbe disease, amyotrophic lateral sclerosis (ALS/Lou Gehrig's Disease), HIV-associated dementia, encephalopathy, retinal degenerative disease, glaucoma, age-related macular degeneration, Friedreich's ataxia, Lewy body disease, diabetic neuropathy, polyglutamine (polyQ) diseases, Fahr disease, Menke's disease, Wilson's disease, a prion disorder, atherosclerosis, Guillain-Barre syndrome, chronic inflammatory demyelinating polyneuropathy, major depressive disorder, bipolar disorder, delirium, post-operative cognitive impairment, autism, schizophrenia, hidradenitis suppurativa or or incontinentia pigmenti.

In certain embodiments, the disease or disorder is Alzheimer's disease, ALS, Friedreich's ataxia, Huntington's disease, Lewy body disease, Parkinson's disease, Huntington's disease, multiple sclerosis, diabetic neuropathy, polyglutamine (polyQ) diseases, stroke, Fahr disease, Menke's disease, Wilson's disease, cerebral ischemia, lysosomal storage disease or a prion disorder. In certain embodiments, the disease is ALS. In certain embodiments, the disease is Alzheimer's disease. In certain embodiments, the disease is lysosomal storage disease. In certain embodiments, the disease is Parkinson's disease. In certain embodiments the disorder is an ischemic disease of organs including but not limited to brain, heart, kidney and liver. In some different embodiments, the disorder is an ocular disorder such as retinal degenerative disease, glaucoma or age-related macular degeneration. In some different embodiments, the disorder is a central nervous system (CNS) disorder.

In certain embodiments, provided is a method of treating rheumatoid arthritis (see Lawlor K E, et al., Nat Commun. 2015, 6282; Lee S H, et al., Sci Rep., 7, 2017, 10133), systemic onset juvenile idiopathic arthritis (SoJIA), spondyloarthritis, osteoarthritis, non-communicable inflammatory skin diseases (ncISD) such as psoriasis or atopic dermatitis, Crohn's disease, ulcerative colitis, or multiple sclerosis, comprising administering a therapeutically effective amount of a compound as provided herein to a subject in need thereof. In certain embodiments, provided is a method of treating autoimmune hepatitis, atherosclerosis, neutrophilic dermatoses, or a rare disease driven by A20, NEMO, and/or LUBAC mutations, comprising administering a therapeutically effective amount of a compound of the disclosure to a subject in need thereof.

In certain embodiments, the compounds and compositions are useful for treating non-communicable inflammatory skin diseases (ncISD) such as psoriasis or atopic dermatitis.

In certain embodiments, the disorder is an inflammatory disease of the intestines such as Crohn's disease or ulcerative colitis (both generally known together as inflammatory bowel disease, IBD). While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Dondelinger et al, Molecular Cell 60, 1 Oct. 2015, Pages 63-76 reports that the molecular mechanism regulating the contribution of RIPK1 to cell death is far less understood. Shown is that the IKK complex, including NEMO/IKKγ, negatively regulates RIPK1 activation at TNFR1 complex I by phosphorylation and protects cells from RIPK1 kinase-dependent death, independent of its function in NF-κB activation. Dirk A. Ridder et al, J Exp Med (2015) 212 (10): 1529-1549 shows that deleting NEMO or Tak1 in brain endothelial cells in mice leads to a phenotype reminiscent of neurological symptoms associated with IP Smahi A, et al. Genomic rearrangement in NEMO impairs NF-κB activation and is a cause of incontinentia pigmenti. The International Incontinentia Pigmenti (IP) Consortium. Nature. 2000; 405:466-72.

Also an overview over IP is given in Fusco et al. Orphanet Journal of Rare Diseases 2014, 9:93.

Incontinentia pigmenti (IP) is a genetic condition that affects the skin and other body systems. Skin symptoms change with time and begin with a blistering rash in infancy, followed by wart-like skin growths. The growths become swirled grey or brown patches in childhood, and then swirled light patches in adulthood. Other signs and symptoms may include hair loss, small or missing teeth, eye abnormalities that can lead to vision loss, and lined or pitted nails. Most people with IP have normal intelligence, but some have developmental delay, intellectual disability, seizures, and/or other neurological problems. IP is caused by mutations in the IKBKG gene and is inherited in an X-linked dominant manner.

In another embodiment, the compounds of formula I and compositions are useful for treating Incontinentia pigmenti.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), non-communicable inflammatory skin diseases (ncISD) such as psoriasis or atopic dermatitis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis.

In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis. In certain embodiments, the compounds and compositions are useful for treating rheumatoid arthritis (RA). In certain embodiments, the compounds and compositions are useful for treating ulcerative colitis. In certain embodiments, the compounds and compositions are useful for treating non-communicable inflammatory skin diseases (ncISD) such as psoriasis or atopic dermatitis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity.

Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

In another embodiment the receptor interacting protein kinase 1 inhibitors described herein may be used to treat inflammatory diseases and disorders like rheumatoid arthritis (RA), psoriasis, inflammatory bowel disease (IBD) like Crohn's disease or ulcerative colitis.

In another embodiment the receptor interacting protein kinase 1 inhibitors described herein may be used to treat Interface dermatitis like cutaneous lupus erythematosus (CLE), Lichen planus (LP), toxic epidermal necrolysis (TEN) or Stevens-Johnson syndrome (SJS).

In another embodiment the receptor interacting protein kinase 1 inhibitors described herein may be used to treat hyperinflammation during viral infection like corona virus disease-19 (COVID-19), acute respiratory distress syndrome (ARDS), systemic inflammatory response syndrome (SIRS).

In another embodiment the receptor interacting protein kinase 1 inhibitors described herein may be used to treat corona virus disease-19 (COVID-19).

In another embodiment the receptor interacting protein kinase 1 inhibitors described herein may be used to treat respiratory diseases like Influenza (e.g. swine flu, H7N9), severe acute respiratory syndrome (SARS), Middle East Respiratory Syndrome (MERS), Respiratory-Syncytial-Virus (RSV) or bronchiolitis).

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, systemic inflammatory response syndrome (SIRS), Parkinson's disease, Alzheimer's disease, amyotrophic lateral sclerosis, Huntington's disease, HIV-associated dementia, retinal degenerative disease, glaucoma, age-related macular degeneration, rheumatoid arthritis, non-communicable inflammatory skin diseases (ncISD) such as psoriasis or atopic dermatitis, psoriatic arthritis or inflammatory bowel disease.

The necrotic cell diseases can be acute diseases such as trauma, ischemia, stroke, cardiac infarction, anthrax lethal toxin induced septic shock, sepsis, systemic respiratory response syndrome (SIRS), cell death induced by LPS and HIV induced T-cell death leading to immunodeficiency. In certain embodiments the disorder is an ischemic disease of organs including but not limited to brain, heart, kidney and liver.

The necrotic cell diseases also include chronic neurodegenerative diseases, such as Parkinson's disease, Huntington's disease, amyotrophic lateral sclerosis, Alzheimer's disease, infectious encephalopathies, dementia such as HIV associated dementi. In some different embodiments, the disorder is an ocular disorder such as retinal degenerative disease, glaucoma or age-related macular degeneration. In some different embodiments, the disorder is a central nervous system (CNS) disorder.

Neurodegenerative and CNS Diseases

The receptor-interacting protein kinase 1 inhibitors described herein may also be used to treat neurodegenerative diseases. Neurodegenerative diseases can affect many of the body's activities, such as balance, movement, talking, breathing, and heart function. Neurodegenerative diseases can be genetic or caused by medical conditions such as alcoholism, tumors, strokes, toxins, chemicals, and viruses. Non-limiting examples of neurodegenerative diseases include Alzheimer's disease, amyotrophic lateral sclerosis (ALS), Friedreich's ataxia, Huntington's disease, Lewy body disease, Parkinson's disease, and spinal muscular atrophy. In certain embodiments, neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease, and spinal muscular atrophy.

In certain embodiments, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor-interacting protein kinase 1 inhibitors described herein can be used to preserve neuron viability and promote axon growth and nerve functions within the central nervous system (CNS). Accordingly, the compounds may be used to reduce or even reverse the loss of cognitive, motor, and sensory functions associated with a CNS disease or disorder, by preserving neuron viability and/or promoting axon regeneration and/or nerve functions.

The receptor-interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron, and a midbrain neuron. The receptor interacting protein kinase 1 inhibitors described herein can be used in a method for promoting nerve function or preserving the viability following injury to a CNS neuron. In another embodiments, these compounds can be used to promote regeneration of an axon in a CNS neuron that is degenerated in the CNS disease or disorder. The RIP receptor-interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

Non-limiting examples of CNS diseases or disorders include brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabeticneuropathy, polyglutamine (polyQ) diseases, stroke, Fahr disease, Menke's disease, Wilson's disease, cerebral ischemia, and a prion disorder. In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heartbeat and blood pressure, e.g., an injury to or aneurysm in the brain stem. In certain embodiments, the CNS disease or disorder affects a subject's cognitive ability. In certain embodiments, the CNS disease or disorder affects a subject's movement and/or strength. In certain embodiments, the CNS disease or disorder affects a subject's coordination.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasaldegeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Non-limiting examples of neurodegenerative diseases include Alzheimer's disease, lysosomal storage diseases, amyotrophic lateral sclerosis (ALS), Friedreich's ataxia, Huntington's disease, Lewy body disease, Parkinson's disease, and spinal muscular atrophy.

In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS). In certain embodiments, the compounds and compositions of the present disclosure are useful for treating lysosomal storage diseases.

In certain embodiments, the disorder is a brain disorders, such as, but not limited to, Alzheimer's disease, ALS, frontotemporal dementias, vascular dementia, Huntington's disease, Parkinson's disease, Lewy Body dementia, Progressive Supranuclear Palsy, multiple sclerosis, neuromyelitis optica, ischemic brain damage (stroke), hypoxic brain damage, traumatic brain injury, spinal cord injury, sepsis-induced brain damage, CNS infections, CNS abscesses, glioblastoma multiforme, epilepsy, neuropathic pain, major depression, bipolar depression, schizophrenia, autism, Niemann-Pick disease, neuro-Behçet's disease.

In certain embodiments, provided is a method of treating a CNS disease or disorder, comprising administering a therapeutically effective amount of a compound as provided herein to a subject in need thereof. In certain embodiments, the disease or disorder is Alzheimer's disease or amyotrophic lateral sclerosis (ALS).

Ocular Conditions

The receptor-interacting protein kinase 1 inhibitors described herein can also be used to treat ocular conditions, for example to reduce or prevent the loss of photoreceptor and/or retinal pigment epithelial cell viability.

In certain embodiments, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. AMD may be the neovascular or the dry form of AMD. Retinal detachment may be arhegmatogenous, a serous, and a tractional retinal detachment. In certain embodiments, the ocular condition may be geographic atrophy, glaucoma, or another ischemic eye disease. In certain embodiments, the disclosure provides a method of preserving the viability of retinal pigment epithelial (RPE) cells within the retina of a subject with an ocular condition with administration of a compound of the present disclosure. The subject being treated may have a loss of retinal pigment epithelial cells in the retina of the eye with the condition and the ocular condition may be age-related macular degeneration (AMD), BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), or another uveitis disorder. In certain embodiments, the method comprises administering to the eye of the subject an effective amount of a compound or composition described herein, thereby preserving the viability of the retinal pigment epithelial cells. Provided in another embodiment is a method of preserving the viability of photoreceptor cells disposed within a retina of a subject with age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. Therefore, in certain embodiments, the method comprises administering to the eye an effective amount of a compound or composition described herein, thereby preserving the viability of the photoreceptor cells disposed within the retina of the subject with a condition. Provided in another embodiment is a method of preserving the viability of photoreceptor cells disposed within a retina of a mammalian eye following retinal detachment. The retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma. In certain embodiments, the method comprises administering a compound or composition described herein to the eye in which a region of the retina has been detached in amounts sufficient to preserve the viability of photoreceptor cells disposed within the region of the detached retina. Provided in another embodiment is a method of preserving visual function of an eye of a subject with age-related macular degeneration (AMD), retinosis pigmentosa (RP), macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity, wherein a symptom of the ocular condition is the loss of photoreceptor cells viability in the retina of the eye, wherein the method comprises treating the subject with a compound or composition described herein to the subject. In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments, provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

Non-limiting examples of symptoms associated with the ocular conditions include the loss of retinal ganglion cell viability in the retina of the eye, glaucoma, optic nerve injury, optic neuritis, optic neuropathies, diabetic retinopathy, central retinal artery occlusion, and central retinal vein occlusion. The compounds described herein may also be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial opticneuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with glaucoma, optic nerve injury, optic neuropathies, diabetic retinopathy, central retinal artery occlusion, or central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglioncells disposed within the region of the affected retina. The preserved retinal ganglion cell is capable of supporting axonal regeneration, linear ubiquitin chain assembly complex (LUBAC) deficiency syndrome, hematological and solid organ malignancies, bacterial infections and viral infections (e.g., tuberculosis and influenza or SARS-Coronavirus) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease.

In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof. In another embodiment, the present disclosure provides a method of inhibiting receptor-interacting protein kinase 1. The method includes contacting the receptor-interacting protein kinase 1 with an effective amount of a compound of the disclosure. Inhibiting the receptor-interacting protein kinase 1 generally include contacting the receptor-interacting protein kinase 1 with an amount of the compound of the disclosure sufficient to reduce the activity of the receptor-interacting protein kinase 1 as compared to the receptor-interacting proteinkinase 1 activity in the absence of the compound. For example, contacting the receptor-interacting protein kinase 1 with the compound of the disclosure can result in from about 1% to about 99% receptor-interacting protein kinase 1 inhibition (i.e., the activity of the inhibited enzyme ranges from 99% to 1% of the enzyme activity in the absence of the compound of the disclosure). The level of receptor-interacting protein kinase 1 inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of receptor-interacting protein kinase 1 inhibition can range from about 5% to about 95%, or from about 10% to about 90%, or from about 20% to about 80%, or from about 30% to about 70%, or from about 40% to about 60%. In some embodiments, contacting the receptor-interacting protein kinase 1 with a compound of the disclosure will result in complete (i.e., 100%) inhibition.

Combination Therapy

In certain embodiments, the compounds of the disclosure may be administered in combination with at least one other therapeutically active agent. The two or more agents can be coadministered, coformulated, or administered separately. In certain embodiments, the other therapeutically active agent is selected from a thrombolytic agent, a tissue plasminogen activator, an anticoagulant, a platelet aggregation inhibitor, an antimicrobial agent (an antibiotic, a broad-spectrum antibiotic, a lactam, an antimycobacterial agent, a bactericidal antibiotic, anti-MRSA therapy), a long acting beta agonist, a combination of an inhaled corticosteroid and a long acting beta agonist, a short acting beta agonist, a leukotriene modifier, an anti-IgE, a methylxanthine bronchodilator, a mast cell inhibitor, a protein tyrosine kinase inhibitor, a CRTH2/D prostanoid receptor antagonist, an epinephrine inhalation aerosol, a phosphodiesterase inhibitor, a combination of a phosphodiesterase-3 inhibitor and a phosphodiesterase-4 inhibitor, a long-acting inhaled anticholinergic, a muscarinic antagonist, a long-acting muscarinic antagonist, a low dose steroid, an inhaled corticosteroid, an oral corticosteroid, a topical corticosteroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor, a cystic fibrosis transmembrane conductance regulator potentiator, a mucolytic agent, pancreatic enzymes, a bronchodilator, an opthalmalic intravitreal injection, an anti-vascular endothelial growth factor inhibitor, a ciliary neurotrophic growth factor agent, a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, inactivated influenza vaccine, a ciliary neurotrophic growth factor, a gene transfer agent, a topical immunomodulator, calcineurin inhibitor, an interferon gamma, an antihistamine, a monoclonal antibody, a polyclonal anti-Tcell antibody, an anti-thymocyte gamma globulin-equine antibody, an antithymocyte globulin-rabbit antibody, an anti-CD40 antagonist, a JAK inhibitor, and an anti-TCR murine mAb.

Exemplary other therapeutically active agents include heparin, coumadin, clopidrogel, dipyridamole, ticlopidine HCL, eptifibatide, aspirin, vacomycin, ceferime, a combination of piperacillin and tazobactam, imipenem, meropenem, doripenem, ciprofloxacin, levofloxacin, ofloxacin, moxifloxacin, hydrocortisone, vedolizumab, alicaforsen, remestemcel-L, ixekizumab, tildrakizumab, secukinumab, chlorhexidine, doxycycline, minocycline, fluticasone (fluticasone proprionate, fluticasone furoate), beclomethasone dipropionate, budesonide, trimcinolone acetonide, flunisolide, mometasone fuorate, ciclesonide, arformoterol tartrate, formoterol fumarate, salmeterol xinafoate, albuterol (albuterol sulfate), levalbuterol tartrate, ipratropium bromide, montelukast sodium, zafirlukast, zileuton, omalizumab, theophylline, cromulyn sodium, nedocromil sodium, masitinib, AMG 853, indacaterol, E004, reslizumab, salbutamol, tiotropium bromide, VR506, lebrikizumab, RPL554, aflibercept, umeclidinium, indacterol maleate, aclidinium bromide, roflumilast, SCH527123, glycoprronium bromide, olodaterol, a combination of fluticasone furoate and vilanterol, a combination of fluticasone propionate and salmeterol, a combination of fluticasone furoate and fluticasone proprionate, a combination of fluticasone propionate and eformoterol fumarate dihydrate, a combination of formoterol and budesonide, a combination of beclomethasone dipropionate and formoterol, a combination of mometasone furoate and formoterol fumarate dihydrate, a combination of umeclidinium and vilanterol, a combination of ipratropium bromide and albuterol sulfate, a combination of glycopyrronium bromide and indacaterol maleate, a combination of glycopyrrolate and formoterol fumarate, a combination of aclidinium and formoterol, isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, delamanid, imatinib, ARG201, tocilizumab, muromonab-CD3, basiliximab, daclizumab, rituximab, prednisolone, anti-thymocyte globulin, FK506 (tacrolimus), methotrexate, cyclosporine, sirolimus, everolimus, mycophenolate sodium, mycophenolate mofetil, cyclophosphamide, azathioprine, thalidomide, chlorambucil, nifedipine, nicardipine, nitroglycerin, lisinopril, diltaizem, fluoxetine, bosentan, epoprostenol, colchicine, para-aminobenzoic acid, dimethyl sulfoxide, D-penicillamine, interferon alpha, interferon gamma (INF-g), omeprazole, metoclopramide, lansoprazole, esomeprazole, pantoprazole, rabeprazole, imatinib, belimumab, ARG201, tocilizumab, ivacaftor, dornase alpha, pancrelipase, tobramycin, aztreonam, colistimethate sodium, cefadroxil monohydrate, cefazolin, cephalexin, cefazolin, moxifloxacin, levofloxacin, gemifloxacin, azithromycin, gentamicin, ceftazidime, a combination of trimethoprim and sulfamethoxazole, chloramphenicol, a combination of ivacftor and lumacaftor, ataluren, NT-501-CNTF, a gene transfer agent encoding myosin VIIA (MY07A), ranibizumab, pegaptanib sodium, NT501, humanized sphingomab, bevacizumab, oseltamivir, zanamivir, rimantadine, amantadine, nafcillin, sulfamethoxazolem, trimethoprim, sulfasalazine, acetyl sulfisoxazole, vancomycin, muromonab-CD3, ASKP-1240, ASPO15K, TOL101, pimecrolimus, hydrocortizone, betamethasone, flurandrenolide, triamcinolone, fluocinonide, clobetasol, hydrocortisone, methylprednisolone, prednisolone, a recombinant synthetic type I interferon, interferon alpha-2a, interferon alpha-2b, hydroxyzine, diphenhydramine, flucloxacillin, dicloxacillin, and erythromycin.

A compound of the disclosure may be administered in combination with other anti-inflammatory agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL1 7 biologics, anti-CD22, anti-integrin agents, anti-IFNa, anti-CD20 or CD4 biologics and other cytokine inhibitors or biologics to T-cell or B-cell receptors or interleukins.

In the treatment of ALS, a compound of the disclosure may be administered in combination with riluzole.

In the treatment of Parkinson's disease, a compound of the disclosure may be administered in combination with levodopa, carbodopa or a combination thereof, pramipexole, ropinirole, rotigotine, selegiline, rasagiline, entacapone, tolcapone, benztropine, trihexyphenidyl, or amantadine.

In the treatment of Alzheimer's disease, a compound of the disclosure may be administered in combination with donepezil, galantamine, memantine, rivastigmine, anti-ABeta (amyloid beta) therapies including aducanumab, crenezumab, solanezumab, and gantenerumab, small molecule inhibitors of BACE1 including verubecestat, AZD3293 (LY3314814), elenbecestat (E2609), LY2886721, PF-05297909, JNJ-54861911, TAK-070, VTP-37948, HPP854, CTS-21166, or anti-tau therapies such as LMTM (leuco-methylthioninium-bis (Hydromethanesulfonate®).

In the treatment of rheumatoid arthritis, a compound of the disclosure may be administered in combination with ibuprofen, naproxen, prednisone, methotrexate, leflunomide, hydroxychloroquine, sulfasalazine, abatacept, adalimumab, anakinra, certolizumab, etanercept, golimumab, infliximab, rituximab, tocilizumab or tofacitinib.

In the treatment of CVA, a compound of the disclosure may be administered to in combination with a thrombolytic agent (such as tissue plasminogen activator), an anticoagulant (such as heparin, coumadin, clopidrogel, and a platelet aggregation inhibitor (such as dipyridamole, ticlopidine HCL, eptifibatide, and/or aspirin).

In the treatment of SIRS, a compound of the disclosure may be administered in combination with a broad-spectrum antibiotic (such as vacomycin) or other anti-MRSA therapy (cefeprime, piperacillin/tazobactam, carbapenem (imipenem, meropenem, doripenem), quinolones (ciprofloxacin, levofloxacin, ofloxacin, moxifloxacin, etc.), and low dose steroids such as hydrocortisones.

In the treatment of inflammatory bowel disease (particularly, Crohn's disease and/or ulcerative colitis), a compound of any formula described herein, may be administered in combination with vedolizumab, alicaforsen, or remestemcel-L. Specifically, in the treatment of inflammatory bowel disease (particularly, Crohn's disease and/or ulcerative colitis), a compound of the disclosure may be administered in combination with alicaforsen, or remestemcel-L.

In the treatment of non-communicable inflammatory skin diseases (ncISD) such as psoriasis or atopic dermatitis, a compound of the disclosure may be administered in combination with ixekizumab, tildrakizumab (MK-3222), or secukinumab (AIN457).

Specifically, in the treatment of non-communicable inflammatory skin diseases (ncISD) such as psoriasis or atopic dermatitis, a compound of the disclosure may be administered in combination with ixekizumab, or tildrakizumab (MK-3222). In the treatment of periodonitis, a compound of any formula described herein may be administered in combination with an antimicrobial agent, (such as chlorhexidine or an antibiotic (such as doxycycline or minocycline.

In the treatment of asthma, a compound of any formula described herein may be administered in combination with an inhaled corticosteroid ((ICS) such as fluticasone proprionate, beclomethasone dipropionate, budesonide (Pulmicort), triamcinolone acetonide, flunisolide, mometasone fuorate, or Ciclesonide, a long acting beta agonist ((LABA) such as formoterol fumarate, salmeterol xinafoate), a combination of an ICS and LABA (such as fluticasone furoate and vilanterol, formoterol/budesonide inhalation, beclomethasone dipropionate/formoterol, and fluticasone propionate/salmeterol, a short acting beta agonist ((SABA) such as albuterol sulfate, levalbuterol tartrate, ipratropium bromide/albuterol, ipratropium bromide, a leukotriene modifier (such as montelukast sodium, zafirlukast, or zileuton, and anti-IgE (such as omalizumab), a methylxanthine bronchodilator (such as theophylline, a mast cell inhibitor (such as cromulyn sodium and nedocromil sodium, a long-acting muscarinic antagonist ((LAMA) such as mometasone furoate/formoterol fumarate dihydrate).

Other agents that may be suitable for use in combination therapy in the treatment of asthma include a protein tyrosine kinase inhibitor (masitinib), CRTH2/D-prostanoid receptor antagonist (AMG 853), indacaterol, an epinephrine inhalation aerosol (E004), fluticasone furoate/fluticasone propionate, vilanterol inhalation/fluticasone furoate powder, fluticasone propionate/eformoterol fumarate dihydrate, reslizumab, salbutamol dry-powder inhalation, tiotropium bromide, formoterol/budesonide, fluticasone furoate, Vectura's VR506, lebrikizumab (RG3637), a combination phosphodiesterase (PDE)-3 and (PDE)-4 inhibitor (RPL554).

In the treatment of COPD, a compound of any formula described herein, may be administered in combination with a LABA (such as salmeterol xinafoate, umeclidinium/vilanterol, umeclidinium, arformoterol tartrate, formoterol fumarate inhalation powder, indacterol maleate, or fluticasone propionate/eformoterol fumarate dehydrate, a long-acting inhaled anticholinergic (or muscarinic antagonist, such as tiotropium bromide, and aclidinium bromide, a phosphodiesterase (PDE-r) inhibitor (such as roflumilast, Daliresp), a combination ICS/LABA (such as fluticasone furoate and vilanterol, fluticasone propionate/salmeterol, budesonide/formoterol, mometasone/formoterol, ipratropium bromide/albuterol sulfate, albuterol/ipratropium, a SABA (such as ipratropium bromide, and albuterol sulfate, and an ICS (such as budesonide and fluticasone propionate, beclomethasone dipropionate.

Other agents that may be suitable for use in combination therapy in the treatment of COPD include SCH527123 (a CXCR2 antagonist), glycoprronium bromide (NVA237), glycopyrronium bromide and indacaterol maleate (QVA149), glycopyrrolate and formoterol fumarate (PT003), indacaterol maleate (QVA149), olodaterol, tiotropium/olodaterol, and aclidinium/formoterol inhalation.

In the treatment of a mycobacterium infection (tuberculosis), a compound of any formula described herein may be administered in combination with an antimycobacterial agent (such as isoniazid (INH), ehambutol, rifampin, and pyrazinamide a bactericidal antibiotic (such as rifabutin or rifapentine, an aminoglycoside (capreomycin), a fluorquinolone (levofloxacin, moxifloxicin, ofloxacin), thioamide (ehionamide), cyclosporine, para-aminosalicyclic acid, cycloserine, kanamycin, streptomycin, viomycin, capreomycin, bedaquiline fumarate, oxazolidinone, or delamanid (OPC-67683).

Specifically, in the treatment of a mycobacterium infection (tuberculosis), a compound of the disclosure may be administered in combination with an antimycobacterial agent (such as isoniazid (INH), ehambutol, rifampin, and pyrazinamide, a bactericidal antibiotic (such as rifabutin or rifapentine, an aminoglycoside (Capreomycin), a fluorquinolone (levofloxacin, moxifloxicin, ofloxacin), thioamide (ehionamide), cycloserine, kanamycin, streptomycin, viomycin, capreomycin, bedaquiline fumarate, oxazolidinone, or delamanid (OPC-67683).

In the treatment of systemic scleroderma, a compound of any formula described herein may be administered in combination with an oral corticosteroid (such as prednisolone, an immunosuppressive agent (such as methotrexate, cyclosporine, anti-thymocyte globulin, mycophenolate mofetil, cyclophosphamide, FK506 (tacrolimus), thalidomide, chlorambucil, azathioprine, a calcium channel blocker (such as nifedipine or nicardipine, a topical emollient (nitroglycerin ointment), an ACE inhibitor (such as lisinopril), a serotonin reuptake inhibitor (such as fluoxetine, an endothelin-I receptor inhibitor (such as bosentan or epoprostenol an anti-fibrotic agent (such as colchicines, para-aminobenzoic acid (PABA), dimethyl sulfoxide (DMSO), and D-penicillamine, interferon alpha and interferon gamma (INF-g), a proton-pump Inhibitor (such as omeprazole, metoclopramide, ansoprazole, esomeprazole, pantoprazole, rabeprazole or imatinib, ARG201 (arGentis Pharmaceutical), belimumab, tocilizumab.

Specifically, in the treatment of systemic scleroderma, a compound of any formula described herein may be administered in combination with an oral corticosteroid (such as prednisolone), anti-thymocyte globulin, FK506 (tacrolimus), thalidomide, chlorambucil, a calcium channel blocker (such as nifedipine or nicardipine, a topical emollient (nitroglycerin ointment), an ACE inhibitor (such as lisinopril), diltaizem, a serotonin reuptake inhibitor (such as fluoxetine), an endothelin-I receptor inhibitor (such as bosentan or epoprostenol), an anti-fibrotic agent (such as colchicines (Colcrys), para-aminobenzoic acid (PABA), dimethyl sulfoxide (DMSO), and D-penicillamine, interferon alpha and interferon gamma (INF-g), a proton-pump Inhibitor (such as omeprazole, metoclopramide, ansoprazole, esomeprazole, pantoprazole, rabeprazole or imatinib, ARG201 (arGentis Pharmaceutical), or tocilizumab.

In the treatment of cystic fibrosis, a compound of the disclosure may be administered in combination with a cystic fibrosis transmembrane conductance regulator (CFTR) potentiator (ivacftor, a mucolytic agent (such as dornase alpha), pancreatic enzymes (such as Pancrelipase), a bronchodilator (such as albuterol), an antibiotic (including inhaled, oral or parenteral, such as tobramycin solution for inhalation, aztreonam inhalation, colistimethate sodium, cephalosporins (cefadroxil monohydrate, cefazolin, cephalexin, cefazolin, fluoroquinolones (moxifloxacin, levofloxacin, gemifloxacin, etc), azithromycin, gentamicin, piperacillin/tazobacam, cephalexin, ceftazidime, ciprofloxin, trimethoprim/sulfamethoxazole, or ivacftor/lumacaftor (VX-809), ataluren, or with tiopropium bromide as add on to standard therapy.

In the treatment of retinitis pigmentosa, a compound of the disclosure may be administered in combination with a ciliary neurotrophic growth factor (NT-501-CNTF) or gene transfer agent, UshStat.

In the treatment of macular degeneration, a compound of any formula described herein, may be administered in combination with opthalmalic intravitreal injections (afibercept) or with an anti-vascular endothelial growth factor (VEGF) inhibitor (such as ranibizumab or pegaptanib sodium, a ciliary neurotrophic growth factor agent (NT501), iSONEP, or bevacizumab.

In the treatment of influenza, a compound of the disclosure may be administered in combination with a trivalent (IIV3) inactivated influenza vaccine (such as Afluria, Fluarix, Flucelvax, FluLaval, Fluvirin, Fluzone), a quadrivalent (IIV4) inactivated influenza vaccine (such as Fluarix Quadrivalent, Flulaval Quadrivalent, Fluzone Quadrivalent), a trivalent recombinant influenza vaccine (such as FluBlok), a quadrivalent live attenuated influenza vaccine (such as FluMist Quadrivalent), an antiviral agent (such as oseltamivir, zanamivir, rimantadine, or amantadine), or Fluad, Fludase, FluNhance, Preflucel, or VaxiGrip.

In the treatment of a staphylococcus infection, a compound of any formula described herein may be administered in combination with an antibiotic (such as a-Lactam cephalosporin, nafcillin, a sulfonamide (sulfamethoxazole and trimethoprim, sulfasalazine, acetyl sulfisoxazole), or vancomycin.

In the treatment of transplant rejection, a compound of any formula described herein may be administered in combination with a high-dose corticosteroid (such as prednisone, methylprednisolone, a calcineurin inhibitor (such as cyclosporine), tacrolimus, an mTor inhibitor (such as sirolimus or everolimus, an anti-proliferative agent (such as azathioprine, mycophenolate mofetil, or mycophenolate sodium, a monoclonal antibody (such as muromonab-CD3, an interleukine-2 receptor antagonist, daclizumab, or rituximab, a polyclonal anti-T-cell antibody (such as anti-thymocyte gamma globulin-equine, or antithymocyte globulin-rabbit, an anti-CD40 antagonist (ASKP-1240), a JAK inhibitor (ASP015K), or an anti-TCR murine mAb (TOL101).

Specifically, in the treatment of transplant rejection, a compound of any formula described herein may be administered in combination with a monoclonal antibody (such as muromonab-CD3, a polyclonal anti-T-cell antibody (such as anti-thymocyte gamma globulin-equine, or antithymocyte globulin-rabbit, an anti-CD40 antagonist (ASKP-1240), a JAK inhibitor (ASP015K), or an anti-TCR murine mAb (TOL101).

In the treatment of atopic dermatitis, a compound of any formula described herein may be administered in combination with a topical immunomodulator or calcineurin inhibitor (such as pimecrolimus or tacrolimus ointment, a topical corticosteroid (such as hydrocortizone, betamethasone, flurandrenolide, fluticasone, triamcinolone, fluocinonide, and clobetasol, an oral corticosteroid (such as hydrocortisone, methylprednisolone, or prednisolone, an immunosuppressant (such as cyclosporine or interferon gamma (Alferon N, Infergen, Intron A, Roferon-A®), an antihistamine (for itching such as Atarax, Vistaril, Benadryl), an antibiotic (such as penicillin derivatives flucloxacillin or dicloxacillin, erythromycin, a nonsteroidal immunosuppressive agent (such as azathioprine), methotrexate, cyclosporine, or mycophenolate mofetil.

Specifically, in the treatment of atopic dermatitis, a compound of any formula described herein may be administered in combination with a topical immunomodulator or calcineurin inhibitor (such as pimecrolimus) or tacrolimus ointment, a topical corticosteroid (such as hydrocortizone, betamethasone, flurandrenolide, fluticasone, triamcinolone, fluocinonide, and clobetasol, an oral corticosteroid (such as hydrocortisone, methylprednisolone, or prednisolone, an interferon gamma (Alferon N, Infergen, Intron A, Roferon-A), an antihistamine (for itching such as Atarax, Vistaril, Benadryl), or an antibiotic (such as penicillin derivatives flucloxacillin or dicloxacillin, erythromycin).

In the treatment of burns, e.g. a burn injury or burn shock, a compound of any formula described herein may be administered alone, or in combination with an antimicrobial agent, typically a topical antibiotic (mafenide acetate cream, silver sulfadiazine cream) and/or an analgesic (opioid analgesics, e.g., morphine, oxycodone). Other therapeutic agents that may be useful for the treatment of burns include retinoids and pirfenidone.

In certain embodiments, the at least one other therapeutically active agent is selected from a thrombolytic agent, a tissue plasminogen activator, an anticoagulant, and a platelet aggregation inhibitor.

In certain embodiments, the at least one other therapeutically active agent is selected from heparin, coumadin, clopidrogel, dipyridamole, ticlopidine HCL, eptifibatide, and aspirin. In certain embodiments, the kinase-mediated disease or disorder treated with these agents is a cerebrovascular accident.

In certain embodiments, the at least one other therapeutically active agent is selected from broad-spectrum antibiotic, anti-MRSA therapy and a low dose steroid. In certain embodiments, the at least one other therapeutically active agent is selected from vacomycin, cefeprime, a combination of piperacillin and tazobactam, imipenem, meropenem, doripenem, ciprofloxacin, levofloxacin, ofloxacin, moxifloxacin, and hydrocortisone. In certain embodiments, the disease or disorder treated with these agents is systemic inflammatory response syndrome.

In certain embodiments, the at least one other therapeutically active agent is alicaforsen or remestemcel-L. In certain embodiments, the disease or disorder treated with these agents is Crohn's disease or ulcerative colitis.

In certain embodiments, the at least one other therapeutically active agent is ixekizumab, or tildrakizumab. In certain embodiments, the kinase-mediated disease or disorder treated with these agents is of non-communicable inflammatory skin diseases (ncISD) such as psoriasis or atopic dermatitis.

In certain embodiments, the at least one other therapeutically active agent is an antimicrobial agent or an antibiotic. In certain embodiments, the at least one other therapeutically active agent is selected from chlorhexidine, doxycycline and minocycline. In certain embodiments, the disease or disorder treated with these agents is periodontis.

In certain embodiments, the at least one other therapeutically active agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. In certain embodiments, the at least one other therapeutically active agent is selected from fluticasone proprionate, beclomethasone dipropionate, budesonide, trimcinolone acetonide, flunisolide, mometasone fuorate, or ciclesonide, formoterol fumarate, salmeterol xinafoate, a combination of fluticasone furoate and vilanterol, a combination of formoterol and budesonide inhalation, a combination of beclomethasone dipropionate and formoterol, a combination of fluticasone propionate and salmeterol, albuterol sulfate, levalbuterol tartrate, a combination of ipratropium bromide and albuterol, ipratropium bromide, montelukast sodium, zafirlukast, zileuton, omalizumab theophylline, cromulyn sodium, nedocromil sodium, and a combination of mometasone furoate and formoterol fumarate dihydrate. In certain embodiments, the at least one other therapeutically active agent is selected from protein tyrosine kinase inhibitor, a CRTH2/D-prostanoid receptor antagonist, an epinephrine inhalation aerosol, and a combination of a phosphodiesterase-3 inhibitor and a phosphodiesterase-4 inhibitor. In certain embodiments, the at least one other therapeutically active agent is selected from masitinib, AMG 853, indacaterol, E004, a combination of fluticasone furoate and fluticasone proprionate, a combination of vinanterol fluticasone furoate, a combination of fluticasone propionate and eformoterol fumarate dihydrate, reslizumab, salbutamol, tiotropium bromide, a combination of formoterol and budesonide, fluticasone furoate, VR506, lebrikizumab, and RPL554. In certain embodiments, the kinase-mediated disease or disorder treated with these agents is asthma.

In certain embodiments, the at least one other therapeutically active agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. In certain embodiments, the at least one other therapeutically active agent is selected from salmeterol xinafoate, a combination of umeclidinium and vilanterol, umeclidinium, arformoterol tartrate, formoterol fumarate, indacterol maleate, a combination of fluticasone propionate and eformoterol fumarate dihydrate, tiotropium bromide, aclidinium bromide, roflumilast, a combination of fluticasone furoate and vilanterol, a combination of fluticasone propionate and salmeterol, a combination of budesonide and formoterol, a combination of mometasone and formoterol, a combination of ipratropium bromide and albuterol sulfate, a combination of albuterol and ipratropium, ipratropium bromide, albuterol sulfate, budesonide, fluticasone propionate, and beclometasone dipropionate. In certain embodiments, the at least one other therapeutically active agent is selected from SCH527123, glycoprronium bromide, a combination of glycopyrronium bromide and indacaterol maleate, a combination of glycopyrrolate and formoterol fumarate, indacaterol maleate, olodaterol, tiotropium, olodaterol, and a combination of aclidinium and formoterol. In certain embodiments, the disease or disorder treated with these agents is COPD.

In certain embodiments, the at least one other therapeutically active agent is an antimycobacterial agent or a bactericidal antibiotic. In certain embodiments, the at least one other therapeutically active agent is selected from isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, and delamanid. In certain embodiments, the kinase-mediated disease or disorder treated with these agents is a mycobacterium infection.

In certain embodiments, the at least one other therapeutically active agent is selected from an oral corticosteroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor or imatinib, ARG201, and tocilizumab. In certain embodiments, the at least one active agent is selected from prednisolone, anti-thymocyte globulin, FK506 (tacrolimus), thalidomide, chlorambucil, nifedipine, nicardipine, nitroglycerin ointment, lisinopril, diltaizem, fluoxetine, bosentan, epoprostenol, colchicines, para-aminobenzoic acid, dimethyl sulfoxide, D-penicillamine, interferon alpha, interferon gamma (INF-g), omeprazole, metoclopramide, ansoprazole, esomeprazole, pantoprazole, rabeprazole, imatinib, ARG201, and tocilizumab. In certain embodiments, the disease or disorder treated with these agents is systemic scleroderma.

In certain embodiments, the at least one other therapeutically active agent is selected from a cystic fibrosis transmembrane conductance regulator potentiator, amucolytic agent, pancreatic enzymes, a bronchodilator, an antibiotic, or ivacftor/lumacaftor, ataluren, and tiopropium bromide. In certain embodiments, the at least one other therapeutically active agent is selected from ivacaftor, dornase alpha, pancrelipase, albuterol, tobramycin, aztreonam, colistimethate sodium, cefadroxil monohydrate, cefazolin, cephalexin, cefazolin, moxifloxacin, levofloxacin, gemifloxacin, azithromycin, gentamicin, piperacillin/tazobacam, ceftazidime, ciprofloxin, trimethoprim/sulfamethoxazole, chloramphenicol, or ivacaftor/lumacaftor, ataluren, and tiopropium bromide. In certain embodiments, the disease or disorder treated with these agents is cystic fibrosis.

In certain embodiments, the at least one other therapeutically active agent is a ciliary neurotrophic growth factor or a gene transfer agent. In certain embodiments, the at least one other therapeutically active agent is NT-501-CNTF or a gene transfer agent encoding myosin VIIA (MYO7A).

In certain embodiments, the disease or disorder treated with these agents is retinitis pigmentosa.

In certain embodiments, the at least one other therapeutically active agent is selected from opthalmalic intravitreal injections, an anti-vascular endothelial growth factor inhibitor, and a ciliary neurotrophic growth factor agent. In certain embodiments, the at least one other therapeutically active agent is selected from afibercept, ranibizumab, pegaptanib sodium, NT501, humanized sphingomab, and bevacizumab. In certain embodiments, the disease or disorder treated with these agents is macular degeneration.

In certain embodiments, the at least one other therapeutically active agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. In certain embodiments, the at least one other therapeutically active agent is selected from oseltamivir, zanamivir, rimantadine, or amantadine. In certain embodiments, the kinase-mediated disease or disorder treated with these agents is influenza.

In certain embodiments, the at least one other therapeutically active agent is selected from a beta-Lactam, nafcillin, sulfamethoxazolem, trimethoprim, sulfasalazine, acetyl sulfisoxazole, and vancomycin. In certain embodiments, disease or disorder treated with these agents is a staphylococcus infection.

In certain embodiments, the at least one other therapeutically active agent is selected from a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb.

In certain embodiments, the at least one other therapeutically active agent is selected from muromonab-CD3, ASKP-1240, ASP015K, and TOL101. In certain embodiments, the disease or disorder treated with these agents is transplant rejection.

In certain embodiments, the at least one other therapeutically active agent is selected from a topical immunomodulator or calcineurin inhibitor, a topical corticosteroid, an oral corticosteroid, an interferon gamma, an antihistamine, or an antibiotic. In certain embodiments, the at least one other therapeutically active agent is selected from pimecrolimus, tacrolimus, hydrocortizone, betamethasone, flurandrenolide, fluticasone, triamcinolone, fluocinonide, clobetasol, hydrocortisone, methylprednisolone, prednisolone, an interferon alpha protein, a recombinant synthetic type I interferon, interferon alpha-2a, interferon alpha-2b, hydroxyzine, diphenhydramine, flucloxacillin, dicloxacillin, and erythromycin. In certain embodiments, the disease or disorder treated with these agents is atopic dermatitis.

Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration", "administered systemically", "peripheral administration" and "administered peripherally" as used herein mean the administration of a compound, drug or other material other than directly into the central nervous system, such that it enters the subject's system and, thus, is subject to metabolism and other like processes, for example, subcutaneous administration. These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active compounds in the pharmaceutical compositions of this disclosure may be varied so as to obtain an amount of the active compound that is effective to achieve the desired therapeutic response for a particular subject, composition and mode of administration, without being toxic to the subject.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above.

Generally doses of the compounds of this disclosure for a subject, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms. In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar. The compounds of the disclosure can be tested in standard animal models of stroke and standard protocols such as described by Hara, H., et al. *Proc. Natl. Acad. Sci. USA,* 1997.94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active compound in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound of the disclosure administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day. In certain embodiments, the method comprises administering to the subject an initial daily dose of about 1 to 800 mg of a compound of the disclosure and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation-topical by lotion or ointment; and rectal by suppositories. In certain embodiments, the administration is oral.

EXAMPLES

| Abbreviations: | |
|---|---|
| ADP | Adenosindiphosphate |
| ATP | Adenosintriphosphate |
| BOC | Tertiar butyl-oxy-carbonyl |
| CMC | Carboxy-methyl-cellulose |
| CRC | Concentration response curve |
| DCM | Dichloromethane |
| DEA | Diethylamine |
| DIAD | Diisopropyl azodicarboxylate |
| DIPEA | Diisopropylethylamine |
| DME | Dimethoxyethane |
| DMF | Dimethylformamide |
| DMSO | Dimethylsulfoxide |
| Eq. | equivalent |
| ES | Electro spray |
| EtOH | ethanol |
| FBS | Fetal bovine serum |
| HATU | 1-[Bis(dimethylamino)methylene]-1H-1,2,3-triazolo[4,5-b]pyridinium 3-oxide hexafluorophosphate |
| HBTU | (2-(1H-Benzotriazol-1-yl)-1,1,3,3-tetramethyluronium-hexafluorophosphat) |
| HOBt | 1-Hydroxybenzotriazole |
| HPLC | High pressure liquid chromatography |
| hr/hrs | Hour/hours |
| i-PrOH | Isopropylalcohole |

-continued

| Abbreviations: | |
|---|---|
| IL6 | Interleukin 6 |
| LC/MS | Liquid chromatography mass spectrum |
| m/z | Mass per charge |
| MeOH | methanol |
| MHz | Mega Hertz |
| min | Minute(s) |
| N | Normal |
| n-BuOH | n-Butanol |
| NMR | Nuclear magnetic resonance |
| PBS | Phosphate buffered saline |
| PG | Protecting group |
| rH | Relative humidity |
| TBHP | Tert-butyl hydroperoxide |
| TFA | Trifluoroacetic acid |
| THF | Tetrahydrofuran |
| TNF | Tumor Necrosis Factor |
| tR | retention time |
| UV | ultraviolet |

Silica Gel Chromatography

Silica gel chromatography was performed using CombiFlash® Rf (Teledyne ISCO), Biotage Isolera One automated flash purification system or two Buchi systems (C-660, C-605, C-620, C-635 combination and C-660, C-605, C-615, C-630 combination) with pre-packed cartridges.

Preparative Reversed-Phase HPLC

For preparative reversed-phase HPLC an Agilent 1200 preparative HPLC machine, Gilson equipment (GX-271 liquid handler, 331/332-pump, UV/VIS-155) or a Waters Autopurification LC Prep System was used.

Preparative RP-LC

Reversed phase liquid chromatography was performed with a Biotage equipment using C18 columns and a water (0.1% formic acid)/acetonitrile gradient.

NMR

400 MHz: NMR spectra were recorded on a Bruker AVANCE II 400 spectrometer operating at a proton frequency of 400.23 MHz. The instrument was equipped with a 5 mm BBI room temperature probe head. Alternatively, a Bruker AVANCE III HD 400 MHz, or a Bruker AVANCE NEO 400 MHz was used.

600 MHz: NMR spectra were recorded on a Bruker AVANCE III 600 spectrometer operating at a proton frequency of 600.05 MHz. The instrument was equipped with a 5 mm BBI room temperature probe head. Analytical LC/MS equipment for method A Analytical LC/MS Equipment for Method A Retention time and mass detection were done on a Waters Acquity UHPLC system coupled with a Waters SQD mass detector. The injection volume was 1.0 µl. Molecular weights are given in gram per mol [g/mol], detected masses in mass per charge [m/z].

Analytical LC/MS Equipment for Method B, C, D

For retention time and mass detection a LC/MS-system from Agilent (LC 1200 Series/MS 6120 quadrupole LC/MS, LC 1260 infinity/MS 6120 quadrupole LC/MS or LC 1260 Infinity II/MSD Infinity Lab) was used. Molecular weights are given in gram per mol [g/mol], detected masses in mass per charge [m/z].

LC/MS-Method A

Gradient: 98% $H_2O$ (0.05% formic acid)/2% acetonitrile (0.035% formic acid) for 0.2 min, then from 98% $H_2O$ (0.05% formic acid) to 98% acetonitrile (0.035% formic acid) in 3.6 min, then 98% acetonitrile (0.035% formic acid) for 0.5 min, flow rate: 1.0 ml/min, column: 2.1×50 mm Waters ACQUITY UPLC BEH C18, 1.7 µm, 55° C.

UV data: retention time ad λ=220 nm given in min

MS data: ES+ ionisation, m/z given as [M+H]$^+$ unless otherwise noted

LC/MS-Method B

Gradient: From 93% $H_2O$ (0.05% TFA)/7% acetonitrile to 95% acetonitrile in 1.0 min, then 95% acetonitrile for 0.45 min, flow rate: 1.1 ml/min, column: 2.0×10 mm LunaC18, 3 µm, 30° C., injection volume 0.2 µl UV data: retention time ad λ 220 nm given in min MS data: ES+ ionisation, m/z given as [M+H]$^+$ unless otherwise noted LC/MS-Method C Gradient: From 95% $H_2O$ (0.0375% TFA)/5% acetonitrile (0.01875% TFA) to 5% $H_2O$ (0.0375% TFA)/95% acetonitrile (0.01875% TFA) in 0.8 min, flow rate: 1.5 ml/min, column: Kinetex EVO C18 2.1×30 mm, 5 µm, 50° C.

UV data: retention time ad λ 220 nm given in min

MS data: ES+ ionisation, m/z given as [M+H]$^+$ unless otherwise noted

LC/MS-Method D

Gradient: From 100% $H_2O$ (0.0375% TFA)/0% acetonitrile (0.01875% TFA) to 40% $H_2O$ (0.0375% TFA)/60% acetonitrile (0.01875% TFA) in 0.8 min, then 40% $H_2O$ (0.0375% TFA)/60% acetonitrile (0.01875% TFA) for 0.4 min, flow rate: 1.5 ml/min, column:

Kinetex EVO C18 2.1×30 mm, 5 µm, 50° C.

UV data: retention time ad λ 220 nm given in min

MS data: ES+ ionisation, m/z given as [M+H]$^+$ unless otherwise noted

Analytical Chiral HPLC

SFC: SHIMADZU LC-30AD sf system

LC: Agilent 1100 series system

Salts

In compounds described as HCl-, TFA- or as another salt, the exact amount of the respective salt is usually not determined. Therefore, the amount of the salt can range from as low as 0.01 eq. up to 5.0 eq. depending on the chemical structure (e.g. number of basic centres).

Chiral Purity

Compounds are drawn and named as a single enantiomer, if the enantiomeric ratio exceeded 90:10. For enantiomeric ratios below 90:10 the racemic form is used.

Synthetic Methods:

Synthesis of Comparator Compounds:

Comparator Example A (GSK WO2018 092089, Example 4)

(3-Phenyl-3,4-dihydropyrazol-2-yl)-[1-(4-phenylpyrimidin-2-yl)-4-piperidyl]methanone

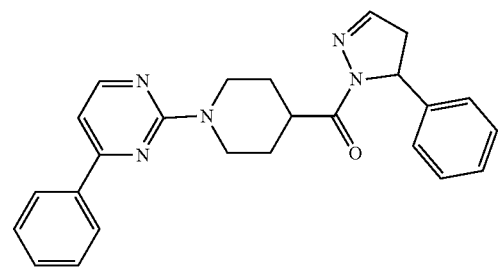 [SMILES: O=C(C1CCN(c2nccc(-c3ccccc3)n2)CC1)N1N=CCC1c1ccccc1]

Step 1:

tert-Butyl 4-(3-phenyl-3,4-dihydropyrazole-2-carbonyl)piperidine-1-carboxylate

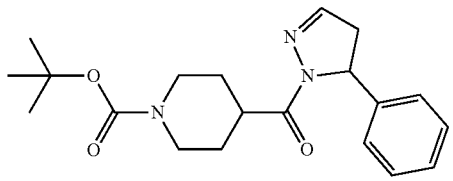 [SMILES: CC(C)(C)OC(=O)N1CCC(C(=O)N2N=CCC2c2ccccc2)CC1]

To a mixture of 5-phenyl-4,5-dihydro-1H-pyrazole (500 mg, 3.42 mmol, 1.0 eq.), 1-(tert-butoxycarbonyl)piperidine-4-carboxylic acid (862.58 mg, 0.74 ml, 3.76 mmol, 1.1 eq.) and HATU (1950.7 mg, 5.13 mmol, 1.5 eq.) in DMF (5 ml, 64.6 mmol) DIPEA (1105.1 mg, 1.49 ml, 8.5 mmol, 2.5 eq.) was added and the reaction mixture was stirred at room temperature for 2 hrs. The reaction mixture was evaporated under reduced pressure, diluted in ethyl acetate, and washed with 0.1 N aqueous HCl solution and water. The organic layer was dried with $Na_2SO_4$, filtered, evaporated, and purified by silica gel chromatography (40 g $SiO_2$, eluent: heptane and ethyl acetate, gradient: 0% to 50% ethyl acetate, flow: 40 ml/min) to give the title compound (1.22 g, 94% yield). LC/MS: m/z=[M−56+H]$^+$; tR: 0.89 min (LC/MS-method B).

Step 2:

(3-Phenyl-3,4-dihydropyrazol-2-yl)-(4-piperidyl)methanone

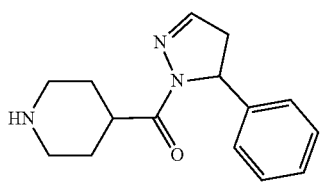 [SMILES: O=C(C1CCNCC1)N1N=CCC1c1ccccc1]

A solution of tert-butyl 4-(3-phenyl-3,4-dihydropyrazole-2-carbonyl)piperidine-1-carboxylate (1.145 g, 3.204 mmol, 1.0 eq.), DCM (25 mg, 0.2944 mmol, 0.1 eq.) and TFA (3.653 g, 2.47 ml, 32.04 mmol, 10.00 eq.) was stirred at room temperature for 24 hrs. The reaction mixture was diluted with toluene (10 ml) and evaporated. The crude product was diluted with water and acetonitrile and lyophilized. The crude material was diluted with saturated $NaHCO_3$ solution and extracted with DCM two times. The combined organic layer was dried with $Na_2SO_4$, filtered and evaporated to give the title compound (824 mg, 76% yield).

LC/MS: m/z=258.1 [M+H]$^+$; tR: 0.87 min (LC/MS-method A).

$^1$H NMR (400.23 MHz, DMSO-d$_6$): δ ppm 7.27 (m, 4H), 7.10 (m, 2H), 5.29 (dd, J=11.92, 4.58 Hz, 1H), 3.48 (m, 1H), 3.23 (m, 1H), 3.10 (m, 1H), 3.00 (m, 1H), 2.69 (m, 2H), 1.91 (m, 1H), 1.81 (m, 1H), 1.47-1.75 (m, 4H)

Step 3:

(3-Phenyl-3,4-dihydropyrazol-2-yl)-[1-(4-phenylpyrimidin-2-yl)-4-piperidyl]methanone

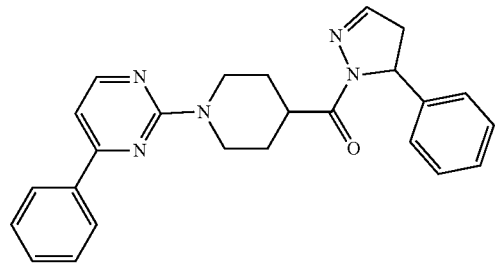

To a solution of (3-phenyl-3,4-dihydropyrazol-2-yl)-(4-piperidyl)methanone (77.2 mg, 0.300 mmol, 1.00 eq.) and 2-chloro-4-phenyl-pyrimidine (62.9 mg, 0.330 mmol, 1.10 eq.) in acetonitrile (4 ml) DIPEA (96.9 mg, 0.131 ml, 0.750 mmol, 2.50 eq.) was added. The reaction mixture was heated to 100° C. under microwave irradiation for 30 minutes. Again DIPEA (96.9 mg, 0.131 ml, 0.750 mmol, 2.50 eq.) was added and the reaction mixture was heated to 100° C. under microwave irradiation for 30 minutes. After addition of a catalytic amount of $K_2CO_3$ and DMF (0.5 ml) the reaction mixture was heated to 100° C. under microwave irradiation for 30 minutes. The reaction mixture was filtered, washed with acetonitrile, and the filtrate was evaporated under reduced pressure. The residue was purified by preparative HPLC (column: Luna(r) 5 µm C18(2) 100 Å 100×30 mm, AXIAL; eluent: water and acetonitrile; gradient: 5% to 100% acetonitrile in 20 minutes, flow: 50 ml/min) to give the title compound (55 mg, 45% yield).

LC/MS: m/z=412.2 [M+H]$^+$; tR: 2.51 min (LC/MS-method A).

$^1$H NMR (400.23 MHz, DMSO-d$_6$): δ ppm 8.42 (d, J=5.14 Hz, 1H), 8.11 (m, 2H), 7.51 (m, 3H), 7.31 (m, 2H), 7.18 (m, 5H), 5.31 (dd, J=11.86, 4.65 Hz, 1H), 4.80 (br d, J=13.08 Hz, 2H), 3.48 (m, 2H), 3.05 (m, 2H), 2.68 (m, 1H), 1.92 (br d, J=11.00 Hz, 1H), 1.80 (br d, J=11.49 Hz, 1H), 1.51 (m, 2H)

Comparator Example B (Isoxazolidine of Comparator Example A)

[(3S)-3-Phenylisoxazolidin-2-yl]-[1-(4-phenylpyrimidin-2-yl)-4-piperidyl]methanone

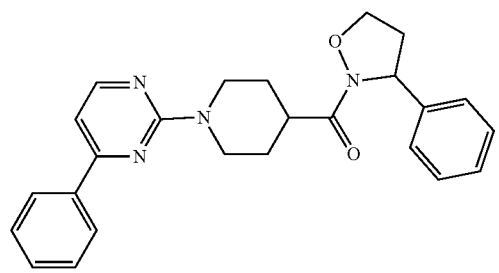 [SMILES: O=C(C1CCN(c2nccc(-c3ccccc3)n2)CC1)N1OCCC1c1ccccc1]

Step 1:

tert-Butyl 4-[(3S)-3-phenylisoxazolidine-2-carbonyl]piperidine-1-carboxylate

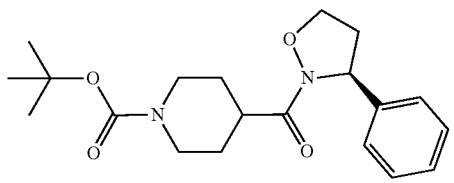 [SMILES: CC(C)(C)OC(=O)N1CCC(C(=O)N2OCC[C@H]2c2ccccc2)CC1]

To a mixture of (S)-3-phenylisoxazolidine (500 mg, 3.35 mmol), 1-(tert-butoxycarbonyl)piperidine-4-carboxylic acid (922 mg, 4.02 mmol) and HATU (1.91 g, 5.03 mmol) in DMF (10 ml) DIPEA (1.46 ml, 8.38 mmol) was added and the reaction mixture was stirred at room temperature for 2 hrs. The reaction mixture was diluted with half saturated NH$_4$Cl solution and ethyl acetate, the organic layer was washed with water, dried with Na$_2$SO$_4$, filtered, evaporated and purified by silica gel chromatography (40 g SiO$_2$, eluent: DCM and DCM/methanol=9/1, gradient: 0% to 50% DCM/methanol=9/1, flow: 40 ml/min) to give the title compound (920 mg, 76% yield).

LC/MS: m/z=381.3 [M+H]$^+$; tR: 2.28 min (LC/MS-method A).

Step 2:

[(3S)-3-Phenylisoxazolidin-2-yl]-(4-piperidyl)methanone

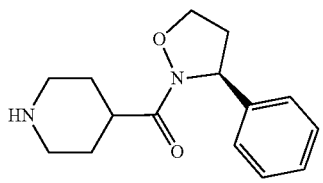 [SMILES: O=C(C1CCNCC1)N1OCC[C@H]1c1ccccc1]

A solution of tert-butyl 4-[(3S)-3-phenylisoxazolidine-2-carbonyl]piperidine-1-carboxylate (920 mg, 2.55 mmol), DCM (20 ml) and TFA (2.9 g, 1.96 ml, 25.47 mmol) was stirred at room temperature for 16 hrs. The reaction mixture was diluted with toluene (5 ml), evaporated and lyophillized two times to give the title compound (850 mg, 84% yield).

LC/MS: m/z=261.2 [M+H]$^+$; tR: 0.90 min (LC/MS-method A).

$^1$H NMR (400.23 MHz, DMSO-d$_6$): δ ppm 8.50 (br s, 1H), 8.24 (br s, 1H), 7.34 (m, 2H), 7.27 (m, 3H), 5.31 (m, 1H), 4.27 (td, J=7.64, 7.64, 3.06 Hz, 1H), 3.91 (m, 1H), 3.25 (m, 1H), 2.93 (m, 3H), 2.55 (m, 1H), 2.20 (m, 1H), 1.98 (br t, J=9.66, 9.66 Hz, 2H), 1.80 (br s, 1H), 1.71 (m, 2H)

Step 3:

[(3S)-3-Phenylisoxazolidin-2-yl]-[1-(4-phenylpyrimidin-2-yl)-4-piperidyl]methanone

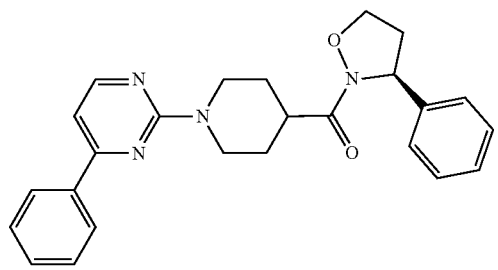 [SMILES: O=C(C1CCN(c2nccc(-c3ccccc3)n2)CC1)N1OCC[C@H]1c1ccccc1]

To a solution of [(3S)-3-phenylisoxazolidin-2-yl]-(4-piperidyl)methanone trifluoroacetic acid salt (116 mg, 0.300 mmol, 1.00 eq.) and 2-chloro-4-phenyl-pyrimidine (62.9 mg, 0.330 mmol, 1.10 eq.) in acetonitrile (4 ml) DIPEA (136 mg, 0.183 ml, 1.05 mmol, 3.50 eq.) was added heated to 100° C. under microwave irradiation for 30 minutes. Again DIPEA (96.9 mg, 0.131 ml, 0.750 mmol, 2.50 eq.) was added and the reaction mixture was heated to 100° C. under microwave irradiation for 30 minutes. After addition of a catalytic amount of K$_2$CO$_3$ and DMF (0.5 ml) the reaction mixture was heated to 100° C. under microwave irradiation for 30 minutes. The reaction mixture was filtered, washed with acetonitrile and the filtrate was evaporated under reduced pressure. The residue was purified by preparative HPLC (column: Luna(r) 5 μm C18(2) 100 Å 100×30 mm, AXIAL; eluent: water and acetonitrile; gradient: 5% to 100% acetonitrile in 20 minutes, flow: 50 ml/min) to give the title compound (73 mg, 59% yield).

LC/MS: m/z=415.2 [M+H]$^+$; tR: 2.58 min (LC/MS-method A).

$^1$H NMR (400.23 MHz, DMSO-d$_6$): δ ppm 8.43 (d, J=5.14 Hz, 1H), 8.12 (m, 2H), 7.51 (m, 3H), 7.30 (m, 5H), 7.18 (d, J=5.14 Hz, 1H), 5.33 (br t, J=7.46, 7.46 Hz, 1H), 4.78 (br dd, J=8.99, 3.97 Hz, 2H), 4.29 (td, J=7.73, 7.73, 3.00 Hz, 1H), 3.92 (m, 1H), 3.08 (br t, J=11.43, 11.43 Hz, 3H), 2.89 (m, 1H), 2.20 (m, 1H), 1.94 (br d, J=11.49 Hz, 1H), 1.75 (br s, 1H), 1.53 (m, 2H)

Comparator Example C (GSK WO2018 092089, Example 129)

[1-[6-(5-Methyl-1,3,4-oxadiazol-2-yl)pyrimidin-4-yl]-4-piperidyl]-[(3S)-3-phenyl-3,4-dihydropyrazol-2-yl]methanone

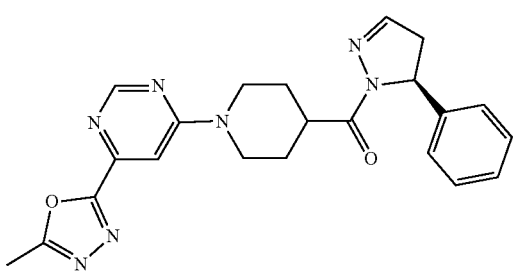 [SMILES: Cc1nnc(-c2cc(N3CCC(C(=O)N4N=CC[C@H]4c4ccccc4)CC3)ncn2)o1]

Step 1

N'-Acetyl-6-chloro-pyrimidine-4-carbohydrazide

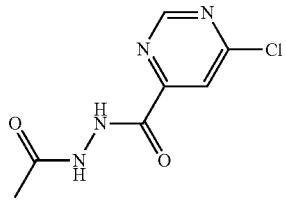

To a solution of 6-chloropyrimidine-4-carboxylic acid (500 mg, 3.00 mmol, 1.00 eq.) in THF (30 ml) DMF (4.38 mg, 4.6 µl, 59.9 µmol, 0.02 eq.) was added under argon atmosphere and the reaction mixture was cooled to 0° C. Oxalyl chloride (2 M in DCM) (2.25 ml, 4.49 mmol, 1.5 eq.) was added dropwise. Afterwards the reaction was allowed to warm up to room temperature and stirred for 1 hr. The mixture was evaporated under reduced pressure, the residue was solved in 1,4-dioxane (30 ml) and cooled to 0° C. Acethydrazide (444 mg, 5.99 mmol, 2.00 eq.) was added, the reaction mixture was allowed to warm to room temperature and stirred for 1 hr. The mixture was evaporated under reduced pressure and used in the next step without purification.

Step 2:

2-(6-Chloropyrimidin-4-yl)-5-methyl-1,3,4-oxadiazole

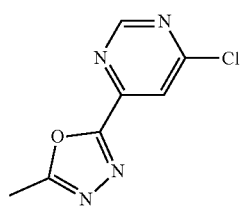

A solution of N'-acetyl-6-chloro-pyrimidine-4-carbohydrazide (step 1, crude) in acetonitrile (30 ml) was cooled to 0° C. and DIPEA (774 mg, 1.04 ml, 5.99 mmol, 2.0 eq.) was added dropwise. p-Toluenesulfonyl chloride (1.713 g, 8.99 mmol, 3.0 eq.) was added, the reaction mixture was allowed to warm to room temperature and stirred for 20 minutes. The reaction mixture was evaporated under reduced pressure and purified by silica gel chromatography (80 g SiO$_2$, eluent: n-heptane and ethyl acetate, gradient: 0% to 100% ethyl acetate, flow: 60 ml/min) to give the title compound (83 mg, 14% yield over both steps). Unreacted reagent N'-acetyl-6-chloro-pyrimidine-4-carbohydrazide (355 mg, 55% yield) was isolated.

Re-isolated reagent was also converted to the title compound as described above to give 254 mg (79% yield).

LC/MS: m/z=197 [M+H]$^+$; tR: 0.99 min (LC/MS-method A).

$^1$H NMR (400.23 MHz, DMSO-d$_6$): δ ppm 9.26 (d, J=0.98 Hz, 1H), 8.33 (d, J=0.98 Hz, 1H), 2.66 (s, 3H)

Step 3

[1-[6-(5-Methyl-1,3,4-oxadiazol-2-yl)pyrimidin-4-yl]-4-piperidyl]-[(3S)-3-phenyl-3,4-dihydropyrazol-2-yl]methanone

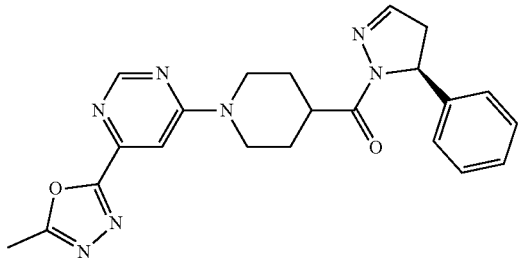

To a mixture of (3-phenyl-3,4-dihydropyrazol-2-yl)-(4-piperidyl)methanone (Comparator example A, step 2, 154.4 mg, 0.600 mmol, 1.00 eq.) and 2-(6-chloropyrimidin-4-yl)-5-methyl-1,3,4-oxadiazole (123.85 mg, 0.63 mmol, 1.05 eq.) in acetonitrile (20 ml) DIPEA (193.86 mg, 0.261 ml, 1.5 mmol, 2.5 eq.) was added. The reaction mixture was heated to 100° C. under microwave irradiation for 30 minutes, evaporated under reduced pressure and purified by preparative HPLC (column: Luna(r) 5 µm C18(2) 100 Å 100×30 mm, AXIAL; eluent: water and acetonitrile; gradient: 10% to 100% acetonitrile in 12 minutes, flow: 50 ml/min) to give the racemate of the title compound (153 mg, 61% yield).

The isomers were separated by chiral HPLC (column: Chiralpak IB/83, 250×4.6 mm; eluent: heptane:EtOH:MeOH 2:1:1; isocratic gradient) to give the title compound (67 mg, 27% yield).

LC/MS: m/z=418.2 [M+H]$^+$; tR: 1.68 min (LC/MS-method A).

$^1$H NMR (400.23 MHz, DMSO-d$_6$): δ ppm 8.61 (d, J=0.98 Hz, 1H), 7.42 (d, J=0.98 Hz, 1H), 7.27 (m, 4H), 7.11 (d, J=7.49 Hz, 2H), 5.31 (dd, J=11.86, 4.65 Hz, 1H), 4.49 (br s, 2H), 3.48 (m, 2H), 3.13 (m, 2H), 2.68 (m, 1H), 2.60 (s, 3H), 1.94 (br d, J=11.62 Hz, 1H), 1.82 (br d, J=10.88 Hz, 1H), 1.51 (m, 2H)

Comparator Example D (Isoxazolidin of Comparator Example C)

[1-[6-(5-Methyl-1,3,4-oxadiazol-2-yl)pyrimidin-4-yl]-4-piperidyl]-[(3S)-3-phenylisoxazolidin-2-yl]methanone

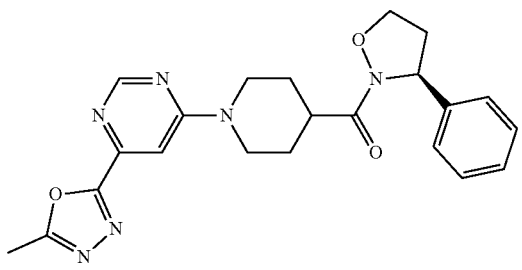 [SMILES: Cc1nnc(-c2cc(N3CCC(C(=O)N4OCC[C@H]4c4ccccc4)CC3)ncn2)o1]

To a solution of [(3S)-3-phenylisoxazolidin-2-yl]-(4-piperidyl)methanone trifluoroacetic acid salt (Comparator example B, step 2, 116 mg, 0.300 mmol, 1.00 eq.) and 2-(6-chloropyrimidin-4-yl)-5-methyl-1,3,4-oxadiazole (61.9 mg, 0.315 mmol, 1.05 eq.) in acetonitrile (10 ml) DIPEA (136 mg, 0.183 ml, 1.05 mmol, 3.50 eq.) was added. The reaction mixture was heated to 100° C. under microwave irradiation for 30 minutes and purified by preparative HPLC (column: Luna(r) 5 µm C18(2) 100 Å 100×30 mm, AXIAL; eluent: water and acetonitrile; gradient: 10% to 100% acetonitrile in 12 minutes, flow: 50 ml/min) to give the title compound (89 mg, 71% yield).

LC/MS: m/z=421.2 [M+H]$^+$; tR: 1.75 min (LC/MS-method A).

$^1$H NMR (400.23 MHz, DMSO-d$_6$): δ ppm 8.62 (s, 1H), 7.43 (s, 1H), 7.30 (m, 5H), 5.33 (m, 1H), 4.47 (br s, 2H), 4.28 (m, 1H), 3.92 (m, 1H), 3.19 (br s, 1H), 3.14 (m, 2H), 2.89 (m, 1H), 2.61 (s, 3H), 2.20 (m, 1H), 1.96 (br d, J=12.96 Hz, 1H), 1.77 (br s, 1H), 1.54 (m, 2H)

Comparator Example E (Substituted Phenyl-Isoxazolidin of Comparator Example C)

3-Fluoro-5-[(3S)-2-[1-[6-(5-methyl-1,3,4-oxadiazol-2-yl)pyrimidin-4-yl]piperidine-4-carbonyl]isoxazolidin-3-yl]benzonitrile

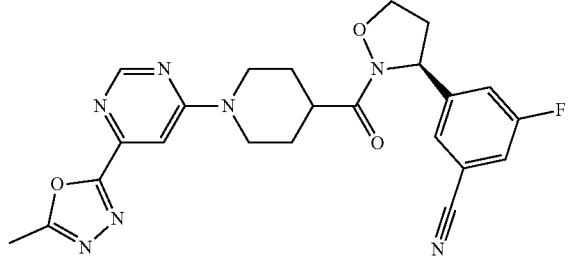 [SMILES: Cc1nnc(-c2cc(N3CCC(C(=O)N4OCC[C@H]4c4cc(F)cc(C#N)c4)CC3)ncn2)o1]

Comparator example E was synthesized in analogy to comparator example D using 3-fluoro-5-[(3S)-2-(piperidine-4-carbonyl)isoxazolidin-3-yl]benzonitrile (synthesized from Intermediate-1 as described for comparator example B) instead of [(3S)-3-phenylisoxazolidin-2-yl]-(4-piperidyl)methanone and HBTU instead of HATU as coupling reagent to give 14.8 mg (31.9 µmol, 32% yield).

LC/MS: m/z=464.3 [M+H]$^+$; tR: 1.77 min (LC/MS-method A).

$^1$H NMR (400.23 MHz, DMSO-d$_6$): δ ppm 8.62 (d, J=0.86 Hz, 1H), 7.77 (d, J=8.62 Hz, 1H), 7.62 (s, 1H), 7.49 (br d, J=9.66 Hz, 1H), 7.43 (s, 1H), 5.40 (m, 1H), 4.46 (m, 2H), 4.30 (td, J=7.70, 7.70, 2.93 Hz, 1H), 3.95 (m, 1H), 3.14 (m, 3H), 2.91 (m, 1H), 2.61 (s, 3H), 2.27 (m, 1H), 1.99 (br d, J=11.62 Hz, 1H), 1.80 (br d, J=11.62 Hz, 1H), 1.54 (m, 2H), 1.24 (s, 1H)

Synthesis of Intermediates:
Intermediate-01

3-Fluoro-5-[(3S)-isoxazolidin-3-yl]benzonitrile

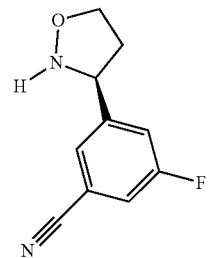 [SMILES: N#Cc1cc(F)cc([C@@H]2CCON2)c1]

Step 1

3-Fluoro-5-[(E)-3-oxoprop-1-enyl]benzonitrile

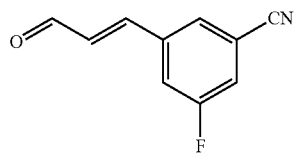 [SMILES: N#Cc1cc(F)cc(/C=C/C=O)c1]

To a solution of 3-fluoro-5-formyl-benzonitrile (90 g, 603.53 mmol, 1 eq.) in THF (900 ml) was added 2-(triphethyl-lambda5-phosphanylidene)acetaldehyde (183.67 g, 603.53 mmol, 1 eq.). The mixture was stirred at 70° C. for 12 hrs and concentrated. The residue was purified by silica gel chromatography (petroleum ether/ethyl acetate=1:0~3:1) to give the title compound (72 g, 68% yield) as yellow solid.

$^1$H NMR (400 MHz, CDCl$_3$): δ ppm 9.76 (d, J=7.3 Hz, 1H), 7.67-7.63 (m, 1H), 7.52 (td, J=1.8, 9.0 Hz, 1H), 7.46-7.39 (m, 2H), 6.74 (dd, J=7.4, 16.1 Hz, 1H)

Step 2 tert-Butyl (3S)-3-(3-cyano-5-fluoro-phenyl)-5-hydroxy-isoxazolidine-2-carboxylate

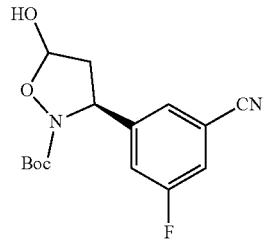 [SMILES: CC(C)(C)OC(=O)N1OC(O)C[C@H]1c1cc(F)cc(C#N)c1]

To a solution of [diphenyl-[(2S)-pyrrolidin-2-yl]methoxy]-trimethyl-silane (26.02 g, 79.93 mmol, 0.2 eq.) in CHCl$_3$ (300 ml) 3-fluoro-5-[(E)-3-oxoprop-1-enyl]benzonitrile (70 g, 399.64 mmol, 1 eq.) was added at 0° C., the mixture was stirred at 0° C. for 0.5 hrs and tert-butyl N-hydroxycarbamate (58.53 g, 439.60 mmol, 1.1 eq.) was added. The mixture was warmed to 20° C. smoothly and stirred for 12 hrs. The residue was purified by preparative reversed-phase HPLC (column: Phenomenex luna C18, 15 μm, 100 Å, I.D. 150×H400 mm, eluent: water (0.1% formic acid) and acetonitrile, gradient: from 60% to 47% acetonitrile in 53 min and 47% acetonitrile for 32 min, flow: 600 ml/min;) to give the title compound (77.5 g, 63% yield) as yellow solid.

LC/MS: m/z=191.1 [M−100−18+H]⁺; tR: 0.900 min (LC/MS method C).

¹H NMR (400 MHz, CDCl₃): δ ppm 7.46 (s, 1H), 7.34 (td, J=1.7, 9.2 Hz, 1H), 7.31-7.28 (m, 1H), 5.90 (d, J=4.4 Hz, 1H), 5.34 (t, J=8.3 Hz, 1H), 2.83 (dd, J=8.5, 12.5 Hz, 1H), 2.21 (ddd, J=4.4, 8.1, 12.5 Hz, 1H), 1.51-1.41 (m, 9H)

Step 3 tert-Butyl N-[(1 S)-1-(3-cyano-5-fluoro-phenyl)-3-hydroxy-propyl]-N-hydroxy-carbamate

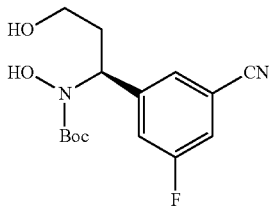 [SMILES: CC(C)(C)OC(=O)N(O)[C@@H](CCO)c1cc(F)cc(C#N)c1]

To a solution of tert-butyl (3S)-3-(3-cyano-5-fluoro-phenyl)-5-hydroxy-isoxazolidine-2-carboxylate (77.5 g, 251.38 mmol, 1 eq.) in MeOH (750 ml) NaBH₄ (10.46 g, 276.51 mmol, 1.1 eq.) was added at 0° C. The mixture was stirred at 0° C. for 3 hrs under N₂. The mixture was quenched with saturated NH₄Cl solution (100 ml), diluted with water (800 ml), extracted with ethyl acetate (1 L×3), dried with Na₂SO₄, filtered and concentrated. The residue was purified by preparative reversed-phase HPLC (column: Phenomenex luna C18, 15 μm, 100 Å, I.D. 150×H400 mm, eluent: water (0.1% formic acid) and acetonitrile, gradient: from 70% to 50% acetonitrile in 50 min, 50% acetonitrile for 26 min, flow: 400 ml/min) and silica gel column chromatography (petroleum ether/ethyl acetate=1:0-1:1) to give the title compound (59.5 g) as red brown solid, which was triturate with petroleum ether/ethyl acetate (4:1, 500 ml) to give the title compound (41 g filter cake as white solid and 18 g filtrate as red solid).

LC/MS: m/z=211.1 [M−100+H]⁺; tR: 0.850 min (LC/MS method C).

¹H NMR (400 MHz, CDCl₃): δ ppm 7.52 (s, 1H), 7.43 (td, J=1.9, 9.3 Hz, 1H), 7.30-7.27 (m, 1H), 5.25 (dd, J=5.0, 10.8 Hz, 1H), 3.93-3.73 (m, 2H), 2.45-2.33 (m, 1H), 2.05-1.97 (m, 1H), 1.46 (s, 9H)

Step 4 tert-Butyl (3S)-3-(3-cyano-5-fluoro-phenyl)isoxazolidine-2-carboxylate

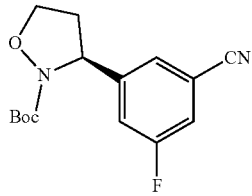 [SMILES: CC(C)(C)OC(=O)N1OCC[C@H]1c1cc(F)cc(C#N)c1]

To a solution of tert-butyl N-[(1 S)-1-(3-cyano-5-fluoro-phenyl)-3-hydroxy-propyl]-N-hydroxy-carbamate (41 g, 132.12 mmol, 1 eq.) in THF (410 ml) tributylphosphane (42.77 g, 211.39 mmol, 52.16 ml, 1.6 eq.) and DIAD (34.73 g, 171.76 mmol, 33.40 ml, 1.3 eq.) were added at 0° C. The mixture was warmed to 20° C. smoothly, stirred for 12 hrs under N₂ atmosphere. The residue was purified by preparative reversed-phase HPLC (column: Phenomenex luna C18, 15 μm, 100 Å, I.D. 150×H400 mm, eluent: water (0.1% formic acid) and acetonitrile, gradient: 70% to 50% acetonitrile in 50 min, 50% acetonitrile for 26 min, flow: 400 ml/min) and triturated with petroleum ether/ethyl acetate (10:1, 500 mL) to give the title compound (29.6 g filter cake, 77% yield, >99.9% e.e.) as white solid.

LC/MS: m/z=193.2 [M−100+H]⁺; tR: 0.901 min (LC/MS method C).

¹H NMR (400 MHz, CDCl₃): δ ppm 7.47 (s, 1H), 7.36 (td, J=1.8, 9.3 Hz, 1H), 7.27-7.24 (m, 1H), 5.25 (dd, J=5.6, 8.9 Hz, 1H), 4.20 (dt, J=3.2, 8.0 Hz, 1H), 3.95-3.83 (m, 1H), 2.85 (dddd, J=3.3, 7.0, 8.9, 12.3 Hz, 1H), 2.24 (dddd, J=5.6, 7.8, 9.2, 12.3 Hz, 1H), 1.50 (s, 9H)

SFC (Column: Chiralcel AD-3 50×4.6 mm I.D., 3 μm, gradient: 5% to 40% MeOH (0.05% DEA) in CO₂, flow rate: 3 ml/min, column temp: 35° C., 100 bar): tR=0.97 min (100%); tR (R-enantiomer)=0.72 min (0%)

Step 5

3-Fluoro-5-[(3S)-isoxazolidin-3-yl]benzonitrile

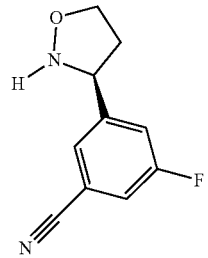 [SMILES: N#Cc1cc(F)cc([C@@H]2CCON2)c1]

To a solution tert-butyl (3S)-3-(3-cyano-5-fluoro-phenyl) isoxazolidine-2-carboxylate (5.00 g, 17.11 mmol) in DCM (100 ml) TFA (14.8 g, 10.0 ml, 129.8 mmol) was added. After 16 hrs at room temperature toluene (10 ml) was added, the reaction mixture was evaporated and stirred with saturated NaHCO₃ solution for 10 minutes. The aqueous phase was extracted two times with ethyl acetate. The organic layer was dried with Na₂SO₄, filtered, evaporated, and purified by silica gel chromatography (column: 220 g SiO₂, eluent: n-heptane and ethyl acetate, gradient: 0% to 100% ethyl acetate in 23 min) to give the title compound (2.64 g, 13.7 mmol, 84% yield).

LC/MS: m/z=193.1 [M+H]⁺; tR: 1.19 min (LC/MS method A).

¹H NMR (400.23 MHz, DMSO-d₆): δ ppm 7.71 (m, 1H), 7.68 (s, 1H), 7.58 (br d, J=10.03 Hz, 1H), 6.62 (br s, 1H), 4.53 (br s, 1H), 3.92 (m, 1H), 3.66 (m, 1H), 2.63 (m, 1H), 2.11 (m, 1H).

Intermediate-02a (3S)-3-(3,5-Difluorophenyl)isoxazolidine

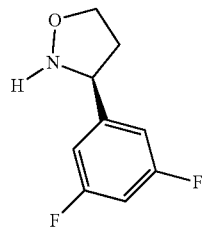 [SMILES: Fc1cc(F)cc([C@@H]2CCON2)c1]

Step 1 tert-Butyl (3S)-3-(3,5-difluorophenyl)isoxazolidine-2-carboxylate

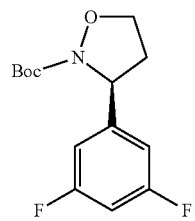 [SMILES: CC(C)(C)OC(=O)N1OCC[C@H]1c1cc(F)cc(F)c1]

The title compound was synthesized in analogy to Intermediate-01 steps 1-4 using 3,5-di-fluoro-benzaldehyde as starting material to give 17 g (59.6 mmol, 79% yield) of the title compound.

LC/MS: m/z=230.1 [M−56+H]$^+$; tR: 0.936 min (LC/MS method C).

$^1$H NMR (400 MHz, CDCl$_3$): δ ppm 6.90 (dd, J=1.9, 8.0 Hz, 2H), 6.70 (tt, J=2.3, 8.9 Hz, 1H), 5.19 (dd, J=5.5, 8.8 Hz, 1H), 4.18 (dt, J=3.6, 7.9 Hz, 1H), 3.94-3.82 (m, 1H), 2.85-2.73 (m, 1H), 2.33-2.19 (m, 1H), 1.49 (s, 9H) SFC (Column: Chiralcel AD-3 50×4.6 mm I.D., 3 µm, gradient: 5% to 40% MeOH (0.05% DEA) in CO$_2$, flow rate: 3 ml/min, column temp: 35° C., 100 bar): tR=0.66 min (100%)

Step 2

(3S)-3-(3,5-Difluorophenyl)isoxazolidine

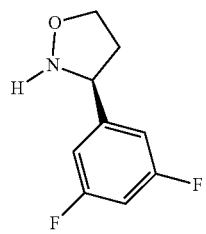 [SMILES: Fc1cc(F)cc([C@@H]2CCON2)c1]

To a solution tert-butyl (3S)-3-(3,5-di-fluoro-phenyl)isoxazolidine-2-carboxylate (5.00 g, 17.53 mmol, 1.0 eq.) in DCM (100 ml) TFA (19.64 g, 15.7 ml, 175.30 mmol, 10.0 eq.) was added. After 16 hrs at room temperature toluene (10 ml) was added, the reaction mixture was evaporated, and stirred with saturated NaHCO$_3$ solution for 10 minutes. The aqueous phase was extracted two times with DCM, the organic layer was dried with Na$_2$SO$_4$, filtered and evaporated to give the title compound (3.24 g, 17.50 mmol, quant.).

LC/MS: m/z=186.0 [M+H]$^+$; tR: 1.32 min (LC/MS method A).

$^1$H NMR (400.23 MHz, DMSO-d$_6$): δ ppm 7.07 (m, 3H), 6.54 (br s, 1H), 4.45 (br s, 1H), 3.90 (m, 1H), 3.66 (m, 1H), 2.61 (m, 1H), 2.08 (m, 1H)

Intermediate-02b (3S)-3-(3-Chloro-5-fluoro-phenyl)isoxazolidine

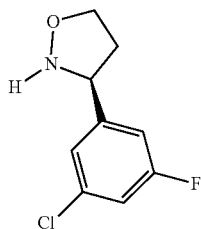 [SMILES: Fc1cc(Cl)cc([C@@H]2CCON2)c1]

The title compound was synthesized using the method described for Intermediate-02a and 3-chloro-5-fluoro-benzaldehyde to give a mixture of enantiomers, which was purified by SFC (column: REGIS (s,s) WHELK-O1, 250×50 mm, 10 µm, eluent 15% EtOH (0.1% NH$_3$H$_2$O) in CO$_2$, single batch cycle process with 3.8 min lag time between two sequential injections, total duration 120 min) to give the title compound (3.9 g, 86% yield) as a yellow oil and 78 mg (1.6% yield) of the R-enantiomer as a yellow oil.

LC/MS: m/z=246.3 [M−56+H]$^+$, tR: 0.900 min (LC/MS method C).

$^1$H NMR (400 MHz, CDCl$_3$): δ ppm 7.16 (s, 1H), 6.95-7.03 (m, 2H), 5.18 (dd, J=5.6, 8.7 Hz, 1H), 4.18 (dt, J=3.5, 8.0 Hz, 1H), 3.87 (dt, J=7.2, 8.6 Hz, 1H), 2.79 (dddd, J=3.5, 7.0, 8.8, 12.3 Hz, 1H), 2.19-2.30 (m, 1H), 1.49 (s, 9H)

SFC (Column: Kromasil (S,S) Whelk-O1 50×4.6 mm I.D., 3.5 µm, gradient: 5% to 40% EtOH (0.05% DEA) in CO$_2$, flow rate: 3 ml/min, column temp: 35° C., 100 bar): tR=1.069 min (100%)

R-Enantiomer:

LC/MS m/z 246.3 [M−56+H]$^+$, tR: 0.890 min (LC/MS method C).

$^1$H NMR (400 MHz, CDCl$_3$): δ ppm 7.16 (s, 1H), 6.96-7.03 (m, 2H), 5.18 (dd, J=5.6, 8.8 Hz, 1H), 4.18 (dt, J=3.6, 7.9 Hz, 1H), 3.83-3.92 (m, 1H), 2.74-2.84 (m, 1H), 2.20-2.31 (m, 1H), 1.49 (s, 9H)

SFC (Column: Kromasil (S,S) Whelk-O1 50×4.6 mm I.D., 3.5 µm, gradient: 5% to 40% EtOH (0.05% DEA) in CO$_2$, flow rate: 3 ml/min, column temp: 35° C., 100 bar): tR=0.890 min (100%)

Intermediate-03

3-Fluoro-5-[(3S)-isoxazolidin-3-yl]-2-methyl-benzonitrile

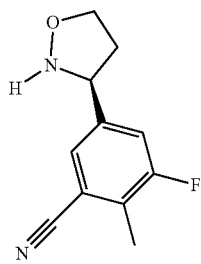

Step 1

5-Bromo-3-fluoro-2-methyl-benzaldehyde

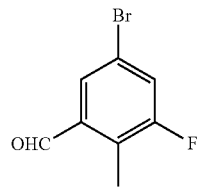

To a solution of 5-bromo-1-fluoro-3-iodo-2-methyl-benzene (5 g, 15.88 mmol, 1 eq.) in THF (50 ml) i-PrMgCl (2 M, 8.73 ml, 1.1 eq.) was added at −60° C., stirred for 15 min, and then DMF (3.48 g, 47.63 mmol, 3.66 ml, 3 eq.) was added. The reaction mixture was stirred at −10° C. for 0.5 hrs. The reaction mixture was quenched with saturated NH$_4$Cl solution (20 ml), and extracted with ethyl acetate (50 ml×3). The combined organic layer was washed with brine (100 ml), dried over Na$_2$SO$_4$, filtered, concentrated under reduced pressure, and purified by silica gel column chromatography (petroleum ether/ethyl acetate=1:0~ 10:1) to give the title compound (3.2 g, 93% yield) as yellow solid.

$^1$H NMR (400 MHz, CDCl$_3$): δ ppm 10.20 (s, 1H), 7.78-7.72 (m, 1H), 7.44 (dd, J=1.9, 8.7 Hz, 1H), 2.53 (d, J=2.1 Hz, 3H)

Step 2

5-Bromo-3-fluoro-2-methyl-benzonitrile

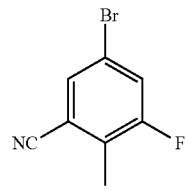

To a solution of 5-bromo-3-fluoro-2-methyl-benzaldehyde (9.5 g, 43.77 mmol, 1 eq.) in EtOH (95 ml) TBHP (5 M in decane, 9.63 ml, 1.1 eq.), 12 (277.74 mg, 1.09 mmol, 0.025 eq.), NH$_4$OAc (5.06 g, 65.66 mmol, 1.5 eq.) and Na$_2$CO$_3$ (4.64 g, 43.77 mmol, 1 eq.) were added, and then the mixture was stirred at 50° C. for 12 hrs. The reaction mixture was quenched with saturated Na$_2$SO$_3$ solution (20 ml), diluted with water (100 ml) and extracted with ethyl acetate (100 ml×3). The combined organic layer was washed with brine (200 ml), dried over Na$_2$SO$_4$, filtered, concentrated under reduced pressure and purified by silica gel column chromatography (petroleum ether/ethyl acatate=1: 0~10:1) to give the title compound (8 g, 85% yield) as yellow solid.

$^1$H NMR (400 MHz, CDCl$_3$): δ ppm 7.59-7.55 (m, 1H), 7.44 (dd, J=1.9, 8.6 Hz, 1H), 2.44 (d, J=2.1 Hz, 3H)

Step 3

5-[(E)-3,3-Diethoxyprop-1-enyl]-3-fluoro-2-methyl-benzonitrile

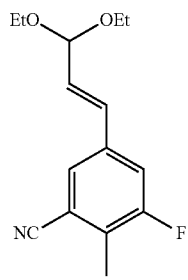

A mixture of 5-bromo-3-fluoro-2-methyl-benzonitrile (10.1 g, 47.19 mmol, 1 eq.), 3,3-diethoxyprop-1-ene (18.43 g, 141.57 mmol, 21.58 ml, 3 eq.), Pd(t-Bu$_3$P)$_2$ (1.21 g, 2.36 mmol, 0.05 eq.) and triethylamine (14.32 g, 141.57 mmol, 19.70 ml, 3 eq.) in DMF (100 ml) was stirred at 80° C. under N$_2$ atmosphere for 12 hrs. The reaction mixture was concentrated under reduced pressure. The residue was diluted with water (100 ml) and extracted with ethyl acetate (100 ml×3). The combined organic layer was washed with brine (100 ml×3), dried over Na$_2$SO$_4$, filtered and concentrated under reduced pressure to give the title compound (13 g, crude).

Step 4

3-Fluoro-2-methyl-5-[(E)-3-oxoprop-1-enyl]benzonitrile

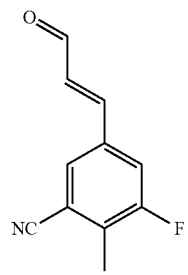

A mixture of 5-[(E)-3,3-diethoxyprop-1-enyl]-3-fluoro-2-methyl-benzonitrile (13 g, crude) in HCl (1 M, 94.38 ml, 2 eq.) and acetone (80 ml) was stirred at 25° C. for 0.5 hrs. The mixture was adjusted with saturated NaHCO$_3$ solution to pH 7-8 and extracted with ethyl acetate (100 ml×3). The combined organic layer was washed with brine (100 ml), dried over Na$_2$SO$_4$, filtered, concentrated under reduced pressure and purified by silica gel column chromatography (petroleum ether/ethyl acetate=1:0 to 3:1) to give the title compound (5.5 g, 62% yield) as yellow solid.

¹H NMR (400 MHz, CDCl₃): δ ppm 9.74 (d, J=7.5 Hz, 1H), 7.60 (s, 1H), 7.46 (dd, J=1.5, 9.7 Hz, 1H), 7.38 (d, J=16.0 Hz, 1H), 6.70 (dd, J=7.4, 16.1 Hz, 1H), 2.53 (d, J=2.1 Hz, 3H)

Step 5 tert-Butyl (3S)-3-(3-cyano-5-fluoro-4-methyl-phenyl)-5-hydroxy-isoxazolidine-2-carboxylate

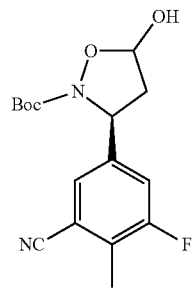

To a solution of [diphenyl-[(2S)-pyrrolidin-2-yl]methoxy]-trimethyl-silane (1.82 g, 5.60 mmol, 0.2 eq.) in CHCl₃ (53 ml) 3-fluoro-2-methyl-5-[(E)-3-oxoprop-1-enyl]benzonitrile 3-fluoro-2-methyl-5-[(E)-3-oxoprop-1-enyl]benzonitrile (5.3 g, 28.01 mmol, 1 eq.) was added at 0° C., the mixture was stirred at 0° C. for 30 min and tert-butyl N-hydroxycarbamate (4.48 g, 33.62 mmol, 1.2 eq.) was added at 0° C. The mixture was warmed to 20° C. smoothly and stirred for 12 hrs. The reaction mixture was concentrated under reduced pressure and purified by preparative reversed-phase HPLC (column: Welch Ultimate XB_C18, 20-40 μm; 120 Å, I.D. 95×H365 mm, eluent: water (0.1% formic acid) and acetonitrile, gradient: 20% to 50% acetonitrile in 30 min and 50% acetonitrile for 20 min, flow: 200 ml/min) to give the title compound (5.8 g, 64% yield) as yellow solid.

LC/MS: m/z=205.2 [M−100−18+H]⁺; tR: 0.896 min (LC/MS method C).

¹H NMR (400 MHz, CDCl₃): δ ppm 7.40 (s, 1H), 7.27 (s, 1H), 5.86 (d, J=4.3 Hz, 1H), 5.28 (t, J=8.2 Hz, 1H), 2.80 (dd, J=8.5, 12.5 Hz, 1H), 2.46 (d, J=2.0 Hz, 3H), 2.19 (ddd, J=4.3, 8.1, 12.5 Hz, 1H), 1.51-1.42 (m, 9H)

Step 6 tert-Butyl N-[(1S)-1-(3-cyano-5-fluoro-4-methyl-phenyl)-3-hydroxy-propyl]-N-hydroxy-carbamate

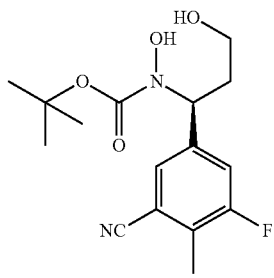 [SMILES: Cc1c(F)cc([C@H](CCO)N(O)C(=O)OC(C)(C)C)cc1C#N]

To a solution of tert-butyl (3S)-3-(3-cyano-5-fluoro-4-methyl-phenyl)-5-hydroxy-isoxazolidine-2-carboxylate (4.8 g, 14.89 mmol, 1 eq.) in MeOH (48 ml) NaBH₄ (619.68 mg, 16.38 mmol, 1.1 eq.) was added at 0° C. The reaction mixture was stirred at 0° C. for 1 hr, quenched with saturated NH₄Cl solution (20 ml) and extracted with ethyl acetate (100 ml×3). The combined organic layer was washed with brine (200 ml), dried over Na₂SO₄, filtered, concentrated under reduced pressure and purified by silica gel column chromatography (petroleum ether/ethyl acetate=1:0 to 0:1) to give the title compound (3.6 g, 73% yield) as white solid. It was triturated with petroleum ether/ethyl acetate (3:1, 50 ml) to give 2.7 g filter cake as white solid and 1.1 g filtrate as yellow solid.

¹H NMR (400 MHz, CDCl₃): δ ppm 7.46 (s, 1H), 7.40-7.33 (m, 1H), 6.75 (br s, 1H), 5.22 (dd, J=5.1, 10.8 Hz, 1H), 3.93-3.73 (m, 2H), 2.46 (d, J=2.0 Hz, 3H), 2.37 (dddd, J=3.4, 7.5, 10.9, 14.6 Hz, 1H), 2.12 (br s, 1H), 1.48 (s, 9H)

Step 7 tert-Butyl (3S)-3-(3-cyano-5-fluoro-4-methyl-phenyl)isoxazolidine-2-carboxylate

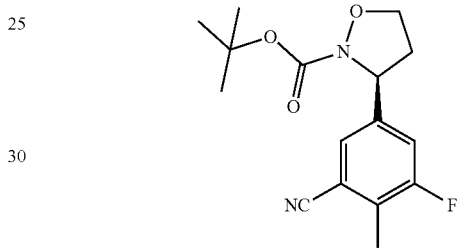

To a solution of tert-butyl N-[(1S)-1-(3-cyano-5-fluoro-4-methyl-phenyl)-3-hydroxy-propyl]-N-hydroxy-carbamate (2.7 g, 8.32 mmol, 1 eq.) in THF (27 ml) n-Bu₃P (2.69 g, 13.32 mmol, 3.29 ml, 1.6 eq.) and DIAD (2.19 g, 10.82 mmol, 2.10 ml, 1.3 eq.) were added at 0° C. The mixture was warmed to 25° C. smoothly and stirred for 12 hrs under N₂ atmosphere. The reaction was concentrated under reduced pressure and purified by preparative reversed-phase HPLC (column: Welch Ultimate XB_C18 20-40 μm; 120 Å, I.D. 75×H348 mm, eluent: water (0.1% formic acid) and acetonitrile, gradient: 10% to 65% acetonitrile in 28 min, 65% acetonitrile for 5 min, flow: 200 ml/min) and silica gel column chromatography (petroleum ether/ethyl acetate=1:0~ 0:1) to give the title compound (2 g, 78% yield, 94.1% e.e.) as white solid. The product was further separated by SFC (column: DAICEL CHIRALPAK AD, 250×30 mm, 10 μm; mobile phase: 25% methanol (0.1% NH₃H₂O) in CO₂, single batch cycle process with 3.0 min lag time between two sequential injections, total duration 75 min) to give the title compound (1.7 g, 85% yield, >99.9% e.e.) as off-white solid.

LC/MS: m/z=251.1 [M−56+H]⁺; tR: 0.949 min (LC/MS method C).

¹H NMR (400 MHz, CDCl₃): δ ppm 7.41 (s, 1H), 7.29 (dd, J=1.4, 10.0 Hz, 1H), 5.20 (dd, J=5.6, 8.8 Hz, 1H), 4.18 (dt, J=3.4, 8.0 Hz, 1H), 3.88 (dt, J=7.2, 8.7 Hz, 1H), 2.81 (dddd, J=3.4, 7.0, 8.8, 12.3 Hz, 1H), 2.45 (d, J=2.0 Hz, 3H), 2.23 (dddd, J=5.5, 7.8, 9.1, 12.3 Hz, 1H), 1.49 (s, 9H)

SFC (Column: Chiralcel AD-3 50×4.6 mm I.D., 3 μm, gradient: 5% to 40% MeOH (0.05% DEA) in CO₂, flow rate: 3 ml/min, column temp: 35° C., 100 bar): tR=1.22 min (100%); tR (R-enantiomer)=0.86 min (0%)

Step 8

3-Fluoro-5-[(3S)-isoxazolidin-3-yl]-2-methyl-benzonitrile

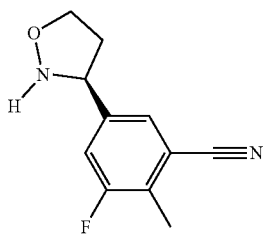

To a solution tert-butyl (3S)-3-(3-cyano-5-fluoro-4-methyl-phenyl)isoxazolidine-2-carboxylate (1.36 g, 4.44 mmol, 1.0 eq.) in DCM (40 ml) TFA (4.975 g, 3.974 ml, 44.40 mmol, 10.0 eq.) was added. After 16 hrs at room temperature toluene (5 ml) was added, the reaction mixture was evaporated and stirred with saturated NaHCO₃ solution for 10 minutes. The aqueous phase was extracted with DCM (10 ml×2), the organic layer was dried with Na₂SO₄, filtered and evaporated to give the title compound (860 mg, 4.17 mmol, 94% yield).

¹H NMR (400.23 MHz, DMSO-$d_6$): δ ppm 7.62 (s, 1H), 7.52 (br d, J=10.64 Hz, 1H), 6.55 (br s, 1H), 4.47 (br s, 1H), 3.90 (td, J=7.95, 7.95, 5.14 Hz, 1H), 3.67 (br s, 1H), 2.60 (m, 1H), 2.36 (d, J=1.83 Hz, 3H), 2.09 (m, 1H)

Intermediate-04

Methyl 1-(6-chloropyrimidin-4-yl)piperidine-4-carboxylate

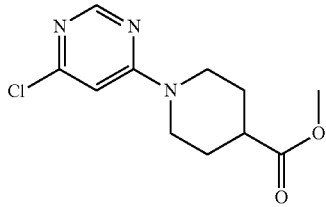 [SMILES: COC(=O)C1CCN(c2cc(Cl)ncn2)CC1]

A mixture of 4,6-dichloropyrimidine (80 g, 536.99 mmol, 1 eq.), methyl piperidine-4-carboxylate (96.47 g, 536.99 mmol, 1 eq., HCl), DIEA (208.21 g, 1.61 mol, 280.60 ml, 3 eq.) in n-BuOH (700 ml) was degassed and purged with N₂, and then the mixture was stirred at 80° C. for 2 hrs under N₂ atmosphere. The reaction mixture was concentrated under reduced pressure to remove n-BuOH. Then diluted with H₂O (100 ml) and EA (200 ml), adjusted to pH 6 with 1 N HCl solution and extracted with ethyl acetate (200 ml×3). The combined organic layer was washed with NaHCO₃ aqueous solution (500 ml), brine (500 ml), dried over Na₂SO₄, filtered and concentrated to give the title compound (135.4 g crude, 529.53 mmol, 97% yield) as a yellow solid.

LC/MS: m/z=256.1 [M+H]⁺; tR: 0.737 min (LC/MS method C).

¹H NMR (400 MHz, DMSO-$d_6$): δ ppm 8.32 (s, 1H), 6.97 (s, 1H), 4.38-4.19 (m, 2H), 3.62 (s, 3H), 3.16-3.02 (m, 2H), 2.71 (tt, J=4.0, 10.8 Hz, 1H), 1.96-1.84 (m, 2H), 1.60-1.44 (m, 2H)

Intermediate-05

1-[6-(2-Methylimidazol-1-yl)pyrimidin-4-yl]piperidine-4-carboxylic acid

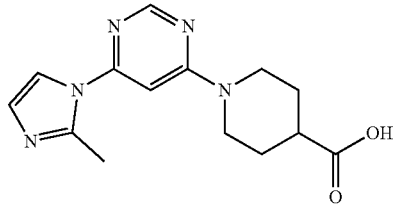 [SMILES: Cc1nccn1-c1cc(N2CCC(C(=O)O)CC2)ncn1]

Step 1

Methyl 1-[6-(2-methylimidazol-1-yl)pyrimidin-4-yl]piperidine-4-carboxylate

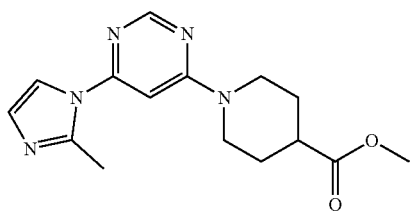 [SMILES: COC(=O)C1CCN(c2cc(-n3ccnc3C)ncn2)CC1]

A mixture of Intermediate-04 (3.97 g, 15.53 mmol, 1 eq.), 2-methyl-1H-imidazole (2.55 g, 31.05 mmol, 2 eq.), K₂CO₃ (8.58 g, 62.10 mmol, 4 eq.) and CuI (1.48 g, 7.76 mmol, 0.5 eq.) in DMSO (40 ml) was degassed and purged with N₂ for 3 times. The mixture was stirred at 120° C. for 12 hrs under N₂ atmosphere. The reaction mixture was filtered, diluted with water (400 ml) and extracted with ethyl acetate (200 ml×3). The combined organic layer was washed with brine (300 ml), dried over Na₂SO₄, filtered, concentrated and purified by flash silica gel chromatography (eluent: petroleum ether and ethyl acetate, gradient: 35% to 70% ethyl acetate and eluent: MeOH and DCM, gradient, 5% to 15% MeOH) to give the title compound (2.3 g, 7.63 mmol, 49% yield) as a yellow oil.

LC/MS: m/z=302.1 [M+H]⁺; tR: 0.615 min (LC/MS method C).

¹H NMR (400 MHz, CDCl₃): δ ppm 8.54 (s, 1H), 7.30 (s, 1H), 7.04 (s, 1H), 6.41 (s, 1H), 4.32 (br d, J=13.1 Hz, 2H), 3.73 (s, 3H), 3.18 (ddd, J=3.0, 11.0, 13.7 Hz, 2H), 2.67 (s, 3H), 2.08-2.03 (m, 2H), 1.84-1.74 (m, 3H)

Step 2

1-[6-(2-Methylimidazol-1-yl)pyrimidin-4-yl]piperidine-4-carboxylic acid

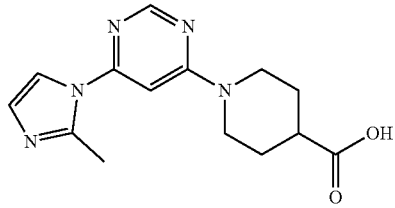 [SMILES: Cc1nccn1-c1cc(N2CCC(C(=O)O)CC2)ncn1]

To a solution of methyl 1-[6-(2-methylimidazol-1-yl)pyrimidin-4-yl]piperidine-4-carboxylate (4.46 g, 14.80 mmol, 1 eq.) in THF (50 ml) LiOH·H₂O (1 M, 29.60 ml, 2 eq.) was added. The mixture was stirred at 20° C. for 1 hr. The reaction mixture was adjusted to pH 3 with 4 N HCl aqueous solution, the mixture was concentrated in vacuo and purified by reversed-phase HPLC (column: Welch Ultimate XB_C18, 20-40 μm, 120 Å; eluent: water (0.1% formic acid) and acetonitrile, gradient: 100% to 10% acetonitrile in 20 min, 10% acetonitrile for 20 min, flow: 100 ml/min) to give the title compound (3.5 g, 10.81 mmol, 73% yield, HCl) as a yellow solid.

LC/MS: m/z=288.2 [M+H]⁺; tR: 0.700 min (LC/MS method D).

¹H NMR (400 MHz, D₂O): δ ppm 8.50 (s, 1H), 7.70 (d, J=2.3 Hz, 1H), 7.47 (d, J=2.2 Hz, 1H), 7.08 (s, 1H), 4.34-4.17 (m, 2H), 3.34-3.26 (m, 2H), 2.83-2.76 (m, 1H), 2.73 (s, 3H), 2.06 (br dd, J=3.4, 13.5 Hz, 2H), 1.75-1.65 (m, 2H)

Intermediate-06

1-[6-(2-Methylpyrazol-3-yl)pyrimidin-4-yl]piperidine-4-carboxylic acid

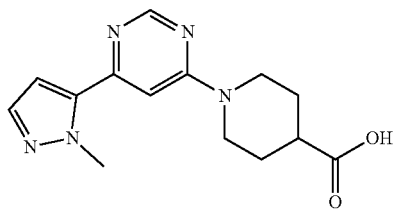 [SMILES: Cn1nccc1-c1cc(N2CCC(C(=O)O)CC2)ncn1]

Step 1

Methyl 1-[6-(2-methylpyrazol-3-yl)pyrimidin-4-yl]piperidine-4-carboxylate

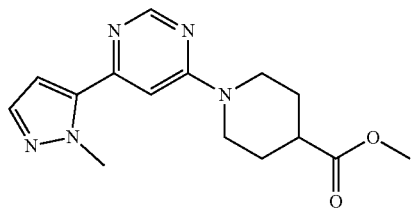 [SMILES: COC(=O)C1CCN(c2cc(-c3ccnn3C)ncn2)CC1]

To a solution of Intermediate-04 (25 g, 97.77 mmol, 1 eq.) in dioxane (200 ml) and H₂O (40 ml) K₂CO₃ (27.03 g, 195.54 mmol, 2 eq.), 1-methyl-5-(4,4,5,5-tetramethyl-1,3,2-dioxaborolan-2-yl)pyrazole (20.34 g, 97.77 mmol, 1 eq.) and Pd(dppf)Cl₂ (7.15 g, 9.78 mmol, 0.1 eq.) were added. The mixture was stirred at 120° C. for 2 hrs under N₂ atmosphere. The residue was diluted with H₂O (200 ml) and extracted with ethyl acetate (300 ml×2). The combined organic layer was dried over Na₂SO₄, filtered, concentrated under reduced pressure and purified by flash silica gel chromatography (column: 220 g SepaFlash® Silica Flash, eluent: petroleum ether and ethyl acetate, gradient: 0% to 20% ethyl acetate, flow: 100 ml/min) to give the title compound (29.3 g, 86.44 mmol, 88% yield) as a yellow oil.

LC/MS: m/z=302.1 [M+H]⁺; tR: 0.644 min (LC/MS method C).

Step 2

1-[6-(2-Methylpyrazol-3-yl)pyrimidin-4-yl]piperidine-4-carboxylic acid

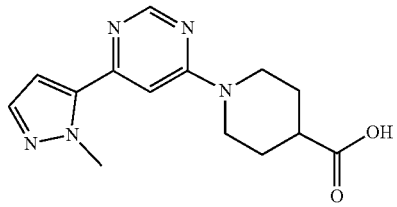 [SMILES: Cn1nccc1-c1cc(N2CCC(C(=O)O)CC2)ncn1]

To a solution of methyl 1-[6-(2-methylpyrazol-3-yl)pyrimidin-4-yl]piperidine-4-carboxylate (29.3 g, 97.23 mmol, 1 eq.) in THF (250 ml) and H₂O (50 ml) LiOH·H₂O (12.24 g, 291.69 mmol, 3 eq.) was added. The mixture was stirred at 25° C. for 12 hrs, adjusted to pH 5 with 1 N HCl solution, concentrated under reduced pressure and filtered. The filter cake was washed with H₂O (50 ml) and triturated with ethyl acetate at 20° C. for 1 hr to give compound the title compound (19.4 g, 64.89 mmol, 67% yield) as a gray solid.

LC/MS: m/z=288.4 [M+H]⁺; tR: 0.295 min (LC/MS method C).

¹H NMR (400 MHz, DMSO-d₆): δ ppm 12.30 (s, 1H), 8.57 (d, J=0.9 Hz, 1H), 7.48 (d, J=2.0 Hz, 1H), 7.13 (d, J=0.9 Hz, 1H), 6.95 (d, J=2.0 Hz, 1H), 4.37 (d, J=12.6 Hz, 2H), 4.14 (s, 3H), 3.17-3.02 (m, 2H), 2.64-2.54 (m, 1H), 1.97-1.83 (m, 2H), 1.58-1.41 (m, 2H)

Intermediate-07

1-[6-(4-Cyclopropyl-2-methyl-imidazol-1-yl)pyrimidin-4-yl]piperidine-4-carboxylic acid

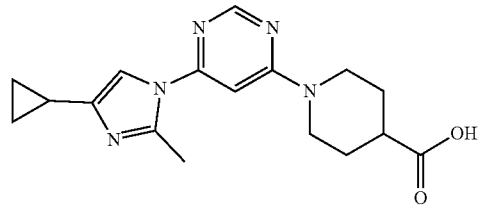 [SMILES: Cc1nc(C2CC2)cn1-c1cc(N2CCC(C(=O)O)CC2)ncn1]

Step 1

4-Cyclopropyl-2-methyl-1H-imidazole

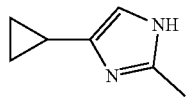

To a solution of acetamidine (10.3 g, 108.94 mmol, 5 eq., HCl) in MeOH (100 ml) NaOH (4.36 g, 108.94 mmol, 5 eq.) was added at 0° C. The mixture was stirred at 25° C. for 3 hrs. The reaction mixture was filtered, the filtrate was concentrated in vacuum and the residue was dissolved in acetonitrile (60 ml). At 25° C. a solution of K₂CO₃ (6.02 g, 43.58 mmol, 2 eq.) in H₂O (30 ml) and a solution of 2-bromo-1-cyclopropyl-ethanone (3.55 g, 21.79 mmol, 1 eq.) in acetonitrile (10 ml) were added and stirred at 25° C. for 12 hrs. The reaction mixture was concentrated under reduced pressure and filtered. The filter cake was washed with water to give the title compound as crude product (1.5 g, 12.28 mmol, 56% yield) as a white solid, which was used for next step directly.

¹H NMR: (400 MHz, CDCl₃): δ ppm 9.43-8.77 (m, 1H), 6.52 (s, 1H), 2.28 (s, 3H), 1.79-1.66 (m, 1H), 0.79-0.69 (m, 2H), 0.63-0.55 (m, 2H)

Step 2

Methyl 1-[6-(4-cyclopropyl-2-methyl-imidazol-1-yl)pyrimidin-4-yl]piperidine-4-carboxylate

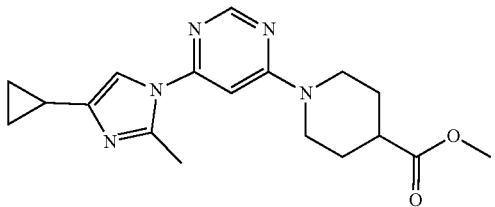 [SMILES: COC(=O)C1CCN(c2cc(-n3cc(C4CC4)nc3C)ncn2)CC1]

To a solution of 4-cyclopropyl-2-methyl-1H-imidazole (573.33 mg, 4.69 mmol, 1.2 eq.) in DMF (10 ml) Cs₂CO₃ (2.55 g, 7.82 mmol, 2 eq.) and Intermediate-04 (1 g, 3.91 mmol, 1 eq.) were added under N₂ atmosphere. The reaction mixture was stirred at 120° C. for 12 hrs and cooled to 25° C. MeI (275 mg, 19.5 mmol, 5 eq.) was added, the reaction mixture was kept under N₂ at 25° C. for 2 hrs, poured into saturated NaHCO₃ aqueous solution (100 ml) and extracted with ethyl acetate (50 ml×3). The combined organic layer was washed with brine (50 ml), dried over Na₂SO₄, filtered, concentrated and purified by silica gel column chromatography (eluent: petroleum ether and ethyl acetate, gradient: 10/1 to 0/1) to give the title compound (1 g, crude) as a yellow oil.

LC/MS: m/z=342.3 [M+H]⁺; tR: 0.739 min (LC/MS method C).

Step 3

1-[6-(4-Cyclopropyl-2-methyl-imidazol-1-yl)pyrimidin-4-yl]piperidine-4-carboxylic acid

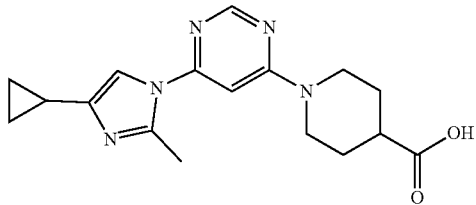 [SMILES: Cc1nc(C2CC2)cn1-c1cc(N2CCC(C(=O)O)CC2)ncn1]

To a solution of methyl 1-[6-(4-cyclopropyl-2-methyl-imidazol-1-yl)pyrimidin-4-yl]piperidine-4-carboxylate (900 mg, 2.64 mmol, 1 eq.) in THF (4 ml) and H₂O (4 ml) LiOH·H₂O (331.87 mg, 7.91 mmol, 3 eq.) was added under N₂ atmosphere. The reaction mixture was stirred at 25° C. for 12 hrs, was adjusted to pH 4 with 1 N HCl solution and extracted with ethyl acetate (50 ml×3). The combined organic layer was washed with brine (100 ml), dried over Na₂SO₄, filtered and concentrated. The residue was purified by reversed-phase HPLC (column: 330 g Flash Column Welch Ultimate XB_C18 20-40 μm, 120 Å, eluent: water (0.1% HCl) and acetonitrile, gradient: 0% to 20% acetonitrile in in 20 min, 20% acetonitrile for 10 min, flow: 100 ml/min) and triturated with petroleum ether/ethyl acetate (1:1, 7 ml) at 25° C. to give the title compound (540 mg, 1.62 mmol, 53% yield) as a white solid.

LC/MS: m/z=328.2 [M+H]⁺; tR: 0.685 min (LC/MS method C).

¹H NMR (400 MHz, DMSO-d₆): δ ppm 8.54 (s, 1H), 7.94 (s, 1H), 7.13 (s, 1H), 4.45-4.35 (m, 2H), 3.24-3.11 (m, 2H), 2.81 (s, 3H), 2.70-2.60 (m, 1H), 2.07-1.84 (m, 3H), 1.62-1.41 (m, 2H), 1.09-0.98 (m, 2H), 0.93-0.83 (m, 2H)

Intermediate-08

3-[(3S)-2-[1-(6-Chloropyrimidin-4-yl)piperidine-4-carbonyl]isoxazolidin-3-yl]-5-fluoro-benzonitrile

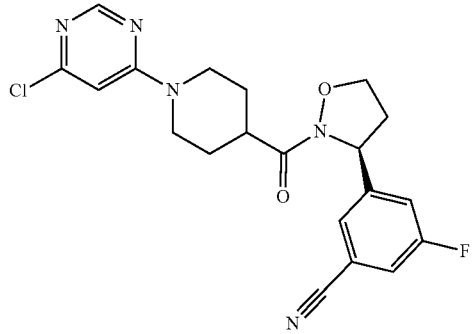 [SMILES: N#Cc1cc(F)cc([C@@H]2CCON2C(=O)C2CCN(c3cc(Cl)ncn3)CC2)c1]

Step 1:

1-(6-Chloropyrimidin-4-yl)piperidine-4-carboxylic acid

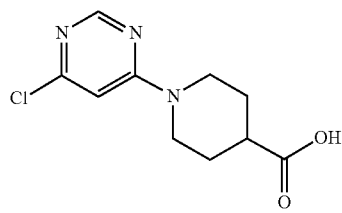 [SMILES: O=C(O)C1CCN(c2cc(Cl)ncn2)CC1]

To a mixture of Intermediate-04 (3 g, 11.73 mmol, 1 eq.) in THF (10 ml) and H₂O (10 ml) LiOH·H₂O (1 M, 23.46 ml, 2 eq.) was added and the reaction mixture was stirred at 25° C. for 1 hr. The reaction mixture was adjusted to pH 3-4 with 1 M HCl, filtered and concentrated under reduced pressure to give the title compound (2.43 g, 86% yield), which was used directly in the next step.

LC/MS: m/z=242.0 [M+H]⁺; tR: 0.835 min (LC/MS method D).

¹H NMR (400 MHz, DMSO-d₆): δ ppm 12.43-12.20 (m, 1H), 8.32 (s, 1H), 6.97 (s, 1H), 4.37-4.14 (m, 2H), 3.16-3.05 (m, 2H), 2.62-2.55 (m, 1H), 1.88 (br dd, J=13.5, 3.5 Hz, 2H), 1.55-1.42 (m, 2H)

Step 2:

3-[(3S)-2-[1-(6-Chloropyrimidin-4-yl)piperidine-4-carbonyl]isoxazolidin-3-yl]-5-fluoro-benzonitrile

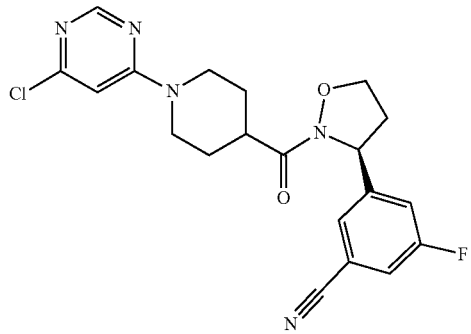 [SMILES: N#Cc1cc(F)cc([C@@H]2CCON2C(=O)C2CCN(c3cc(Cl)ncn3)CC2)c1]

To a solution of 1-(6-chloropyrimidin-4-yl)piperidine-4-carboxylic acid (4 g, 16.55 mmol, 1 eq.), 3-fluoro-5-[(3S)-isoxazolidin-3-yl]benzonitrile (3.97 g, 17.38 mmol, 1.05 eq., HCl) in DMF (40 ml) HATU (12.59 g, 33.10 mmol, 2 eq.) and DIEA (10.70 g, 82.76 mmol, 14.41 ml, 5 eq.) were added. The reaction mixture was stirred at 25° C. for 12 hrs. The reaction mixture was filtered, concentrated under reduced pressure and purified by column chromatography (SiO$_2$, petroleum ether/ethyl acetate=4/1 to 3/1) to give the title compound (4 g, 58% yield) as a brown solid.

LC/MS: m/z=214.0 [M+H]$^+$; tR: 0.637 min (LC/MS method C).

$^1$H NMR (400 MHz, CDCl$_3$): δ ppm 8.39 (s, 1H), 7.42 (s, 1H), 7.31-7.29 (m, 1H), 7.27 (br d, J=1.6 Hz, 1H), 6.55 (s, 1H), 5.42 (dd, J=8.8, 6.4 Hz, 1H), 4.35 (td, J=7.9, 3.0 Hz, 3H), 4.01-3.89 (m, 1H), 3.21-3.08 (m, 4H), 2.99-2.90 (m, 1H), 2.41-2.30 (m, 1H), 2.14-2.07 (m, 1H), 1.89-1.76 (m, 3H)

SFC (Column: Chiralcel OJ-3 50×4.6 mm I.D., 3 μm, gradient: 5% to 40% MeOH (0.05% DEA) in CO$_2$, flow rate: 3 ml/min, column temp: 35° C., 100 bar): tR=1.42 min (100%)

Intermediate-09

1-[6-(5-Methyl-1,2,4-triazol-1-yl)pyrimidin-4-yl]piperidine-4-carboxylic acid

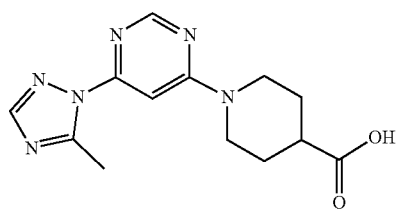 [SMILES: Cc1ncnn1-c1cc(N2CCC(C(=O)O)CC2)ncn1]

Step 1

Methyl 1-(6-hydrazinopyrimidin-4-yl)piperidine-4-carboxylate

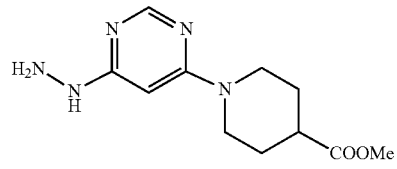 [SMILES: COC(=O)C1CCN(c2cc(NN)ncn2)CC1]

To a solution of Intermediate-04 (1 g, 3.91 mmol, 1 eq.) in i-PrOH (10 ml) DIEA (1.01 g, 7.82 mmol, 1.36 ml, 2 eq.) and N$_2$H$_4$·H$_2$O (253.36 mg, 4.30 mmol, 245.98 μl, 85% purity, 1.1 eq.) were added. The mixture was stirred at 80° C. for 12 hrs and diluted with water (50 ml) and extracted with ethyl acetate (30 ml×3). The combined organic layer was washed with brine (50 ml×2), dried over Na$_2$SO$_4$, filtered and concentrated to give the title compound (980 mg, crude) as a white solid.

LC/MS: m/z=252.3 [M+H]$^+$; tR: 0.703 min (LC/MS method D).

Step 2

Methyl 1-[6-(5-methyl-1,2,4-triazol-1-yl)pyrimidin-4-yl]piperidine-4-carboxylate

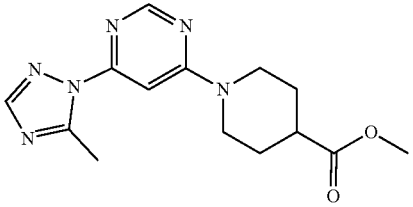 [SMILES: COC(=O)C1CCN(c2cc(-n3ncnc3C)ncn2)CC1]

To a solution of methyl 1-(6-hydrazinopyrimidin-4-yl)piperidine-4-carboxylate (980 mg, 3.90 mmol, 1 eq.) and p-toluenesulfonic acid (671.57 mg, 3.90 mmol, 1 eq.) in EtOH (10 ml) N-(dimethylaminomethylene)acetamide (890.33 mg, 7.80 mmol, 2 eq.) was added at 25° C. The reaction mixture was stirred at 80° C. for 2 hrs and concentrated to remove most of the solvent. NaHCO$_3$ saturated aqueous solution (30 ml) was added and the aqueous layer was extracted with ethyl acetate (20 ml×2). The organic layer was washed with brine (50 ml), dried over Na$_2$SO$_4$, filtered, concentrated and purified by flash silica gel chromatography (column: 20 g SepaFlash® Silica Flash Column, eluent: petroleum ether and ethyl acetate, gradient: 10% to 40% ethyl acetate, flow: 60 ml/min) to give the title compound (475 mg, 1.56 mmol, 40% yield) as a white solid.

LC/MS: m/z=303.2 [M+H]$^+$; tR: 0.799 min (LC/MS method C).

$^1$H NMR (400 MHz, CDCl$_3$): δ ppm 8.51 (s, 1H), 7.90 (s, 1H), 7.07 (s, 1H), 4.45-4.31 (m, 2H), 3.72 (s, 3H), 3.17 (br t, J=11.9 Hz, 2H), 2.92 (s, 3H), 2.70-2.61 (m, 1H), 2.03 (br s, 1H), 1.77 (q, J=10.4 Hz, 2H)

Step 3

1-[6-(5-Methyl-1,2,4-triazol-1-yl)pyrimidin-4-yl] piperidine-4-carboxylic acid

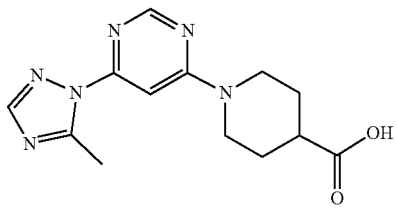 [SMILES: Cc1ncnn1-c1cc(N2CCC(C(=O)O)CC2)ncn1]

To a solution of methyl 1-[6-(5-methyl-1,2,4-triazol-1-yl) pyrimidin-4-yl]piperidine-4-carboxylate (475 mg, 1.57 mmol, 1 eq.) in THF (5 ml) LiOH·H$_2$O (1 M, 3.14 ml, 2 eq.) was added. The mixture was stirred at 25° C. for 1 hr, adjusted to pH 3 with 1 N HCl aqueous solution, concentrated to remove most of the solvent and filtered. The filter cake was collected and dried to give the title compound (470 mg, crude) as a white solid.

LC/MS: m/z=289.0 [M+H]$^+$; tR: 0.729 min (LC/MS method C).

$^1$H NMR (400 MHz, DMSO-d$_6$): δ ppm 12.31 (br s, 1H), 8.51 (s, 1H), 8.09 (s, 1H), 7.08 (s, 1H), 4.31 (br d, J=2.3 Hz, 2H), 3.15 (br t, J=11.1 Hz, 2H), 2.77 (s, 3H), 2.60 (ddd, J=4.1, 6.8, 10.7 Hz, 1H), 1.91 (br dd, J=3.2, 13.2 Hz, 2H), 1.57-1.47 (m, 2H)

Intermediate-10

1-[6-(3-Methyl-1,2,4-triazol-1-yl)pyrimidin-4-yl] piperidine-4-carboxylic acid

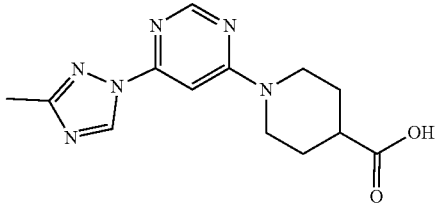 [SMILES: Cc1ncn(-c2cc(N3CCC(C(=O)O)CC3)ncn2)n1]

Step 1

Methyl 1-[6-(3-methyl-1,2,4-triazol-1-yl)pyrimidin-4-yl]piperidine-4-carboxylate

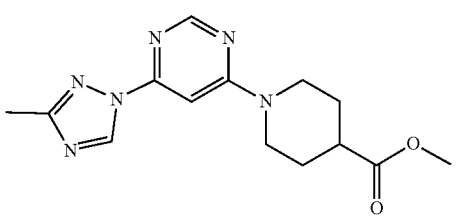

To a solution of 5-methyl-1H-1,2,4-triazole (1.17 g, 14.08 mmol, 1.2 eq.) in DMF (30 ml) Cs$_2$CO$_3$ (7.65 g, 23.46 mmol, 2 eq.), Intermediate-04 (3 g, 11.73 mmol, 1 eq.) and Molecular sieve 4 Å (3 g, 11.73 mmol, 1 eq.) were added under N$_2$ atmosphere. The reaction mixture was stirred at 120° C. for 12 hrs and cooled to 25° C. MeI (833 mg, 58.6 mmol, 5 eq.) was added and the reaction mixture was kept under N$_2$ atmosphere at 25° C. for 2 hrs. The reaction mixture was filtered, diluted with water (300 ml) and extracted with ethyl acetate (200 ml×3). The combined organic layer was washed with brine (300 ml×2), dried over Na$_2$SO$_4$, filtered, concentrated and purified by preparative HPLC (column: Welch Ultimate XB-CN 250×50 mm, 10 μm, eluent: 2% EtOH (0.1% formic acid) in hexane, 18 min) to give the title compound as a mixture with the biproduct methyl 1-[6-(5-methyl-1,2,4-triazol-1-yl)pyrimidin-4-yl]piperidine-4-carboxylate (Intermediate-09, step 2) (5 g, 15.05 mmol, 87% yield) as a white solid.

$^1$H NMR (400 MHz, CDCl$_3$): δ ppm 9.05 (s, 1H), 8.52 (s, 1H), 7.93 (s, 1H), 7.08 (s, 1H), 4.42-4.32 (m, 2H), 3.72 (s, 3H), 3.22-3.15 (m, 2H), 2.94 (s, 3H), 2.70-2.64 (m, 1H), 2.05 (br dd, J=2.8, 13.8 Hz, 2H), 1.82-1.78 (m, 2H)

Step 2

1-[6-(3-Methyl-1,2,4-triazol-1-yl)pyrimidin-4-yl] piperidine-4-carboxylic acid

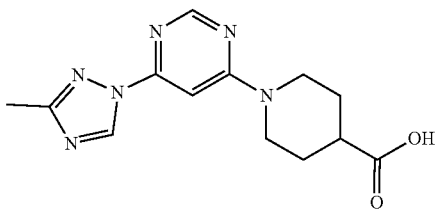 [SMILES: Cc1ncn(-c2cc(N3CCC(C(=O)O)CC3)ncn2)n1]

To a solution of methyl 1-[6-(3-methyl-1,2,4-triazol-1-yl) pyrimidin-4-yl]piperidine-4-carboxylate and byproduct methyl 1-[6-(5-methyl-1,2,4-triazol-1-yl)pyrimidin-4-yl]piperidine-4-carboxylate (4.9 g, 16.21 mmol, 1 eq.) in THF (50 ml) LiOH·H$_2$O (1 M, 32.41 ml, 2 eq.) was added. The mixture was stirred at 25° C. for 1 hr, adjusted to pH 3 with 1 N HCl aqueous solution, concentrated to remove most of solvent and filtered. The filter cake was re-crystallized from DMF (50 ml) at 80° C. for 1 hr and filtered to give the title compound (4 g, 13.87 mmol, 86% yield) as a white solid.

LC/MS: m/z=289 [M+H]$^+$; tR: 0.649 min (LC/MS method C).

$^1$H NMR (400 MHz, CDCl$_3$): δ ppm 12.35 (br s, 1H), 9.20 (s, 1H), 8.45 (s, 1H), 6.99 (s, 1H), 4.33 (br dd, J=4.6, 2.1 Hz, 2H), 3.15 (br t, J=11.5 Hz, 2H), 2.66-2.56 (m, 1H), 2.39 (s, 3H), 1.98-1.87 (m, 2H), 1.60-1.46 (m, 2H)

Intermediate-11a

Methyl 1-(6-chloro-5-fluoro-pyrimidin-4-yl)piperidine-4-carboxylate

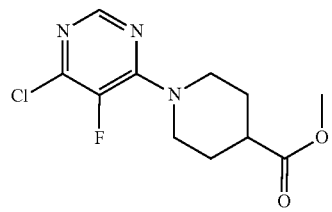 [SMILES: COC(=O)C1CCN(c2ncnc(Cl)c2F)CC1]

A mixture of 4,6-dichloro-5-fluoro-pyrimidine (1 g, 5.99 mmol, 1 eq.), methyl piperidine-4-carboxylate (806.21 mg, 5.63 mmol, 0.94 eq.), DIEA (2.32 g, 17.97 mmol, 3.13 ml, 3 eq.) in dioxane (10 ml) was degassed and purged with $N_2$, and then the mixture was stirred at 80° C. for 2 hrs under $N_2$ atmosphere. The residue was diluted with $H_2O$ (30 ml) and extracted with ethyl acetate (30 ml×2). The combined organic layer was dried over $Na_2SO_4$, filtered, concentrated under reduced pressure and purified by flash silica gel chromatography (column: 20 g SepaFlash® Silica Flash Column, eluent: petroleum ether and ethyl acetate, gradient: 0% to 50% ethyl acetate, flow: 50 ml/min) to give the title compound (1.45 g, 5.30 mmol, 88% yield) as a yellow oil.

LC/MS: m/z=374.1[M+H]$^+$; tR: 0.894 min (LC/MS method C).

$^1$H NMR (400 MHz, CDCl$_3$): δ ppm 8.20-8.12 (m, 1H), 4.51-4.34 (m, 2H), 3.75-3.69 (m, 3H), 3.31-3.15 (m, 2H), 2.72-2.57 (m, 1H), 2.09-1.98 (m, 2H), 1.89-1.75 (m, 2H)

Intermediate-11 b

Ethyl 1-(6-chloro-5-fluoro-pyrimidin-4-yl)piperidine-4-carboxylate

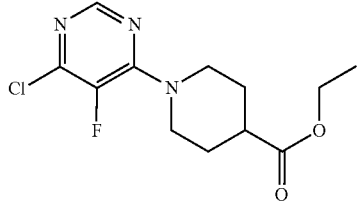 [SMILES: CCOC(=O)C1CCN(c2ncnc(Cl)c2F)CC1]

A mixture of 4,6-dichloro-5-fluoro-pyrimidine (1.06 g, 6.36 mmol, 1 eq.), ethyl piperidine-4-carboxylate (1.00 g, 6.36 mmol, 1.0 eq.), DIEA (3.29 g, 25.44 mmol, 4.43 ml, 4 eq.) in acetonitrile (20 ml) was stirred at room temperature for 1 hr. The residue was diluted with $H_2O$ (30 ml) and extracted with ethyl acetate (30 ml×2). The reaction mixture was diluted with ethyl acetate and washed two times with 0.1 N HCl. The combined organic layer was washed with water, dried over $Na_2SO_4$, filtered and concentrated under reduced pressure to give the title compound (1.65 g, 5.73 mmol, 90% yield).

LC/MS: m/z=288.1 [M+H]$^+$; tR: 2.14 min (LC/MS method A).

$^1$H NMR (400.23 MHz, DMSO-d$_6$): δ ppm 8.19 (d, J=1.34 Hz, 1H), 4.29 (m, 2H), 4.08 (q, J=7.09 Hz, 2H), 3.24 (m, 2H), 2.71 (m, 1H), 1.93 (m, 2H), 1.62 (m, 2H), 1.19 (t, J=7.09 Hz, 3H)

Syntheses of Examples

Example 1

3-Fluoro-5-[(3S)-2-[1-[6-(2-methylimidazol-1-yl)pyrimidin-4-yl]piperidine-4-carbonyl]isoxazolidin-3-yl]benzonitrile

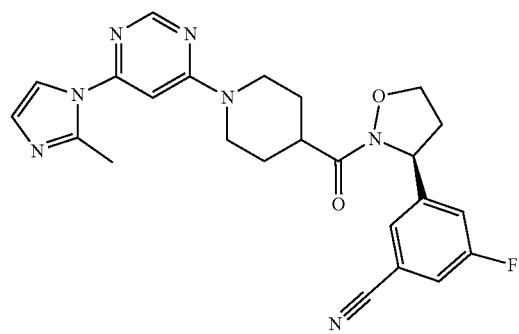 [SMILES: Cc1nccn1-c1cc(N2CCC(C(=O)N3OCC[C@H]3c3cc(F)cc(C#N)c3)CC2)ncn1]

A mixture of Intermediate-05 (300 mg, 926.56 umol, 1 eq., HCl), Intermediate-01 (222.45 mg, 972.89 umol, 1.05 eq., HCl), HATU (528.46 mg, 1.39 mmol, 1.5 eq.) and DIEA (838.24 mg, 6.49 mmol, 1.13 ml, 7 eq.) in DMF (3 ml) was stirred at 20° C. for 12 hrs. The reaction mixture was diluted with water (20 ml) and extracted with ethyl acetate (10 ml×3). The combined organic layer was washed with brine (15 ml×2), dried over $Na_2SO_4$, filtered, concentrated and purified by flash silica gel chromatography (eluent: DCM and MeOH, gradient: 0% to 10% MeOH), then by preparative HPLC (column: Phenomenex Gemini-NX C18 75×30 mm, 3 μm, eluent: water (0.225% formic acid) and acetonitrile, gradient: 12% to 42% acetonitrile in 5 min) to give the title compound (229 mg, 491.16 μmol, 53 yield) as a yellow solid.

LC/MS: m/z=462.1 [M+H]$^+$; tR: 0.501 min (LC/MS method C).

$^1$H NMR (400 MHz, DMSO-d$_6$): δ ppm 8.48 (s, 1H), 7.78 (br d, J=8.4 Hz, 1H), 7.66-7.60 (m, 2H), 7.49 (br d, J=9.7 Hz, 1H), 6.90 (s, 2H), 5.39 (br t, J=7.5 Hz, 1H), 4.48 (br d, J=3.9 Hz, 2H), 4.30 (dt, J=2.8, 7.6 Hz, 1H), 3.97-3.90 (m, 1H), 3.16-3.06 (m, 3H), 2.95-2.87 (m, 1H), 2.55 (s, 3H), 2.28-2.19 (m, 1H), 2.00-1.94 (m, 1H), 1.77 (br d, J=10.8 Hz, 1H), 1.58-1.48 (m, 2H)

SFC (Column: ChiralpakAD-3 50×4.6 mm I.D., 3 μm, eluent: 40% MeOH (0.05% DEA) in CO$_2$, flow rate: 3 ml/min, column temp: 35° C., 100 bar): tR: 1.05 min (100%)

Example 2

3-Fluoro-2-methyl-5-[(3S)-2-[1-[6-(2-methylimidazol-1-yl)pyrimidin-4-yl]piperidine-4-carbonyl]isoxazolidin-3-yl]benzonitrile

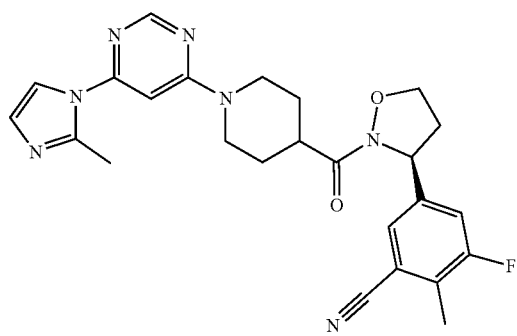 [SMILES: Cc1c(F)cc([C@@H]2CCON2C(=O)C2CCN(c3cc(-n4ccnc4C)ncn3)CC2)cc1C#N]

The title compound was synthesized using HATU coupling conditions described in example 1 using Intermediate-05 and Intermediate-03 as reagents to give 10 mg (0.021 mmol, 21% yield).

LC/MS: m/z=476.3 [M+H]$^+$; tR: 1.57 min (LC/MS method A).

$^1$H NMR (600.05 MHz, DMSO-d$_6$): δ ppm 8.48 (d, J=0.92 Hz, 1H), 7.64 (d, J=1.47 Hz, 1H), 7.55 (s, 1H), 7.43 (d, J=10.27 Hz, 1H), 6.90 (dd, J=5.78, 1.19 Hz, 2H), 5.35 (m, 1 H), 4.48 (br s, 1H), 4.29 (td, J=7.70, 7.70, 2.93 Hz, 1H), 3.93 (m, 1H), 3.28 (m, 1H), 3.11 (m, 3H), 2.89 (m, 1H), 2.54 (s, 3H), 2.37 (d, J=1.83 Hz, 3H), 2.23 (m, 1H), 1.96 (br d, J=11.19 Hz, 1H), 1.77 (br d, J=12.65 Hz, 1H), 1.53 (m, 2H)

Example 3

3-Fluoro-5-[(3S)-2-[1-[6-(2-methylpyrazol-3-yl)pyrimidin-4-yl]piperidine-4-carbonyl]isoxazolidin-3-yl]benzonitrile

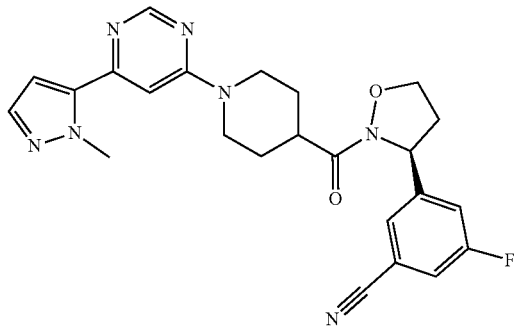 [SMILES: Cn1nccc1-c1cc(N2CCC(C(=O)N3OCC[C@H]3c3cc(F)cc(C#N)c3)CC2)ncn1]

The title compound was synthesized using HATU coupling conditions described in example 1 using Intermediate-06 and Intermediate-01 as reagents to give 240 mg (0.52 mmol, 77% yield).

LC/MS: m/z=463.2 [M+H]$^+$; tR: 0.66 min (LC/MS method B).

$^1$H NMR (400.23 MHz, DMSO-d$_6$): δ ppm 8.57 (d, J=0.98 Hz, 1H), 7.77 (d, J=8.62 Hz, 1H), 7.62 (s, 1H), 7.50 (s, 1H), 7.48 (d, J=1.96 Hz, 1H), 7.13 (s, 1H), 6.94 (d, J=1.96 Hz, 1H), 5.40 (m, 1H), 4.49 (br s, 2H), 4.30 (td, J=7.67, 7.67, 3.00 Hz, 1H), 4.14 (s, 3H), 3.94 (m, 1H), 3.09 (m, 3H), 2.91 (dddd, J=12.18, 9.15, 6.42, 3.06 Hz, 1H), 2.50 (u), 2.25 (m, 1H), 1.97 (br d, J=10.51 Hz, 1H), 1.77 (br d, J=12.84 Hz, 1H), 1.53 (m, 2H)

Example 4

[(3S)-3-(3,5-Difluorophenyl)isoxazolidin-2-yl]-[1-[6-(2-methylpyrazol-3-yl)pyrimidin-4-yl]-4-piperidyl]methanone

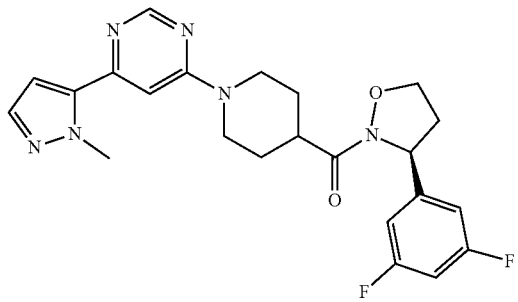 [SMILES: Cn1nccc1-c1cc(N2CCC(C(=O)N3OCC[C@H]3c3cc(F)cc(F)c3)CC2)ncn1]

The title compound was synthesized using HATU coupling conditions described in example 1 using Intermediate-06 and Intermediate-02a as reagents to give 180 mg (0.40 mmol, 57% yield).

LC/MS: m/z=455.1 [M+H]$^+$; tR: 0.55 min (LC/MS method C).

$^1$H NMR (400 MHz, CDCl$_3$): δ ppm 8.66 (s, 1H), 7.50 (d, J=2.0 Hz, 1H), 6.86-6.79 (m, 2H), 6.74-6.68 (m, 2H), 6.59 (d, J=2.0 Hz, 1H), 5.38 (dd, J=6.1, 8.7 Hz, 1H), 4.51-4.39 (m, 2H), 4.30 (dt, J=3.2, 7.7 Hz, 1H), 4.22 (s, 3H), 3.97-3.89 (m, 1H), 3.17-3.08 (m, 3H), 2.94-2.80 (m, 1H), 2.42-2.27 (m, 1H), 2.09 (br dd, J=2.4, 13.4 Hz, 1H), 1.87-1.79 (m, 3H)

SFC (Column: Chiralpak OJ-3 50×4.6 mm I.D., 3 μm, eluent: 5-40% MeOH (0.05% DEA) in CO$_2$, flow rate: 3 ml/min, column temp: 35° C., 100 bar): tR: 1.389 min (100%)

Example 5

[(3S)-3-(3-Chloro-5-fluoro-phenyl)isoxazolidin-2-yl]-[1-[6-(2-methylpyrazol-3-yl)pyrimidin-4-yl]-4-piperidyl]methanone

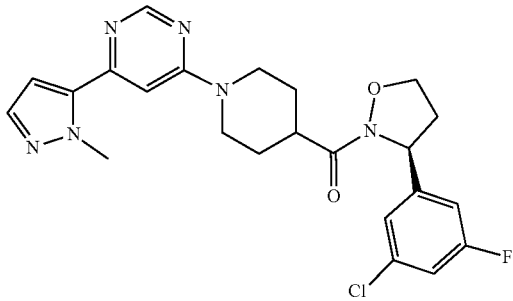 [SMILES: Cn1nccc1-c1cc(N2CCC(C(=O)N3OCC[C@H]3c3cc(F)cc(Cl)c3)CC2)ncn1]

The title compound was synthesized using HATU coupling conditions described in example 1 using Intermediate-06 and Intermediate-02b as reagents to give 37 mg (0.08 mmol, 78% yield).

LC/MS: m/z=471.2 [M+H]$^+$; tR: 2.00 min (LC/MS method A).

$^1$H NMR (400.23 MHz, DMSO-d$_6$): δ ppm 8.59 (s, 1H), 7.50 (d, J=1.96 Hz, 1H), 7.34 (dt, J=8.68 Hz, J=2.08 Hz, 1H), 7.20 (s, 1H), 7.15 (s, 1H), 7.11 (br d, J=9.41 Hz, 1H), 6.93 (d, J=1.96 Hz, 1H), 5.35 (m, 1H), 4.49 (br s, 2H), 4.29 (m, 1H), 4.13 (s, 3H), 3.92 (m, 1H), 3.11 (m, 3H), 2.90 (m, 1H), 2.22 (m, 1H), 1.97 (br d, J=11.13 Hz, 1H), 1.77 (br d, J=12.23 Hz, 1H), 1.53 (m, 2H)

Example 6

3-Fluoro-5-[(3S)-2-[1-[6-(3-methyl-1H-pyrazol-4-yl)pyrimidin-4-yl]piperidine-4-carbonyl]isoxazolidin-3-yl]benzonitrile

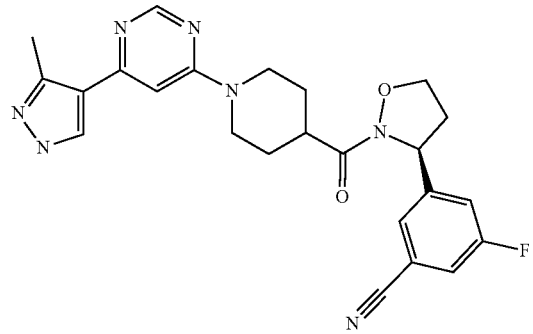

A mixture of Intermediate-08 (41.58 mg, 0.10 mmol, 1.0 eq.), 3-methyl-4-(4,4,5,5-tetramethyl-1,3,2-dioxaborolan-2- yl)-1H-pyrazole (38.22 mg, 0.18 mmol, 1.8 eq.), sodium carbonate (40.28 mg, 0.38 mmol, 3.8 eq.) und 1,1'-bis (diphenylphosphino)-ferrocene-palladium(II)dichloride dichloromethane complex (16.33 mg, 0.02 mmol, 0.2 eq.) in DME (3.0 ml) and water (1 ml) was heated to 100° C. under microwave irradiation for 30 min. The reaction mixture was filtered and purified by preparative HPLC (column: Luna(r) 5 μm C18(2) 100 Å 100×30 mm, AXIAL, eluent: water and acetonitrile, gradient: 10% to 100% acetonitrile in 12 min, flow: 50 ml/min) to give the title compound (18 mg, 39% yield).

LC/MS: m/z=462.2 [M+H]$^+$; tR: 1.34 min (LC/MS method A).

$^1$H NMR (400.23 MHz, DMSO-d$_6$): δ ppm 8.45 (s, 1H), 8.14 (s, 1H), 7.77 (br d, J=7.98 Hz, 1H), 7.62 (s, 1H), 7.49 (br d, J=9.41 Hz, 1H), 6.93 (s, 1H), 5.40 (m, 1H), 4.45 (br d, J=9.90 Hz, 2H), 4.30 (td, J=7.58, 2.81 Hz, 1H), 3.94 (m, 1H), 3.09 (br d, J=7.09 Hz, 1H), 3.03 (m, 2H), 2.91 (m, 1H), 2.27 (m, 2H), 1.95 (br d, J=11.37 Hz, 1H), 1.76 (br d, J=11.74 Hz, 1H), 1.52 (m, 2H), 1.24 (s, 3H)

Example 7

3-[(3S)-2-[1-[6-(4-Cyclopropyl-2-methyl-imidazol-1-yl)pyrimidin-4-yl]piperidine-4-carbonyl]isoxazolidin-3-yl]-5-fluoro-benzonitrile

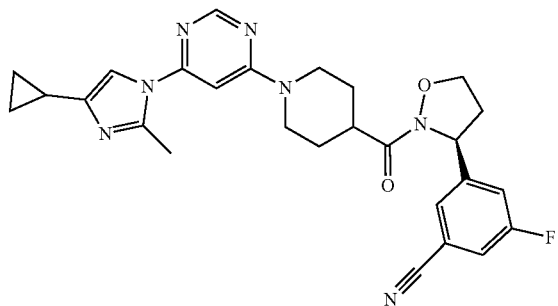 [SMILES: Cc1nc(C2CC2)cn1-c1cc(N2CCC(C(=O)N3OCC[C@H]3c3cc(F)cc(C#N)c3)CC2)ncn1]

The title compound was synthesized using HATU coupling conditions described in example 1 using Intermediate-07 and Intermediate-02a as reagents to give 77 mg (0.23 mmol, 36% yield).

LC/MS: m/z=502.2 [M+H]$^+$; tR: 0.81 min (LC/MS method C).

$^1$H NMR (400 MHz, DMSO-d$_6$): δ ppm 8.45 (s, 1H), 8.13 (s, 1H), 7.80-7.74 (m, 1H), 7.62 (s, 1H), 7.49 (br d, J=9.5 Hz, 1H), 7.43 (s, 1H), 6.84 (s, 1H), 5.42-5.36 (m, 1H), 4.54-4.39 (m, 2H), 4.30 (dt, J=2.8, 7.7 Hz, 1H), 3.96-3.90 (m, 1H), 3.14-3.05 (m, 3H), 2.95-2.88 (m, 1H), 2.52 (s, 3H), 2.27-2.21 (m, 1H), 1.99-1.94 (m, 1H), 1.80-1.73 (m, 2H), 1.56-1.48 (m, 2H), 0.80-0.76 (m, 2H), 0.68-0.64 (m, 2H)

SFC (Column: Chiralpak OJ-3 50×4.6 mm I.D., 3 μm, eluent: 5-40% MeOH (0.05% DEA) in CO$_2$, flow rate: 3 ml/min, column temp: 35° C., 100 bar): tR: 1.73 min (98.8%)

Example 8

5-[(3S)-2-[1-[6-(4-Cyclopropyl-2-methyl-imidazol-1-yl)pyrimidin-4-yl]piperidine-4-carbonyl]isoxazolidin-3-yl]-3-fluoro-2-methyl-benzonitrile

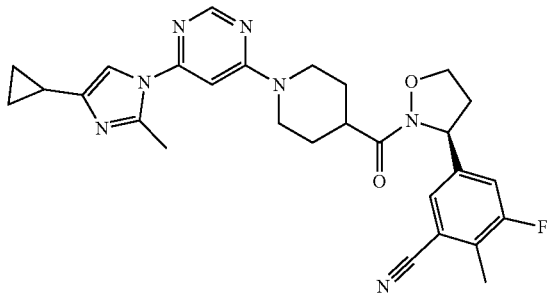 [SMILES: Cc1c(F)cc([C@@H]2CCON2C(=O)C2CCN(c3cc(-n4cc(C5CC5)nc4C)ncn3)CC2)cc1C#N]

The title compound was synthesized using HATU coupling conditions described in example 1 using Intermediate-07 and Intermediate-03 as reagents to give 28 mg (0.08 mmol, 81% yield).

LC/MS: m/z=516.3 [M+H]$^+$; tR: 1.67 min (LC/MS method A).

$^1$H NMR (400.23 MHz, DMSO-d$_6$): δ ppm 8.45 (s, 1H), 7.55 (s, 1H), 7.44 (m, 2H), 6.83 (s, 1H), 5.35 (m, 1H), 4.47 (br s, 2H), 4.29 (td, J=7.64, 7.64, 3.18 Hz, 1H), 3.93 (m, 1H), 3.10 (m, 3H), 2.89 (m, 1H), 2.50 (s, 3H, in DMSO peak), 2.37 (d, J=1.71 Hz, 3H), 2.24 (m, 1H), 1.96 (br d, J=12.84 Hz, 1H), 1.77 (m, 2H), 1.52 (m, 2H), 0.78 (m, 2H), 0.67 (m, 2H)

Example 9

3-[(3S)-2-[1-[6-(2,5-Dimethylpyrazol-3-yl)pyrimidin-4-yl]piperidine-4-carbonyl]isoxazolidin-3-yl]-5-fluoro-benzonitrile

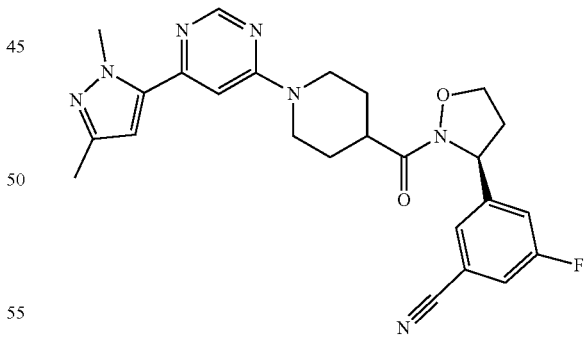

A mixture of Intermediate-08 (100 mg, 240.47 μmol, 1 eq.), 1,3-dimethyl-5-(4,4,5,5-tetramethyl-1,3,2-dioxaborolan-2-yl)pyrazole (58.75 mg, 264.52 μmol, 1.1 eq.), K$_2$CO$_3$ (66.47 mg, 480.95 μmol, 2 eq.) and Pd(dppf)Cl$_2$·CH$_2$Cl$_2$ (19.64 mg, 24.05 μmol, 0.1 eq.) in dioxane (0.8 ml) and H$_2$O (0.2 ml) was degassed and purged with N$_2$ for 3 times. The reaction mixture was stirred at 80° C. for 2 hrs under N$_2$ atmosphere. The reaction mixture was diluted with water (5 ml) and extracted with ethyl acetate (3 ml×3). The combined organic layer was washed with brine (8 ml), dried over

Example 10

3-Fluoro-5-[(3S)-2-[1-[6-(3-methyl-1,2,4-triazol-1-yl)pyrimidin-4-yl]piperidine-4-carbonyl]isoxazolidin-3-yl]benzonitrile

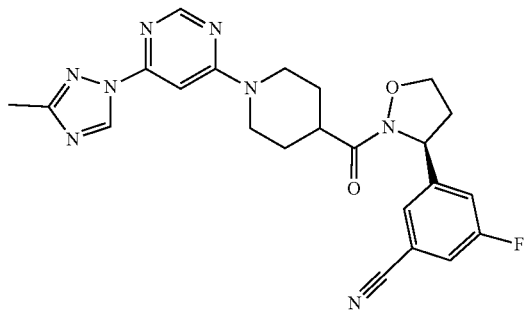 [SMILES: Cc1ncn(-c2cc(N3CCC(C(=O)N4OCC[C@H]4c4cc(F)cc(C#N)c4)CC3)ncn2)n1]

The title compound was synthesized using HATU coupling conditions described in example 1 using Intermediate-07 and Intermediate-03 as reagents to give 62 mg (0.13 mmol, 38% yield).

LC/MS: m/z=463.3 [M+H]⁺; tR: 0.820 min (LC/MS method C).

¹H NMR (400 MHz, CDCl₃): δ ppm 9.20 (s, 1H), 8.43 (s, 1H), 7.32 (s, 1H), 7.21 (br d, J=1.1 Hz, 1H), 7.18 (br d, J=1.6 Hz, 1H), 6.96 (s, 1H), 5.34 (dd, J=8.7, 6.3 Hz, 1H), 5.20-5.09 (m, 1H), 4.47-4.34 (m, 1H), 4.27 (td, J=7.8, 2.9 Hz, 1H), 3.93-3.85 (m, 1H), 3.26-3.14 (m, 2H), 3.13-3.04 (m, 1H), 2.86 (dddd, J=12.3, 9.2, 6.4, 2.9 Hz, 1H), 2.48 (s, 3H), 2.33-2.21 (m, 1H), 2.05 (br dd, J=13.5, 3.3 Hz, 1H), 1.88-1.72 (m, 3H) SFC (Column: Chiralcel OJ-3 50×4.6 mm I.D., 3 μm, gradient: 5% to 40% MeOH (0.05% DEA) in CO₂, flow rate: 3 ml/min, column temp: 35° C., 100 bar): tR: 1.418 min (100%)

Example 11

3-Fluoro-5-[(3S)-2-[1-[6-(5-methyl-1,2,4-triazol-1-yl)pyrimidin-4-yl]piperidine-4-carbonyl]isoxazolidin-3-yl]benzonitrile

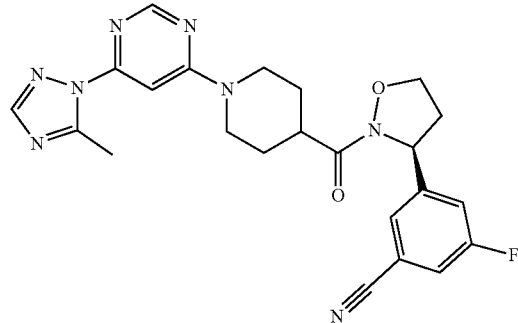 [SMILES: Cc1ncnn1-c1cc(N2CCC(C(=O)N3OCC[C@H]3c3cc(F)cc(C#N)c3)CC2)ncn1]

The title compound was synthesized using HATU coupling conditions described in example 1 using Intermediate-09 and Intermediate-01 as reagents to give 38 mg (0.12 mmol, 24% yield).

LC/MS: m/z 463.1 [M+H]⁺; tR: 0.874 min (LC/MS method C).

¹H NMR (400 MHz, CDCl₃): δ ppm 8.52 (s, 1H), 7.92 (s, 1H), 7.40 (s, 1H), 7.28 (br d, J=2.1 Hz, 1H), 7.26 (br d, J=1.5 Hz, 1H), 7.09 (s, 1H), 5.41 (dd, J=6.4, 8.8 Hz, 1H), 4.50 (br d, J=2.1 Hz, 2H), 4.34 (dt, J=2.9, 7.9 Hz, 1H), 3.94 (dt, J=6.7, 8.8 Hz, 1H), 3.24-3.10 (m, 3H), 2.94 (s, 3H), 2.93-2.87 (m, 1H), 2.39-2.29 (m, 1H), 2.09 (br dd, J=2.7, 13.1 Hz, 1H), 1.87-1.80 (m, 3H)

SFC (Column: Chiralcel OD-3 50×4.6 mm I.D., 3 μm, gradient: 5% to 40% MeOH (0.05% DEA) in CO₂, flow rate: 3 ml/min, column temp: 35° C., 100 bar): tR: 1.926 min (100%)

Example 12

3-Fluoro-5-[(3S)-2-[1-[6-(3-methyltriazol-4-yl)pyrimidin-4-yl]piperidine-4-carbonyl]isoxazolidin-3-yl]benzonitrile

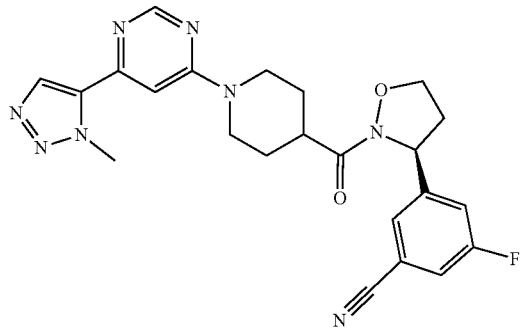 [SMILES: Cn1nncc1-c1cc(N2CCC(C(=O)N3OCC[C@H]3c3cc(F)cc(C#N)c3)CC2)ncn1]

Step 1

Tributyl-(3-methyltriazol-4-yl)stannane

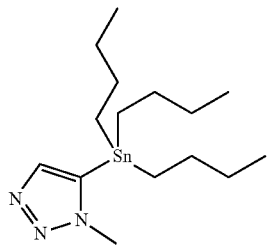 [SMILES: CCC[CH2][Sn]([CH2]CCC)([CH2]CCC)[c]1cnnn1C]

To a solution of n-BuLi (2.5 M, 2.41 ml, 1 eq.) in THF (5 ml) 5-methylcyclohexa-1,3-diene (566.57 mg, 6.02 mmol, 5 ml, 1 eq.) was added dropwise at −70° C., followed by a solution of 1-methyltriazole (500 mg, 6.02 mmol, 1 eq.) in THF (2 ml) under $N_2$ atmosphere. The reaction mixture was stirred for 1 hr and tributyl(chloro)stannane (1.96 g, 6.02 mmol, 1.62 ml, 1 eq.) was added. The reaction mixture was warmed smoothly to 25° C. After 10 hrs the reaction mixture was filtered, concentrated under reduced pressure and purified by flash silica gel chromatography (column: 20 g SepaFlash® Silica Flash Column, eluent: petroleum ether and ethyl acetate, gradient: 0% to 20% ethyl acetate, flow: 50 ml/min) to give the title compound (1.3 g, 3.49 mmol, 58% yield) as a colorless oil.

LC/MS: m/z 374.1 [M+H]$^+$; tR: 0.831 min (LC/MS method C).

$^1$H NMR (400 MHz, CDCl$_3$): δ ppm 7.61 (s, 1H), 4.10 (s, 3H), 1.57-1.49 (m, 6H), 1.37-1.31 (m, 6H), 1.21-1.16 (m, 6H), 0.90 (t, J=7.3 Hz, 9H)

Step 2

3-Fluoro-5-[(3S)-2-[1-[6-(3-methyltriazol-4-yl)pyrimidin-4-yl]piperidine-4-carbonyl]isoxazolidin-3-yl]benzonitrile

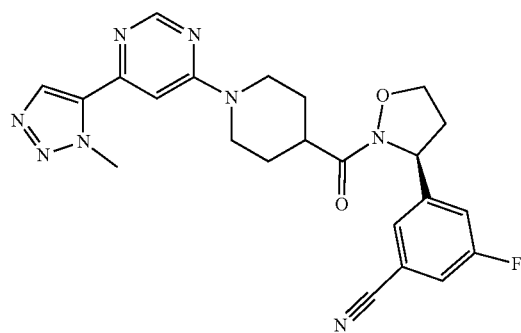 [SMILES: Cn1nncc1-c1cc(N2CCC(C(=O)N3OCC[C@H]3c3cc(F)cc(C#N)c3)CC2)ncn1]

A mixture of Intermediate-08 (100 mg, 240.47 μmol, 1 eq.), tributyl-(3-methyltriazol-4-yl)stannane (178.98 mg, 480.95 μmol, 2 eq.), triethylamine (48.67 mg, 480.95 μmol, 66.94 μl, 2 eq.), CuI (4.58 mg, 24.05 μmol, 0.1 eq.) and Pd(PPh$_3$)$_4$ (27.79 mg, 24.05 μmol, 0.1 eq.) in dioxane (1 ml) was degassed and purged with $N_2$ for 3 times. The reaction mixture was stirred at 100° C. for 12 hrs under $N_2$ atmosphere, quenched by addition of saturated aqueous KF solution (3 ml), diluted with water (5 ml) and extracted with ethyl acetate (5 ml×3). The combined organic layer was dried over Na$_2$SO$_4$, filtered, concentrated under reduced pressure and purified by preparative HPLC (column: Phenomenex C18 75×30 mm, 3 μm, eluent: water (0.1% formic acid) and acetonitrile, gradient: 28% to 58% acetonitrile in 7 min) to give the title compound (26 mg, 56.22 μmol, 23% yield) as a yellow solid.

LC/MS: m/z 463.1 [M+H]$^+$; tR: 0.626 min (LC/MS method C).

$^1$H NMR (400 MHz, DMSO-d$_6$): δ ppm 8.60 (d, J=1.0 Hz, 1H), 8.39 (s, 1H), 7.80-7.75 (m, 1H), 7.62 (s, 1H), 7.49 (br d, J=9.2 Hz, 1H), 7.28 (d, J=0.9 Hz, 1H), 5.39 (br dd, J=6.5, 8.1 Hz, 1H), 4.58-4.42 (m, 2H), 4.32 (s, 3H), 4.31-4.27 (m, 1H), 3.98-3.89 (m, 1H), 3.16-3.08 (m, 3H), 2.91 (tdd, J=3.1, 5.8, 8.8 Hz, 1H), 2.24 (dtd, J=2.0, 4.6, 9.3 Hz, 1H), 2.01-1.94 (m, 1H), 1.82-1.74 (m, 1H), 1.56-1.47 (m, 2H)

SFC (Column: Chiralcel OD-3 50×4.6 mm I.D., 3 μm, gradient: 5% to 40% MeOH (0.05% DEA) in CO$_2$, flow rate: 3 ml/min, column temp: 35° C., 100 bar): tR: 2.380 min (100%)

Example 13

3-Fluoro-5-[(3S)-2-[1-[5-fluoro-6-(2-methylimidazol-1-yl)pyrimidin-4-yl]piperidine-4-carbonyl]isoxazolidin-3-yl]benzonitrile

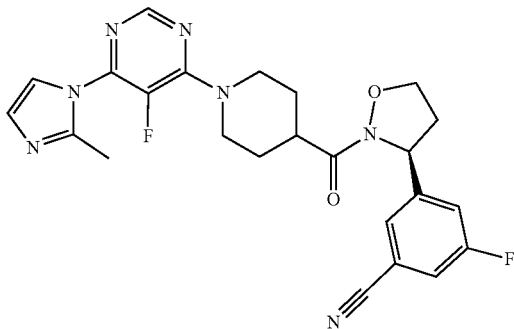 [SMILES: Cc1nccn1-c1ncnc(N2CCC(C(=O)N3OCC[C@H]3c3cc(F)cc(C#N)c3)CC2)c1F]

Step 1

Methyl 1-[5-fluoro-6-(2-methylimidazol-1-yl)pyrimidin-4-yl]piperidine-4-carboxylate

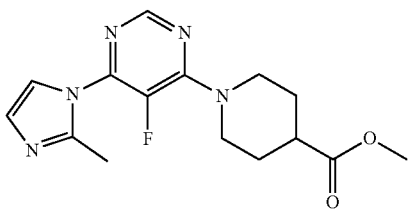 [SMILES: COC(=O)C1CCN(c2ncnc(-n3ccnc3C)c2F)CC1]

A mixture of Intermediate-11a (5.38 g, 19.66 mmol, 1 eq.), 2-methyl-1H-imidazole (2.10 g, 25.55 mmol, 1.3 eq.), K$_2$CO$_3$ (10.87 g, 78.63 mmol, 4 eq.), CuI (1.87 g, 9.83 mmol, 0.5 eq.) in DMSO (50 ml) was degassed and purged with $N_2$ for 3 times. The reaction mixture was stirred at 120° C. for 16 hrs, diluted with H$_2$O (60 ml) and extracted with ethyl acetate (60 ml×2). The combined organic layer was dried over anhydrous Na$_2$SO$_4$, filtered, concentrated under reduced pressure and purified by flash silica gel chromatography (column: 8 g SepaFlash® Silica Flash Column, eluent: petroleum ether and ethyl acetate, gradient: 0% to 80% ethyl acetate, flow: 40 ml/min) to give the title compound (6 g, 17.85 mmol, 91% yield) as a white solid.

¹H NMR (400 MHz, CDCl₃): δ ppm 8.30 (d, J=1.3 Hz, 1H), 7.18-7.10 (m, 1H), 7.02 (s, 1H), 4.52-4.40 (m, 2H), 3.75-3.65 (m, 3H), 3.32-3.17 (m, 2H), 2.71-2.64 (m, 2H), 2.49 (s, 3H), 2.05 (br d, J=3.5 Hz, 1H), 1.89-1.77 (m, 2H)

Step 2

1-[5-Fluoro-6-(2-methylimidazol-1-yl)pyrimidin-4-yl]piperidine-4-carboxylic acid

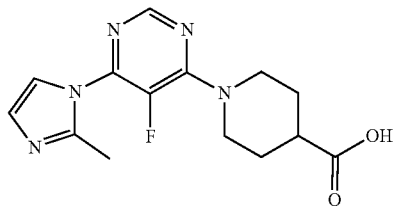 [SMILES: Cc1nccn1-c1ncnc(N2CCC(C(=O)O)CC2)c1F]

To a solution of methyl 1-[5-fluoro-6-(2-methylimidazol-1-yl)pyrimidin-4-yl]piperidine-4-carboxylate (3 g, 9.39 mmol, 1 eq.) in THF (24 ml) LiOH·H₂O (1.58 g, 37.58 mmol, 4 eq.) and H₂O (6 ml) were added. The reaction mixture was stirred at 25° C. for 2 hrs, diluted with H₂O (60 ml) and extracted with ethyl acetate (60 ml×2). The combined organic layer was dried over anhydrous Na₂SO₄, filtered, concentrated under reduced pressure and purified by reversed-phase HPLC (column: 330 g Flash Column Welch Ultimate XB_C18 20-40 µm, 120 Å, eluent: water (0.1% formic acid) and acetonitrile, gradient: 0% to 25% acetonitrile in 15 min, 25% acetonitrile for 10 min, flow: 100 mL/min) to give the title compound (1.4 g, 4.58 mmol, 49% yield) as a white solid.

LC/MS: m/z 306.2 [M+H]⁺; tR: 0.226 min (LC/MS method C).

¹H NMR (400 MHz, DMSO-d₆): δ ppm 12.49-12.14 (m, 1H), 8.36 (d, J=1.4 Hz, 1H), 7.47 (dd, J=1.6, 2.4 Hz, 1H), 7.04 (d, J=1.5 Hz, 1H), 4.34 (br d, J=13.4 Hz, 2H), 3.27-3.21 (m, 2H), 2.64-2.61 (m, 1H), 2.40 (s, 3H), 1.97-1.91 (m, 2H), 1.69-1.61 (m, 2H)

Step 3

3-Fluoro-5-[(3S)-2-[1-[5-fluoro-6-(2-methylimidazol-1-yl)pyrimidin-4-yl]piperidine-4-carbonyl]isoxazolidin-3-yl]benzonitrile

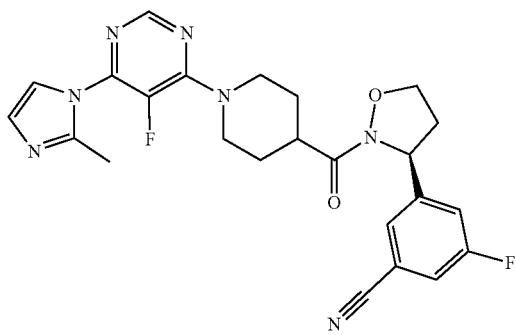 [SMILES: Cc1nccn1-c1ncnc(N2CCC(C(=O)N3OCC[C@H]3c3cc(F)cc(C#N)c3)CC2)c1F]

The title compound was synthesized using HATU coupling conditions described in example 1 using 1-[5-fluoro-6-(2-methylimidazol-1-yl)pyrimidin-4-yl]piperidine-4-carboxylic acid (step 2) and Intermediate-01 as reagents to give 112 mg (228.7 µmol, 78% yield) as a yellow solid.

LC/MS: m/z 480.1 [M+H]⁺; tR: 0.512 min (LC/MS method C).

¹H NMR (400 MHz, CDCl₃): δ ppm 8.33 (d, J=1.5 Hz, 1H), 7.40 (s, 1H), 7.34 (s, 1H), 7.28 (br s, 2H), 7.26 (br s, 1H), 5.42 (dd, J=6.4, 8.7 Hz, 1H), 4.62 (br d, J=13.3 Hz, 2H), 4.34 (dt, J=2.9, 7.8 Hz, 1H), 4.02-3.91 (m, 1H), 3.34-3.28 (m, 2H), 3.22-3.13 (m, 1H), 2.95 (dddd, J=3.0, 6.4, 9.2, 12.3 Hz, 1H), 2.68 (s, 3H), 2.40-2.28 (m, 1H), 2.13 (br dd, J=3.2, 13.6 Hz, 1H), 1.93-1.85 (m, 3H)

SFC (Column: Chiralcel OJ-3 50×4.6 mm I.D., 3 µm, gradient: 5% to 40% MeOH (0.05% DEA) in CO₂, flow rate: 3 ml/min, column temp: 35° C., 100 bar): tR: 1.294 min (100%)

Example 14

3-Fluoro-5-[(3S)-2-[1-[5-fluoro-6-(4-methylpyrazol-1-yl)pyrimidin-4-yl]piperidine-4-carbonyl]isoxazolidin-3-yl]-2-methyl-benzonitrile

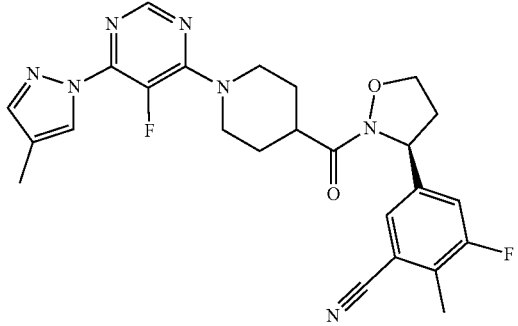 [SMILES: Cc1cnn(-c2ncnc(N3CCC(C(=O)N4OCC[C@H]4c4cc(F)c(C)c(C#N)c4)CC3)c2F)c1]

Step 1

Ethyl 1-[5-fluoro-6-(4-methylpyrazol-1-yl)pyrimidin-4-yl]piperidine-4-carboxylate

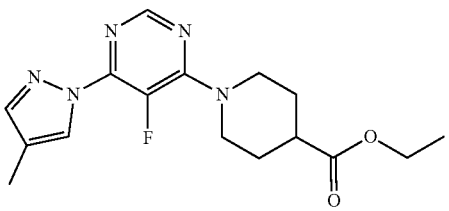 [SMILES: CCOC(=O)C1CCN(c2ncnc(-n3cc(C)cn3)c2F)CC1]

A mixture of Intermediate-11 b (300 mg, 1.04 mmol, 1 eq.), 4-methyl-1H-pyrazole (171.22 mg, 0.168 ml, 2.085 mmol, 2.0 eq.), potassium carbonate (576.42 mg, 4.171 mmol, 4.0 eq.) und copper(I) iodide (99.3 mg, 0.521 mmol, 0.5 eq.) in DMSO (1.5 ml) was stirred at 120° C. under microwave irradiation for 4 hrs. The reaction mixture was diluted with water and ethyl acetate and filtered. The filtrate was evaporated under reduced pressure to give the title compound (294 mg, 0.75 mmol, 72% yield), which was used directly in the next step.

Step 2

1-[5-Fluoro-6-(4-methylpyrazol-1-yl)pyrimidin-4-yl]piperidine-4-carboxylic acid

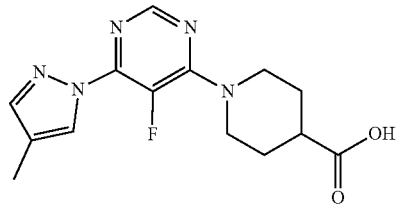 [SMILES: Cc1cnn(-c2ncnc(N3CCC(C(=O)O)CC3)c2F)c1]

A solution of the crude product from step 1 (294 mg, 0.75 mmol, 1 eq.) in NaOH (2 N in water/THF/MeOH=1/1/1, 5.7 ml, 3.75 mmol, 5 eq.) was stirred at room temperature for 16 hrs. The reaction mixture was acidified with 1 N H₂SO₄ and extracted three times with ethyl acetate. The combined organic layer was dried with Na₂SO₄, filtered, evaporated and purified by preparative HPLC (column: YMC-Actus Triart Prep C18-S 250×30 mm, 5-10 μm, eluent: water (0.05% TFA) and acetonitrile, gradient: 5% to 100% acetonitrile in 24 min, flow: 70 ml/min) to give the title compound (156 mg, 68% yield).

LC/MS: m/z=306.1 [M+H]$^+$; tR: 1.61 min (LC/MS method A).

$^1$H NMR (400.23 MHz, DMSO-d$_6$): δ ppm 12.28 (br s, 1H), 8.26 (d, J=1.47 Hz, 1H), 8.23 (s, 1H), 7.71 (s, 1H), 4.29 (br d, J=13.45 Hz, 2H), 3.25 (m, 2H), 2.61 (m, 1H), 2.10 (s, 3H), 1.93 (br dd, J=13.20, 3.30 Hz, 2H), 1.63 (m, 2H)

Step 3

3-Fluoro-5-[(3S)-2-[1-[5-fluoro-6-(4-methylpyrazol-1-yl)pyrimidin-4-yl]piperidine-4-carbonyl]isoxazolidin-3-yl]-2-methyl-benzonitrile

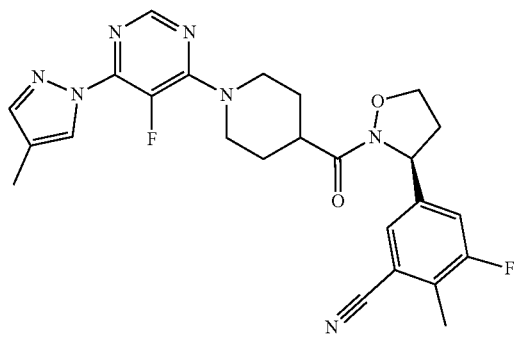

The title compound was synthesized using HATU coupling conditions described in example 1 using the compound from step 2 and Intermediate-03 as reagents to give 36 mg (0.072 mmol, 72% yield).

LC/MS: m/z=494.2 [M+H]$^+$; tR: 2.40 min (LC/MS method A).

$^1$H NMR (400.23 MHz, DMSO-d$_6$): δ ppm 8.26 (d, J=1.47 Hz, 1H), 8.23 (s, 1H), 7.70 (s, 1H), 7.56 (s, 1H), 7.43 (d, J=10.27 Hz, 1H), 5.35 (m, 1H), 4.40 (m, 2H), 4.29 (m, 1H), 3.93 (m, 1H), 3.24 (m, 2H), 3.13 (br s, 1H), 2.88 (m, 1H), 2.37 (d, J=1.83 Hz, 3H), 2.23 (m, 1H), 2.10 (s, 3H), 1.98 (br d, J=11.74 Hz, 1H), 1.80 (m, 1H), 1.64 (m, 2H)

Example 15

[(3S)-3-(3,5-Difluorophenyl)isoxazolidin-2-yl]-[1-[5-fluoro-6-(2-methylpyrazol-3-yl)pyrimidin-4-yl]-4-piperidyl]methanone

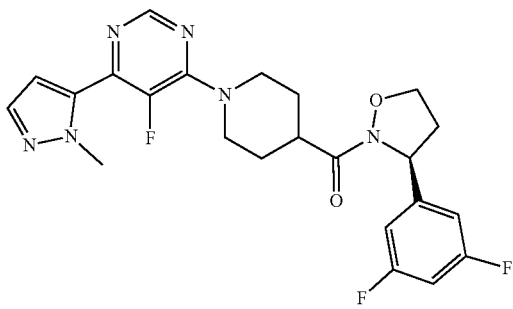

Step 1

Methyl 1-[5-fluoro-6-(2-methylpyrazol-3-yl)pyrimidin-4-yl]piperidine-4-carboxylate

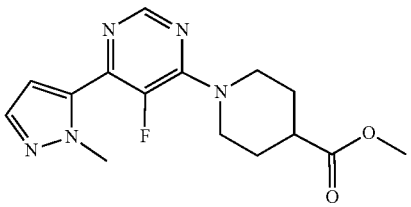 [SMILES: COC(=O)C1CCN(c2ncnc(-c3ccnn3C)c2F)CC1]

To a solution of Intermediate-11a (1.4 g, 5.12 mmol, 1 eq.) in dioxane (16 ml) and H₂O (4 ml) K₂CO₃ (1.41 g, 10.23 mmol, 2 eq.), Pd(dppf)Cl₂ (374.29 mg, 511.53 μmol, 0.1 eq.) and 1-methyl-5-(4,4,5,5-tetramethyl-1,3,2-dioxaborolan-2-yl)pyrazole (1.17 g, 5.63 mmol, 1.1 eq.) were added. The mixture was stirred at 80° C. for 12 hrs, diluted with H₂O (30 ml) and extracted with ethyl acetate (30 ml×2). The combined organic layer was dried over Na₂SO₄, filtered, concentrated under reduced pressure and purified by flash silica gel chromatography (column: 4 g SepaFlash® Silica Flash Column, eluent: petroleum ether and ethyl acetate, gradient: 0% to 30% ethyl acetate, flow: 50 ml/min) to give the title compound (1.66 g, 4.05 mmol, 79% yield) as a white solid.

LC/MS: m/z 320.12 [M+H]$^+$; tR: 0.875 min (LC/MS method C).

$^1$H NMR (400 MHz, CDCl₃): δ ppm 8.44 (d, J=2.3 Hz, 1H), 7.56 (d, J=2.0 Hz, 1H), 6.73 (dd, J=2.1, 3.9 Hz, 1H), 4.46 (td, J=3.4, 13.7 Hz, 2H), 4.19 (s, 3H), 3.83 (s, 1H), 3.72 (s, 3H), 3.32-3.18 (m, 2H), 2.67 (s, 1H), 2.03-2.01 (m, 1H), 1.86-1.79 (m, 2H)

Step 2

1-[5-Fluoro-6-(2-methylpyrazol-3-yl)pyrimidin-4-yl]piperidine-4-carboxylic acid

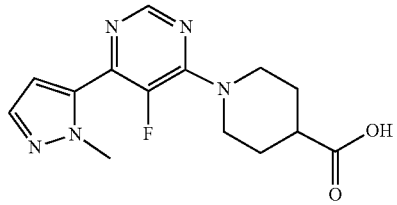 [SMILES: Cn1nccc1-c1ncnc(N2CCC(C(=O)O)CC2)c1F]

To a solution of methyl 1-[5-fluoro-6-(2-methylpyrazol-3-yl)pyrimidin-4-yl]piperidine-4-carboxylate (1.16 g, 2.83 mmol, 1 eq.) in THF (8 ml) and H$_2$O (2 ml) LiOH·H$_2$O (237.80 mg, 5.67 mmol, 2 eq.) was added. The reaction mixture was stirred at 25° C. for 2 hrs, adjusted to pH 3 with 1 N HCl solution and THF was removed under reduced pressure. The mixture was filtered and the filter cake was washed with 1 N HCl solution to give the title (380 mg, 1.24 mmol, 44% yield) as a white solid.

LC/MS: m/z 306.1 [M+H]$^+$; tR: 0.899 min (LC/MS method C).

$^1$H NMR (400 MHz, DMSO-d$_6$): δ ppm 8.44 (d, J=2.5 Hz, 1H), 7.56 (d, J=2.0 Hz, 1H), 6.72 (dd, J=2.0, 3.8 Hz, 1H), 4.44-4.21 (m, 2H), 4.05 (s, 3H), 3.21-3.16 (m, 2H), 2.64-2.54 (m, 2H), 1.93 (br dd, J=3.3, 13.3 Hz, 2H), 1.68-1.57 (m, 2H)

Step 3

[(3S)-3-(3,5-Difluorophenyl)isoxazolidin-2-yl]-[1-[5-fluoro-6-(2-methylpyrazol-3-yl)pyrimidin-4-yl]-4-piperidyl]methanone

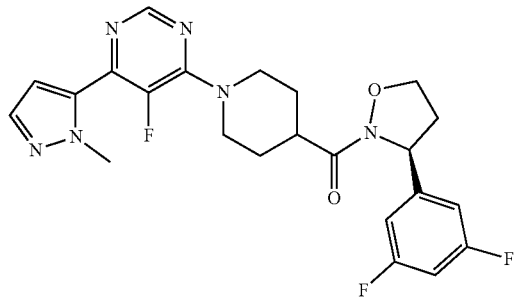 [SMILES: Cn1nccc1-c1ncnc(N2CCC(C(=O)N3OCC[C@H]3c3cc(F)cc(F)c3)CC2)c1F]

The title compound was synthesized using HATU coupling conditions described in example 1 using Intermediate-11a and Intermediate-01 as reagents to give 120 mg (0.25 mmol, 78% yield).

LC/MS: m/z=473.1 [M+H]$^+$; tR: 0.942 min (LC/MS method C).

$^1$H NMR (400 MHz, CDCl$_3$): δ ppm 8.43 (s, 1H), 7.57 (d, J=1.7 Hz, 1H), 6.87-6.79 (m, 2H), 6.77-6.67 (m, 2H), 5.38 (dd, J=6.3, 8.7 Hz, 1H), 4.70-4.47 (m, 2H), 4.30 (dt, J=3.2, 7.7 Hz, 1H), 4.17 (s, 3H), 4.01-3.87 (m, 1H), 3.35-3.21 (m, 2H), 3.19-3.07 (m, 1H), 2.93-2.81 (m, 1H), 2.40-2.29 (m, 1H), 2.17-2.06 (m, 1H), 2.00-1.88 (m, 3H)

SFC: (Column: Chiralcel OD 50×4.6 mm I.D., 3 μm, gradient: 5% to 40% MeOH (0.05% DEA) in CO$_2$, flow rate: 3 ml/min, column temp: 35° C., 100 bar): tR: 1.581 min (100%)

Evaluation of Receptor-Interacting Protein Kinase 1 Inhibition.

The catalytic activity of RIPK1 was measured by monitoring the conversion of Adenosine triphosphate (ATP) to Adenosine diphosphate (ADP) due to autophosphorylation using an ADP-Glo kinase kit (Promega, catalog no. V9104).

In detail, 2 μl recombinantly produced hRIPK1 (aa 1-375) fusion protein (end concentration 3.6 μg/ml) and 2 μl compound (end concentration 33300-1.69 nM; DMSO end concentration 1%) were incubated for 30 minutes at room temperature and then 2 μl ATP (ADP Glo kit, end concentration 50 μM) were added. After another 240 minutes incubation at room temperature, 5 μl Promega ADP-Glo reagent I were added to quench the reaction and deplete unconsumed ATP. After an incubation period of 30 minutes, 10 μl Promega ADP-Glo detection reagent II were added resulting in conversion of ADP to ATP, which generates a light-reaction between luciferase and luciferin. Luminescence was quantified after 30 minutes with a Pherastar FS (BMG LABTECH, Ortenberg).

For the dose response experiments an IC$_{50}$ value with 95% confidence interval was calculated using the 4-parameter logistic model according to Ratkowsky and Reedy with constraints for lower and upper asymptotes at 0% and 100%. The adjustment was obtained by nonlinear regression using the Levenberg Marquardt algorithm.

Cellular Assay in U937 Cells to Measure the Activity of RIPK1-Inhibitors on Cell Death (Necroptosis).

Upon TNF-Receptor I ligation, Ser/Thr kinase RIPK1 is recruited to a transient receptor complex I. Upon modification of RIPK1 which promotes activation of RIPK1, complex IIIb can form, that involves recruitment of RIPK3 and MLKL (mixed lineage-kinase domain-like protein) which then translocates from the cytosol to the plasma membrane to execute cell death (Cai, Z. et al, Nat. Cell Biol. (2014) 16:55-65).

Cell death was quantified in 96 well plates by determination of the amount of live cell using a CellTiter 96 AQueous reagent (Promega), a calorimetric method to measure the amount of live cells by reducing tetrazolium compound [3-(4,5-dimethylthiazol-2-yl)-5-(3-carboxymethoxyphenyl)-2-(4-sulfophenyl)-2H-tetrazolium, inner salt; MTS] into formazan. Absorbance of formazan was read at 490 nm. The inhibitory activity of the test compound was quantified in a concentration response curve (CRC) experiment. Compounds were obtained as 10 mM stock solutions and were diluted 1 to 10 volumes with DMSO to yield a 1 mM solution. From this solution 2 μl were diluted with 998 μl growth medium. 100 μl of 2 μM compound solution was further diluted sequentially with a dilution factor of 2.5 by adding 150 μl growth medium. A total of 10 concentrations were tested ranging from 10 μM to 0.26 nM or from 1 μM to 0.07 nM.

U937 cells were cultured in RPM11640 Glutamax and 10% heat inactivated FBS. 50 μl cell suspension containing 1×106 cells/ml supplemented with 50 μM zVAD.fmk (Benzyloxycarbonyl-Val-Ala-Asp (OMe) fluoromethylketone) and 100 ng/ml recombinant human TNFα were dispensed in each well of a 96-well plate. 50 μl of compound dilutions (see above) were added and the cell suspension incubated overnight (18 to 24 hrs) at 37° C., 5% CO$_2$ in a humidified atmosphere (95% rH). High (no compound) and low control (no TNFα, zVAD.fmk) were tested with 7 replicates; all compound concentrations were tested in duplicates on each experimental plate.

CellTiter 96 Aqueous reagent was mixed (100 μl PMS (phenazine methosulfate) solution/2 ml MTS (3-(4,5-dimethyldiazol-2-yl)-5-(3-carboxymethoxyphenyl)-2-(4-sulfophenyl)-2H-tetrazolium, inner salt) solution) and 20 μl were added per well. After 4 hrs incubation at 37° C. (5% $CO_2$ 95% rH) optical density was measured at 490 nm on a microplate reader (Tecan Infinite M1000).

The % inhibition is expressed as percentage of the maximal inhibition value obtained in the absence of TNFα/zVAD.fmc. For each dose response experiment an $IC_{50}$ value with 95% confidence interval was calculated using the 4-parameter logistic model according to Ratkowsky and Reedy without constraints using an internal application (Biost@t-Speed LTS V2.3).

Results of biological activity are shown in Table 1 (ADP-Glo IC50 (μM) and U937 IC50 (μM))

TABLE 1

| Example | ADP-Glo IC50 [μM] | U937 IC50 [μM] |
|---|---|---|
| A | 0.0410 | 0.0080 |
| B | 0.0164 | 0.0094 |
| C | 0.0370 | 0.0590 |
| D | 0.0310 | 0.0920 |
| E | 0.0350 | 0.1970 |
| 1 | 0.0158 | 0.0059 |
| 2 | 0.0121 | 0.0038 |
| 3 | 0.0088 | 0.0081 |
| 4 | 0.0250 | 0.0050 |
| 5 | 0.0130 | 0.0030 |
| 6 | 0.0178 | 0.0117 |
| 7 | 0.0041 | 0.0036 |
| 8 | 0.0059 | 0.0010 |
| 9 | 0.0070 | 0.015 |
| 10 | 0.0081 | 0.0020 |
| 11 | 0.0099 | 0.0093 |
| 12 | 0.0130 | 0.0070 |
| 13 | 0.0149 | 0.0043 |
| 14 | 0.0185 | 0.0034 |
| 15 | 0.0090 | 0.0004 |

The invention claimed is:

1. A compound of formula I:

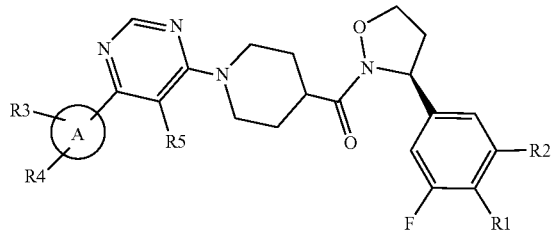

(I)

wherein
A represents a five-membered heteroaryl group in which 2 or 3 ring atoms are independently selected from nitrogen, which is optionally substituted by R3 and R4;
R1 represents H or $CH_3$,
R2 represents Cl, F or CN,
R3 represents H or $CH_3$,
R4 represents H, $CH_3$ or cyclopropyl,
R5 represents H or F;
or a pharmaceutically acceptable salt, solvate, or stereoisomer thereof.

2. A compound of the formula I according to claim 1, wherein A is selected from imidazole, pyrazole and triazole, which is optionally substituted by R3 and R4;
or a pharmaceutically acceptable salt, solvate, or stereoisomer thereof.

3. A compound of the formula I according to claim 1, wherein
A represents a heteroaryl selected from

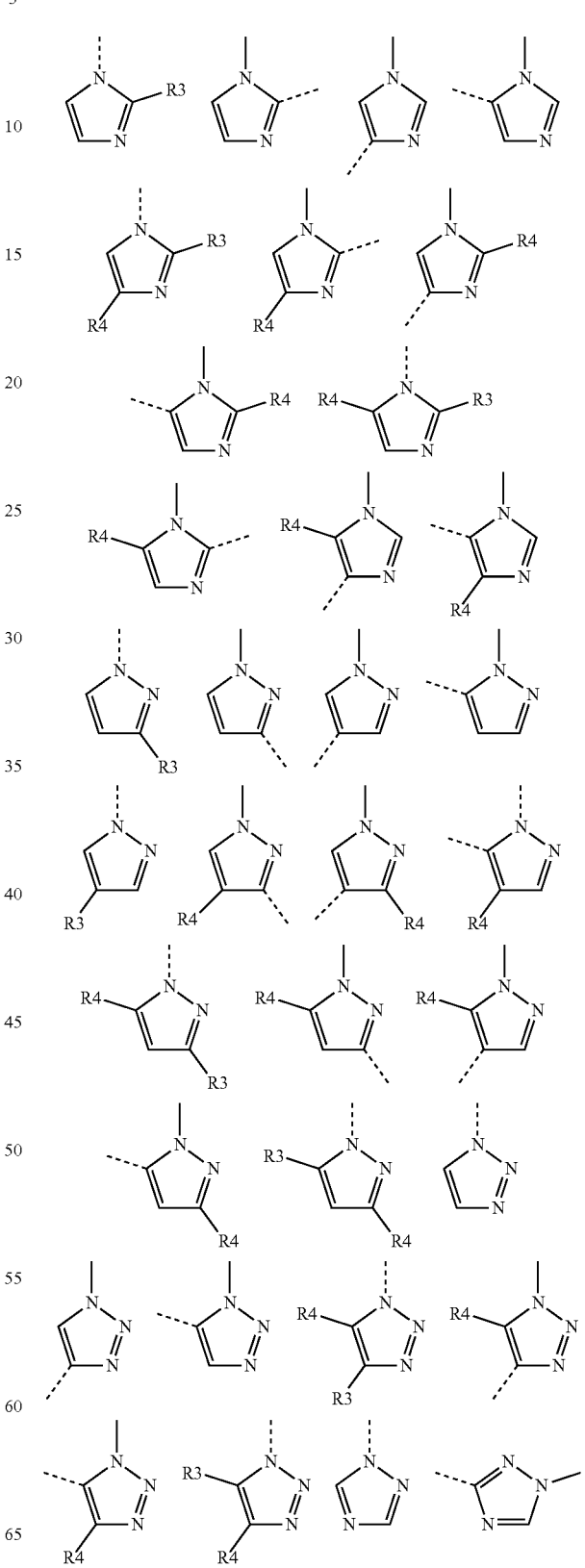

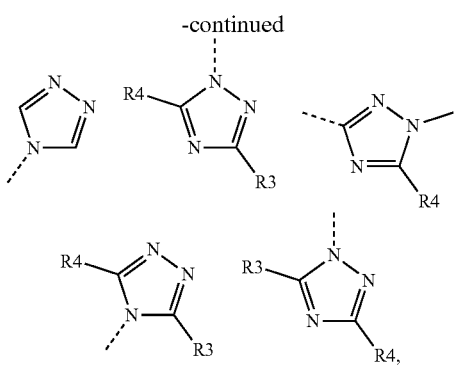

wherein the dashed line indicates the bond to the pyrimidine ring of formula I;
R3 represents H or CH₃,
R4 represents H, CH₃ or cyclopropyl,
or a pharmaceutically acceptable salt, solvate, or stereoisomer thereof.

4. A compound of the formula I according to claim 1, wherein
A represents a heteroaryl selected from
1-imidazolyl and 3-pyrazolyl,
which is optionally substituted by R3 and R4;
or a pharmaceutically acceptable salt, solvate, or stereoisomer thereof.

5. A compound of the formula I according to claim 1, wherein
A represents a heteroaryl selected from 1-imidazolyl and 3-pyrazolyl,
R1 represents H,
R2 represents CN,
R3 represents CH₃,
R4 represents H,
R5 represents H or F;
or a pharmaceutically acceptable salt, solvate, or stereoisomer thereof.

6. A compound of the formula I according to claim 1, wherein the compound of formula I is selected from
3-fluoro-5-[(3S)-2-[1-[6-(2-methylimidazol-1-yl)pyrimidin-4-yl]piperidine-4-carbonyl]isoxazolidin-3-yl]benzonitrile;
3-fluoro-2-methyl-5-[(3S)-2-[1-[6-(2-methylimidazol-1-yl)pyrimidin-4-yl]piperidine-4-carbonyl]isoxazolidin-3-yl]benzonitrile;
3-fluoro-5-[(3S)-2-[1-[6-(2-methylpyrazol-3-yl)pyrimidin-4-yl]piperidine-4-carbonyl]isoxazolidin-3-yl]benzonitrile;
[(3S)-3-(3,5-difluorophenyl)isoxazolidin-2-yl]-[1-[6-(2-methylpyrazol-3-yl)pyrimidin-4-yl]-4-piperidyl]methanone;
[(3S)-3-(3-chloro-5-fluoro-phenyl)isoxazolidin-2-yl]-[1-[6-(2-methylpyrazol-3-yl)pyrimidin-4-yl]-4-piperidyl]methanone;
3-fluoro-5-[(3S)-2-[1-[6-(3-methyl-1H-pyrazol-4-yl)pyrimidin-4-yl]piperidine-4-carbonyl]isoxazolidin-3-yl]benzonitrile;
3-[(3S)-2-[1-[6-(4-cyclopropyl-2-methyl-imidazol-1-yl)pyrimidin-4-yl]piperidine-4-carbonyl]isoxazolidin-3-yl]-5-fluoro-benzonitrile;
5-[(3S)-2-[1-[6-(4-cyclopropyl-2-methyl-imidazol-1-yl)pyrimidin-4-yl]piperidine-4-carbonyl]isoxazolidin-3-yl]-3-fluoro-2-methyl-benzonitrile;
3-[(3S)-2-[1-[6-(2,5-dimethylpyrazol-3-yl)pyrimidin-4-yl]piperidine-4-carbonyl]isoxazolidin-3-yl]-5-fluoro-benzonitrile;
3-fluoro-5-[(3S)-2-[1-[6-(3-methyl-1,2,4-triazol-1-yl)pyrimidin-4-yl]piperidine-4-carbonyl]isoxazolidin-3-yl]benzonitrile;
3-fluoro-5-[(3S)-2-[1-[6-(5-methyl-1,2,4-triazol-1-yl)pyrimidin-4-yl]piperidine-4-carbonyl]isoxazolidin-3-yl]benzonitrile;
3-fluoro-5-[(3S)-2-[1-[6-(3-methyltriazol-4-yl)pyrimidin-4-yl]piperidine-4-carbonyl]isoxazolidin-3-yl]benzonitrile;
3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
3-fluoro-5-[(3S)-2-[1-[5-fluoro-6-(4-methylpyrazol-1-yl)pyrimidin-4-yl]piperidine-4-carbonyl]isoxazolidin-3-yl]-2-methyl-benzonitrile; and
[(3S)-3-(3,5-difluorophenyl)isoxazolidin-2-yl]-[1-[5-fluoro-6-(2-methylpyrazol-3-yl)pyrimidin-4-yl]-4-piperidyl]methanone;
or a pharmaceutically acceptable salt, solvate, or stereoisomer thereof.

7. A compound of the formula I according to claim 1, wherein the compound of formula I is 3-fluoro-5-[(3S)-2-[1-[6-(2-methylimidazol-1-yl)pyrimidin-4-yl]piperidine-4-carbonyl]isoxazolidin-3-yl]benzonitrile;
or a pharmaceutically acceptable salt, solvate, or stereoisomer thereof.

8. A compound of the formula I according to claim 1, wherein the compound of formula I is 3-fluoro-5-[(3S)-2-[1-[6-(2-methylpyrazol-3-yl)pyrimidin-4-yl]piperidine-4-carbonyl]isoxazolidin-3-yl]benzonitrile;
or a pharmaceutically acceptable salt, solvate, or stereoisomer thereof.

9. A compound of the formula I according to claim 1, wherein the compound of formula I is 3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
or a pharmaceutically acceptable salt, solvate, or stereoisomer thereof.

10. A pharmaceutical composition comprising a compound according to claim 1 and at least one pharmaceutically acceptable carrier.

11. A pharmaceutical composition comprising a compound according to claim 1, at least one pharmaceutically acceptable carrier and one or more additional active pharmaceutical agent selected from a thrombolytic agent, a tissue plasminogen activator, an anticoagulant, a platelet aggregation inhibitor, an antimicrobial agent, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, a protein tyrosine kinase inhibitor, a CRTH2/D prostanoid receptor antagonist, an epinephrine inhalation aerosol, a phosphodiesterase inhibitor, a combination of a phosphodiesterase-3 inhibitor and a phosphodiesterase-4 inhibitor, a long-acting inhaled anticholinergic, a muscarinic antagonist, a long-acting muscarinic antagonist, a low dose steroid, an inhaled corticosteroid, an oral corticosteroid, a topical corticosteroid, anti-thymocyte globulin, thalidomide, chlorambucil, a calcium channel blocker, a topical emollient, an ACE inhibitor, a serotonin reuptake inhibitor, an endothelin-I receptor inhibitor, an anti-fibrotic agent, a proton-pump inhibitor, a cystic fibrosis transmembrane conductance regulator potentiator, a mucolytic agent, pancreatic enzymes, a bronchodilator, an opthalmalic intravitreal injection, an anti-vascular endothelial growth factor inhibitor, a ciliary neurotrophic growth factor agent, a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, inactivated influenza vaccine, a ciliary neurotrophic growth factor, a gene transfer agent, a topical immunomodulator, calcineurin inhibitor, an interferon gamma, an antihistamine, a monoclonal antibody, a polyclonal anti-Tcell antibody, an antithymocyte gamma globulin-equine antibody, an antithymocyte globulin-rabbit antibody, an anti-CD40 antagonist, a JAK inhibitor, and an anti-TCR murine mAb.

12. A method of treating a disease or disorder comprising administering to the subject in need thereof a compound according to claim 1, wherein the disease or disorder is selected from necrotizing enterocolitis, tuberous sclerosis, Tangier's Disease, Wohlman's Syndrome, inflammatory bowel disease, Crohn's disease, ulcerative colitis, psoriasis, retinal detachment, retinitis pigmentosa, macular degeneration, pancreatitis, atopic dermatitis, rheumatoid arthritis, psoriatic arthritis, spondyloarthritis, gout, systemic onset juvenile idiopathic arthritis (SoJIA), systemic lupus erythematosus, Sjogren's syndrome, systemic scleroderma, antiphospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia, ischemia reperfusion injury of solid organs, cerebral ischemia, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, infection, bacterial infection, staphylococcus infection, mycobacterium infection, influenza, transplant rejection, burns, hypoxia, trauma, stroke, cardiac infarction, lysosomal storage disease, Niemann-Pick disease, Gaucher's disease, Krabbe disease, amyotrophic lateral sclerosis (ALS/Lou Gehrig's Disease), HIV-associated dementia, encephalopathy, retinal degenerative disease, glaucoma, age-related macular degeneration, Friedreich's ataxia, Lewy body disease, diabetic neuropathy, polyglutamine (polyQ) diseases, Fahr disease, Menke's disease, Wilson's disease, a prion disorder, atherosclerosis, Guillain-Barre syndrome, chronic inflammatory demyelinating polyneuropathy, major depressive disorder, bipolar disorder, delirium, post-operative cognitive impairment, autism, schizophrenia, hidradenitis suppurativa and incontinentia pigmenti.

13. The method according to claim 12, wherein the disease or disorder is selected from Alzheimer's disease, multiple sclerosis, amyotrophic lateral sclerosis (ALS) and incontinentia pigmenti.

14. The method according to claim 12, wherein the disease or disorder is Alzheimer's disease.

15. The method according to claim 12, wherein the disease or disorder is multiple sclerosis.

16. The method according to claim 12, wherein the disease or disorder is amyotrophic lateral sclerosis (ALS).

17. The method according to claim 12, wherein the disease or disorder is incontinentia pigmenti.

18. A compound of formula I:

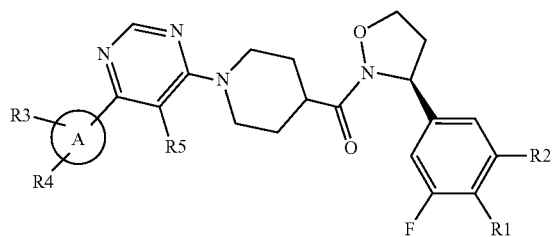

(I)

wherein
A represents a five-membered heteroaryl group in which 2 or 3 ring atoms are independently selected from nitrogen, which is optionally substituted by R3 and R4;
R1 represents H or CH$_3$,
R2 represents Cl, F or CN,
R3 represents H or CH$_3$,
R4 represents H, CH$_3$ or cyclopropyl,
R5 represents H or F;
or a pharmaceutically acceptable salt thereof.

19. A compound of the formula I according to claim 18, wherein A is selected from imidazole, pyrazole and triazole, which is optionally substituted by R3 and R4;
or a pharmaceutically acceptable salt thereof.

20. A compound of the formula I according to claim 18, wherein
A represents a heteroaryl selected from

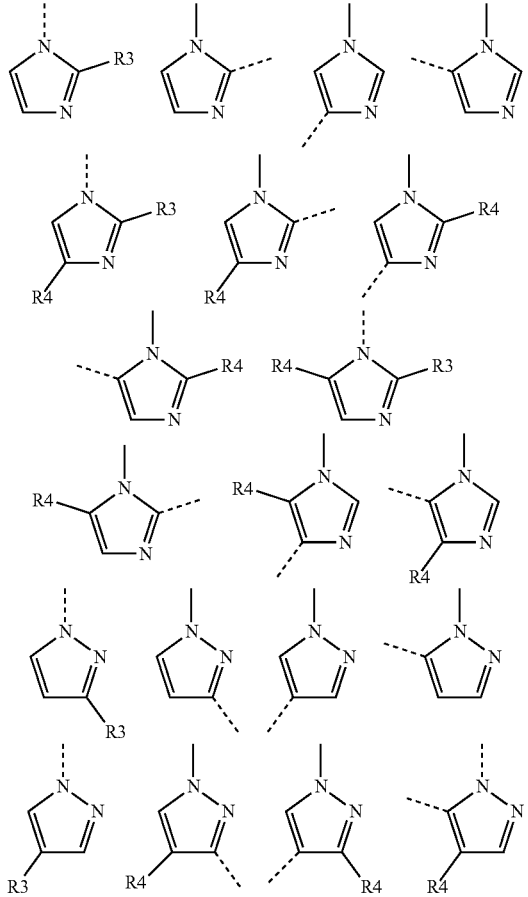

-continued

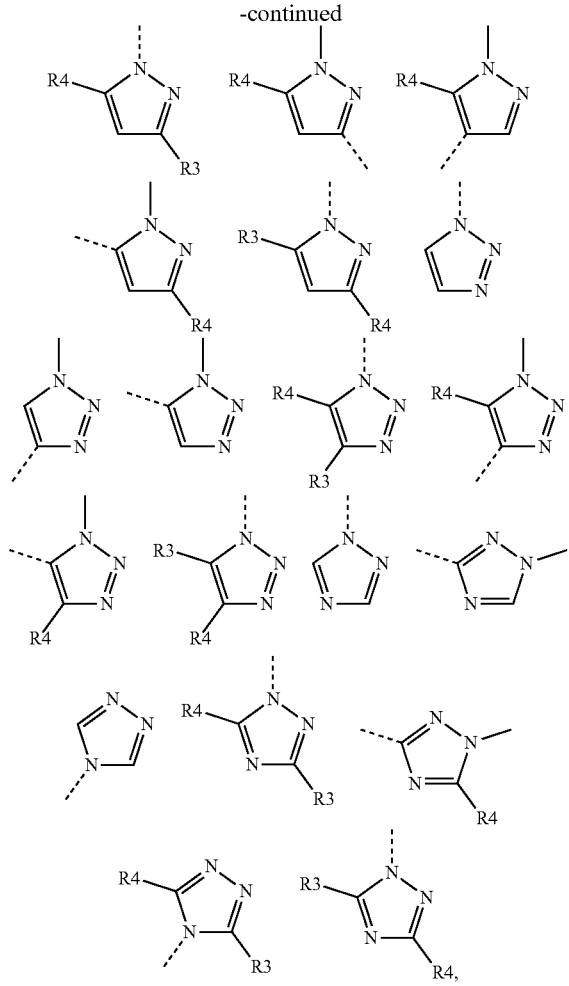

wherein the dashed line indicates the bond to the pyrimidine ring of formula I;
R3 represents H or CH₃,
R4 represents H, CH₃ or cyclopropyl,
or a pharmaceutically acceptable salt thereof.

21. A compound of the formula I according to claim 18, wherein the compound of formula I is selected from
 3-fluoro-5-[(3S)-2-[1-[6-(2-methylimidazol-1-yl)pyrimidin-4-yl]piperidine-4-carbonyl]isoxazolidin-3-yl]benzonitrile;
 3-fluoro-2-methyl-5-[(3S)-2-[1-[6-(2-methylimidazol-1-yl)pyrimidin-4-yl]piperidine-4-carbonyl]isoxazolidin-3-yl]benzonitrile;
 3-fluoro-5-[(3S)-2-[1-[6-(2-methylpyrazol-3-yl)pyrimidin-4-yl]piperidine-4-carbonyl]isoxazolidin-3-yl]benzonitrile;
 [(3S)-3-(3,5-difluorophenyl)isoxazolidin-2-yl]-[1-[6-(2-methylpyrazol-3-yl)pyrimidin-4-yl]-4-piperidyl]methanone;
 [(3S)-3-(3-chloro-5-fluoro-phenyl)isoxazolidin-2-yl]-[1-[6-(2-methylpyrazol-3-yl)pyrimidin-4-yl]-4-piperidyl]methanone;
 3-fluoro-5-[(3S)-2-[1-[6-(3-methyl-1H-pyrazol-4-yl)pyrimidin-4-yl]piperidine-4-carbonyl]isoxazolidin-3-yl]benzonitrile;
 3-[(3S)-2-[1-[6-(4-cyclopropyl-2-methyl-imidazol-1-yl)pyrimidin-4-yl]piperidine-4-carbonyl]isoxazolidin-3-yl]-5-fluoro-benzonitrile;
 5-[(3S)-2-[1-[6-(4-cyclopropyl-2-methyl-imidazol-1-yl)pyrimidin-4-yl]piperidine-4-carbonyl]isoxazolidin-3-yl]-3-fluoro-2-methyl-benzonitrile;
 3-[(3S)-2-[1-[6-(2,5-dimethylpyrazol-3-yl)pyrimidin-4-yl]piperidine-4-carbonyl]isoxazolidin-3-yl]-5-fluoro-benzonitrile;
 3-fluoro-5-[(3S)-2-[1-[6-(3-methyl-1,2,4-triazol-1-yl)pyrimidin-4-yl]piperidine-4-carbonyl]isoxazolidin-3-yl]benzonitrile;
 3-fluoro-5-[(3S)-2-[1-[6-(5-methyl-1,2,4-triazol-1-yl)pyrimidin-4-yl]piperidine-4-carbonyl]isoxazolidin-3-yl]benzonitrile;
 3-fluoro-5-[(3S)-2-[1-[6-(3-methyltriazol-4-yl)pyrimidin-4-yl]piperidine-4-carbonyl]isoxazolidin-3-yl]benzonitrile;
 3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
 3-fluoro-5-[(3S)-2-[1-[5-fluoro-6-(4-methylpyrazol-1-yl)pyrimidin-4-yl]piperidine-4-carbonyl]isoxazolidin-3-yl]-2-methyl-benzonitrile; and
 [(3S)-3-(3,5-difluorophenyl)isoxazolidin-2-yl]-[1-[5-fluoro-6-(2-methylpyrazol-3-yl)pyrimidin-4-yl]-4-piperidyl]methanone;
 or a pharmaceutically acceptable salt thereof.

22. A compound of the formula I according to claim 18, wherein the compound is 3-fluoro-5-[(3S)-2-[1-[6-(2-methylimidazol-1-yl)pyrimidin-4-yl]piperidine-4-carbonyl]isoxazolidin-3-yl]benzonitrile;
or a pharmaceutically acceptable salt thereof.

23. A compound of the formula I according to claim 22, wherein the compound is 3-fluoro-5-[(3S)-2-[1-[6-(2-methylimidazol-1-yl)pyrimidin-4-yl]piperidine-4-carbonyl]isoxazolidin-3-yl]benzonitrile.

24. A compound of the formula I according to claim 18, wherein the compound is 3-fluoro-5-[(3S)-2-[1-[6-(2-methylpyrazol-3-yl)pyrimidin-4-yl]piperidine-4-carbonyl]isoxazolidin-3-yl]benzonitrile;
or a pharmaceutically acceptable thereof.

25. A compound of the formula I according to claim 24, wherein the compound is 3-fluoro-5-[(3S)-2-[1-[6-(2-methylpyrazol-3-yl)pyrimidin-4-yl]piperidine-4-carbonyl]isoxazolidin-3-yl]benzonitrile.

26. A compound of the formula I according to claim 18, wherein the compound is 3-fluoro-5-[(3S)-2-[1-[5-fluoro-6-(2-methylimidazol-1-yl)pyrimidin-4-yl]piperidine-4-carbonyl]isoxazolidin-3-yl]benzonitrile;
or a pharmaceutically acceptable salt thereof.

27. A compound of the formula I according to claim 26, wherein the compound is 3-fluoro-5-[(3S)-2-[1-[5-fluoro-6-(2-methylimidazol-1-yl)pyrimidin-4-yl]piperidine-4-carbonyl]isoxazolidin-3-yl]benzonitrile.

* * * * *

UNITED STATES PATENT AND TRADEMARK OFFICE
CERTIFICATE OF CORRECTION

PATENT NO. : 11,897,876 B2
APPLICATION NO. : 17/983883
DATED : February 13, 2024
INVENTOR(S) : Elisabeth Defossa et al.

It is certified that error appears in the above-identified patent and that said Letters Patent is hereby corrected as shown below:

In the Specification

Column 2, Line 19, delete "trails" and insert --trials.--

Column 36, Line 29, delete "dementi" and insert --dementia--

Column 45, Line 52, delete "ansoprazole" and insert --lansoprazole--

Column 46, Line 1, delete "ansoprazole" and insert --lansoprazole--

Column 49, Line 31, delete "ansoprazole" and insert --lansoprazole--

Signed and Sealed this
Fourteenth Day of January, 2025

Derrick Brent
*Acting Director of the United States Patent and Trademark Office*